(12) United States Patent
Stoddart et al.

(10) Patent No.: US 11,155,554 B2
(45) Date of Patent: Oct. 26, 2021

(54) RIGID CHIRAL REDOX-ACTIVE ISOSCELES TRIANGULAR MATERIALS

(71) Applicants: Northwestern University, Evanston, IL (US); KING ABDULAZIZ CITY FOR SCIENCE AND TECHNOLOGY (KACST), Riyadh (SA)

(72) Inventors: James Fraser Stoddart, Evanston, IL (US); Siva Krishna Mohan Nalluri, Chicago, IL (US); Zhichang Liu, Evanston, IL (US)

(73) Assignees: Northwestern University, Evanston, IL (US); KING ABDULAZIZ CITY FOR SCIENCE AND TECHNOLOGY (KACST), Riyadh (SA)

( * ) Notice: Subject to any disclaimer, the term of this patent is extended or adjusted under 35 U.S.C. 154(b) by 253 days.

(21) Appl. No.: 16/085,436

(22) PCT Filed: Mar. 16, 2017

(86) PCT No.: PCT/US2017/022668
§ 371 (c)(1),
(2) Date: Sep. 14, 2018

(87) PCT Pub. No.: WO2017/161095
PCT Pub. Date: Sep. 21, 2017

(65) Prior Publication Data
US 2019/0077804 A1  Mar. 14, 2019

Related U.S. Application Data

(60) Provisional application No. 62/308,998, filed on Mar. 16, 2016.

(51) Int. Cl.
| *C07D 471/22* | (2006.01) |
| *H01M 4/60* | (2006.01) |
| *H01M 4/62* | (2006.01) |
| *H01M 4/02* | (2006.01) |

(52) U.S. Cl.
CPC ......... *C07D 471/22* (2013.01); *H01M 4/60* (2013.01); *H01M 4/623* (2013.01); *H01M 2004/028* (2013.01); *Y02E 60/10* (2013.01)

(58) Field of Classification Search
CPC .................................................. C07D 471/22
See application file for complete search history.

(56) References Cited

U.S. PATENT DOCUMENTS

| 9,546,169 | B2 | 1/2017 | Stoddart |
| 2008/0185555 | A1 | 8/2008 | Facchetti |
| 2011/0137025 | A1 | 6/2011 | Yaghi |
| 2015/0295229 | A1 | 10/2015 | Rosciano et al. |
| 2016/0130271 | A1 | 5/2016 | Stoddart |
| 2016/0276669 | A1 | 9/2016 | Chen |

FOREIGN PATENT DOCUMENTS

| WO | 2016149611 | 9/2016 |
| WO | 2017123843 | 7/2017 |

OTHER PUBLICATIONS

Hamilton. Chemistry: A European Journal, 2000, 6(4), 608-617 (Year: 2000).*
Armand, M., et al. "Conjugated dicarboxylate anodes for Li-ion batteries." Nature materials 8.2 (2009): 120-125.
Armand, M. et al. "Building better batteries." nature 451.7179 (2008): 652-657.
Berdugo, C. et al. "Dynamic Peptide Library for the Discovery of Charge Transfer Hydrogels." ACS applied materials & interfaces 7.46 (2015): 25946-25954.
Bhosale, S. V. et al. (2008). Chemistry of naphthalene diimides. Chemical Society Reviews, 37(2), 331-342.
Bruce, P.G. et al. "Nanomaterials for rechargeable lithium batteries." Angewandte Chemie International Edition 47.16 (2008): 2930-2946.
Chen, D., et al. "A Rigid Naphthalenediimide Triangle for Organic Rechargeable Lithium-Ion Batteries." Advanced Materials 27.18 (2015): 2907-2912.
Deng, W., et al. "A perylene diimide crystal with high capacity and stable cyclability for Na-ion batteries." ACS applied materials & interfaces 7.38 (2015): 21095-21099.
European Patent Office, Extended European Search Report and European Search Opinion for application 17767508.9, dated Oct. 10, 2019.
Gawronski, J., et al. "Novel Chiral Pyromellitdiimide (1, 2, 4, 5-Benzenetetracarboxydiimide) Dimers and Trimers: Exploring Their Structure, Electronic Transitions, and Exciton Coupling." Chemistry—A European Journal 8.11 (2002): 2484-2494.
Goodenough, J. B., et al. "Challenges for rechargeable Li batteries." Chemistry of materials 22.3 (2010): 587-603.
Guo, X., et al. "Imide-and amide-functionalized polymer semiconductors." Chemical reviews 114.18 (2014): 8943-9021.
Han, X., et al. "Aromatic carbonyl derivative polymers as high-performance Li-ion storage materials." Advanced materials 19.12 (2007): 1616-1621.
Hanwell, M. D. et al. "Avogadro, open chemistry, and chemical semantics." Abstracts of Papers of the American Chemical Society. vol. 244. 2012.
Haeupler, B. et al. "Carbonyls: powerful organic materials for secondary batteries." Advanced Energy Materials 5.11 (2015): 1402034.
International Searching Authority, International Search Report and Written Opinion for application PCT/US2017/022668, dated Jun. 1, 2017.

(Continued)

Primary Examiner — Noble E Jarrell
(74) Attorney, Agent, or Firm — Quarles & Brady LLP; Tolga Gulmen

(57) ABSTRACT

Provided herein are rigid macrocycles comprising a first redox-active subunit and a second redox-active subunit, wherein the first redox-active unit and the second redox-active unit are different subunits. Also provided herein are methods of preparation of the rigid macrocycles and use thereof, for example, in the first of energy generation and storage.

22 Claims, 25 Drawing Sheets

(56) References Cited

OTHER PUBLICATIONS

Kaik, M. et al. "Unprecedented selectivity in the formation of large-ring oligoimines from conformationally bistable chiral diamines." Organic letters 8.14 (2006): 2921-2924.

Kaik, M., et al. "Facile monoprotection of trans-1, 2-diaminocyclohexane." Tetrahedron: Asymmetry 14.11 (2003): 1559-1563.

Katz, H. E., et al. "A soluble and air-stable organic semiconductor with high electron mobility." Nature 404.6777 (2000): 478-481.

Liu, Z., et al. "Assembly of supramolecular nanotubes from molecular triangles and 1, 2-dihalohydrocarbons." Journal of the American Chemical Society 136.47 (2014): 16651-16660.

Liu, Z., et al. "Supramolecular Gelation of Rigid Triangular Macrocycles through Rings of Multiple C—H—O Interactions Acting Cooperatively." The Journal of organic chemistry 81.6 (2016): 2581-2588.

Maloney, R. P., et al. "Structure-Property Relationships of Naphthalene Diimide Based Organic Electrodes." Meeting Abstracts. No. 5. The Electrochemical Society, 2013.

Mas-Torrent, M. et al. "Role of molecular order and solid-state structure in organic field-effect transistors." Chemical reviews 111.8 (2011): 4833-4856.

Mizuno, As., et al. "Discovery of the K 4 Structure Formed by a Triangular p Radical Anion." Journal of the American Chemical Society 137.24 (2015): 7612-7615.

Nalluri, S. K. M., et al. "Biocatalytic Self-Assembly of Supramolecular Charge-Transfer Nanostructures Based on n-Type Semiconductor-Appended Peptides." Angewandte Chemie International Edition 53.23 (2014): 5882-5887.

Novák, P., et al. "Electrochemically active polymers for rechargeable batteries." Chemical Reviews 97.1 (1997): 207-282.

Sakai, N., et al. "Supramolecular n/p-heterojunction photosystems with antiparallel redox gradients in electron-and hole-transporting pathways." Journal of the American Chemical Society 132.20 (2010): 6923-6925.

Schneebeli, S. T., et al. "Electron sharing and anion-p recognition in molecular triangular prisms." Angewandte Chemie International Edition 52.49 (2013): 13100-13104.

Shimizu, A., et al. "Introduction of two lithiooxycarbonyl groups enhances cyclability of lithium batteries with organic cathode materials." Journal of Power Sources 260 (2014): 211-217.

Shukla, D., et al. "Thin-film morphology control in naphthalene-diimide-based semiconductors: high mobility n-type semiconductor for organic thin-film transistors." Chemistry of Materials 20.24 (2008): 7486-7491.

Song, Z. et al. "Polyimides: promising energy-storage materials." Angewandte Chemie International Edition 49.45 (2010): 8444-8448.

Song, Z. et al. "Towards sustainable and versatile energy storage devices: an overview of organic electrode materials." Energy & Environmental Science 6.8 (2013): 2280-2301.

Sun, D. et al. "Through-Space (Cofacial) p-Delocalization among Multiple Aromatic Centers: Toroidal Conjugation in Hexaphenylbenzene-like Radical Cations." Angewandte Chemie International Edition 44.32 (2005): 5133-5136.

Suraru, S.-L., et al. "Strategies for the synthesis of functional naphthalene diimides." Angewandte Chemie International Edition 53.29 (2014): 7428-7448.

Vadehra, G. S., et al. "Naphthalene diimide based materials with adjustable redox potentials: Evaluation for organic lithium-ion batteries." Chemistry of Materials 26.24 (2014): 7151-7157.

Walker, W., et al. "Ethoxycarbonyl-based organic electrode for Li-batteries." Journal of the American Chemical Society 132.18 (2010): 6517-6523.

Wang, C., et al. "Semiconducting p-conjugated systems in field-effect transistors: a material odyssey of organic electronics." Chemical reviews 112.4 (2012): 2208-2267.

Wang, H.-G., et al. "Tailored aromatic carbonyl derivative polyimides for high-power and long-cycle sodium-organic batteries." Advanced Energy Materials 4.7 (2014): 1301651.

Whittingham, M. S. "Lithium batteries and cathode materials." Chemical reviews 104.10 (2004): 4271-4302.

Wu, Y., et al. "Charge and spin transport in an organic molecular square." Angewandte Chemie International Edition 54.41 (2015): 11971-11977.

Zhan, X., et al. "Rylene and related diimides for organic electronics." Advanced Materials 23.2 (2011): 268-284.

Zheng, Q., et al. "Pyromellitic diimides: minimal cores for high mobility n-channel transistor semiconductors." Journal of the American Chemical Society 130.44 (2008): 14410-14411.

\* cited by examiner

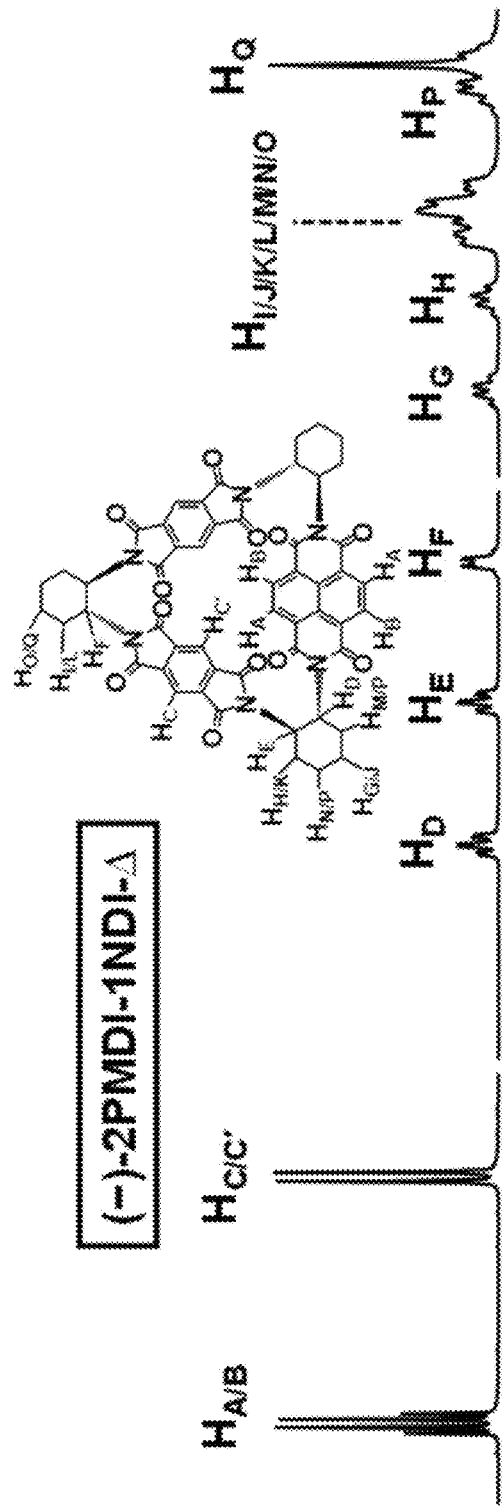
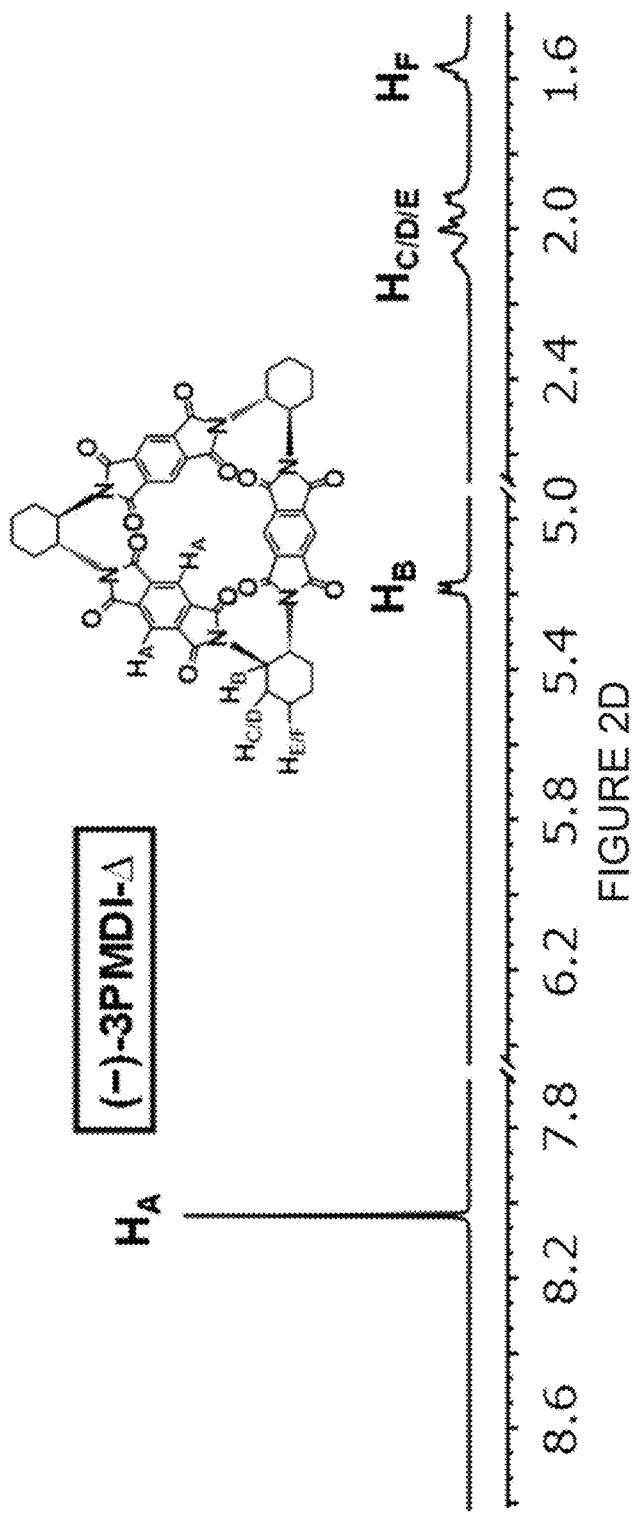
FIGURE 2C
FIGURE 2D

RIGID CHIRAL REDOX-ACTIVE ISOSCELES TRIANGULAR MATERIALS

CROSS-REFERENCE TO RELATED APPLICATIONS

This patent application is a national stage filing under 35 U.S.C. § 371 of International Application No. PCT/US2017/022668, filed Mar. 16, 2017, which claims priority benefit from U.S. Provisional Patent Application Ser. No. 62/308,998, filed 16 Mar. 2016, both of which are incorporated herein by reference in their entirety.

FIELD OF INVENTION

Provided herein are compositions and devices comprising rigid macrocycles having redox-active subunits and methods of preparation and use thereof, for example, in the field of energy generation and storage.

BACKGROUND

Understanding of the geometrical constraints between multiple redox-active aromatic building blocks that exhibit efficient electron hopping and delocalization has presented a considerable challenge to those researchers fabricating organic photovoltaic and molecular electronic devices. The efficiency of intra- as well as intermolecular charge mobilities in organic semiconductors relies on maximizing electronic coupling and minimizing reorganizational energies associated with charge transport between neighboring n-conjugated redox-active units. These factors are determined, however, by (i) the relative orientations, (ii) the intermolecular distances and (iii) the energy matches involving neighboring redox-active units. In this context, a number of n-conjugated aromatic diimides, particularly pyromellitic diimides (PMDIs), naphthalene diimides (NDIs) and perylene diimides (PDIs), all of which exhibit unique redox characteristics, have been employed as n-type organic semiconductors with potential applications in organic field-effect transistors, photovoltaics, and energy storage devices, including lithium- and sodium-ion batteries. In particular, $\pi$-conjugated electron-deficient NDIs have been investigated increasingly in a number of fields such as charge transport, chemosensing, synthetic membrane transport, organocatalysis and biocatalytic charge transfer assemblies. Despite continued efforts relating to a number of $\pi$-conjugated redox-active molecules, the exact structure-performance relationship for efficient charge mobilities remains elusive.

A chiral equilateral triangle (−)-3NDI-Δ, consisting of three redox-active NDI units that can accept reversibly up to six electrons has been reported.[Schneebeli, S. T. et al., *Angew. Chem., Int. Ed.* 2013, 52, 13100; U.S. Pat. No. 9,546,169; U.S. Patent Appl. Pub. No. 2016/0276669; and International Patent Appl. Ser. No. PCT/US2017/013301, all of which are incorporated herein by reference] Both the experimental observations, as well as theoretical calculations on (−)-3NDI-Δ, reveal that a remarkable cyclical through-space electron delocalization occurs among the overlapping $\pi$-orbitals of the pairs of adjacent NDI units, as evidenced by the complete sharing of an unpaired electron in the stable radical anionic state of this equilateral triangle. Another important aspect of (−)-3NDI-Δ is the formation of a supramolecular gel, composed of a dense network of entangled nanofibers, in (E)-1,2-dichloroethene, as well as by its solvent-dependent packing into a variety of solid-state superstructures—that is, the formation of (i) non-tubular superstructures in $CHCl_3$, (ii) single-handed helical tetrameric nanotubes in $ClCH_2CH_2Cl$, and (iii) rigid infinite non-helical nanotubes in $ClCH_2CH_2Br$, $ClCH_2CH_2I$, and $BrCH_2CH_2Br$ driven by the columnar stacking of (−)-3NDI-Δ with a 60° rotational angle between the neighboring triangles and employing multiple weak [C—H . . . O] interactions associated with directed halogen-halogen (X) interactions along the [X . . . X]-bonded solvent chains inside the nanotubes. The X-ray superstructure of the radical anion of (−)-3NDI-Δ, formed by electrochemical reduction, revealing the formation of an impressive $K_4$ structure, driven by the intermolecular $\pi$-$\pi$ stacking interactions of the NDI radical anions in the equilateral triangle has also been reported.[Mizuno, A. et al. *J. Am. Chem. Soc.* 2015, 137, 7612.] In addition to its remarkable redox-active characteristics and high thermal stability, (−)-3NDI-Δ has been exploited as the active material in organic rechargeable LIBs.[Chen, D. et al. *Adv. Mater.* 2015, 27, 2907.] It should be emphasized that all of these observations are a consequence of three equivalent NDI units arranged in a shape-persistent triangular structure.

Despite the fact that a three-dimensional rigid nanoporous framework of the organic active material plays a role in achieving high cell performances, a comprehensive understanding of structure-performance relationships has still to be explored. It remains, therefore, a puzzle as to what happens to the molecular properties if one mixes different redox-active subunits.

Motivated by the global energy demand in this century, rechargeable lithium-ion batteries (LIBs) have resulted in a surge of interest as the state-of-the-art power sources for electronic devices, such as mobile phones and laptops, as well as electric cars because of their high energy and power densities. As a result, there exists a need for new redox-active materials that may be exploited for the fabrication of LIBs as well as other devices and systems.

SUMMARY OF THE INVENTION

One aspect of the invention provides rigid macrocycles comprising a first redox-active subunit and a second redox-active subunit, wherein the first redox-active unit and the second redox-active unit are different subunits. In some embodiments, the macrocycle further comprises a third redox-active subunit, wherein second redox-active subunit and the third redox-active subunit are the same subunits. In some embodiments, the macrocycles further comprises a chiral linking subunit, wherein the chiral linking subunit links one or more combinations of the first redox-active subunit and the second redox-active subunit, the second redox-active subunit and the third redox-active subunit, or the third redox-active subunit and the first redox-active subunit. In particular embodiments, the chiral linking subunit is (i) a (RR)-trans-1,2-cycloalkyl subunit, (ii) a (SS)-trans-1,2-cycloalkyl subunit, or a derivative of either (i) or (ii). In some embodiments, the redox-active subunits form a triangular macrocycle having $C_2$ symmetry.

In some embodiments, the first redox-active subunit is a n-conjugated aromatic diimide and wherein the second redox-active subunit is a n-conjugated aromatic diimide. In particular embodiments, the first redox-active subunit is a pyromellitic diimide-based (PMDI) subunit, a naphthalene diimide-based (NDI) subunit, or a perylene diimide-based (PDI) subunit and wherein the second redox-active subunit is a PMDI subunit, a NDI subunit, or a PDI subunit. In certain embodiments, the macrocycle comprises a compound of (i) Formula (I):

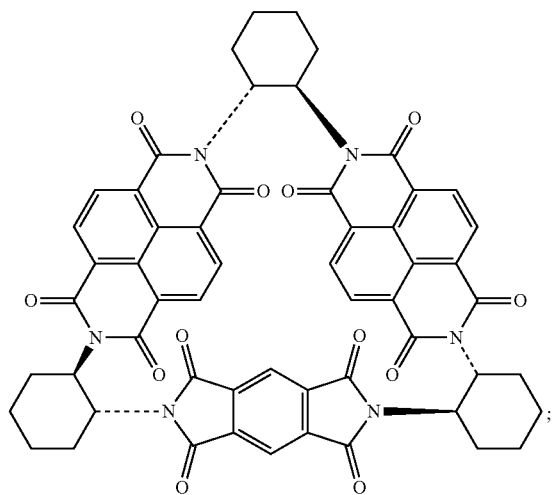

(ii) Formula (II):

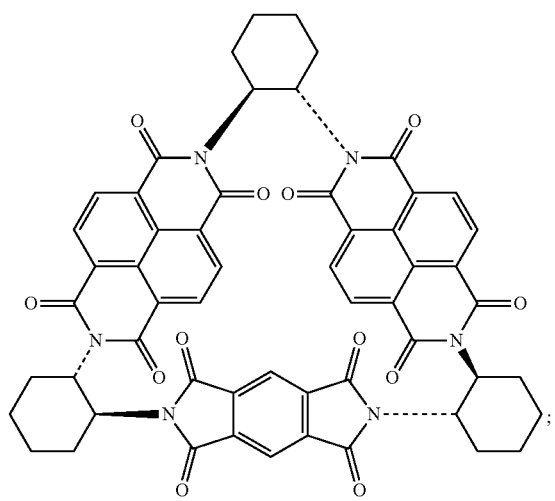

or a derivative thereof of either Formula (I) or Formula (II). In other embodiments, the macrocycle comprises a compound of (i) Formula (III):

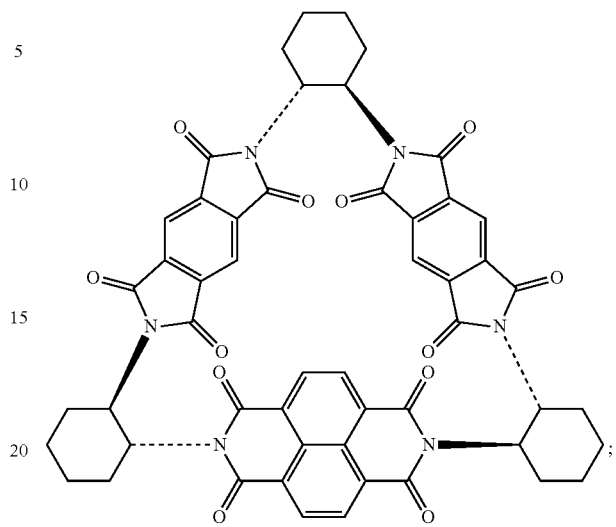

(ii) Formula (IV):

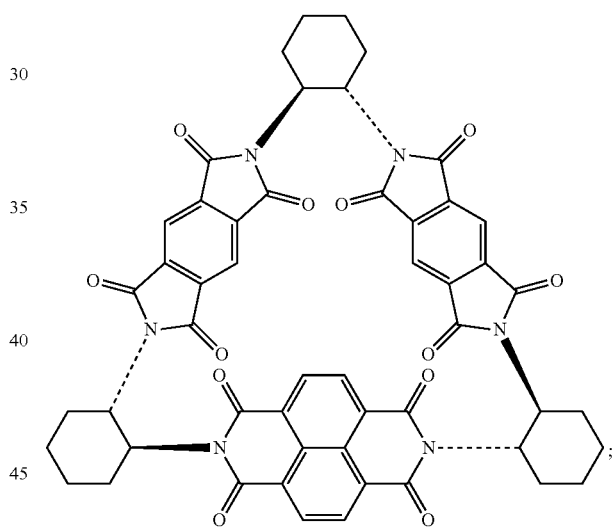

or a derivative thereof of either Formula (III) or Formula (IV).

Another aspect of the invention provides cathodic materials comprising any of the rigid macrocycles described herein. In some embodiments, the cathodic material further comprises a binder material. Examples of binder materials include, but are not limited to, the binder material comprising a polymer selected from the group consisting of: styrene-butadiene rubber (SBR); polyvinylidene fluoride (PVDF); polytetrafluoroethylene (PTFE); copolymer of tetrafluoroethylene, hexafluoropropylene, and vinylidene fluoride; copolymer of hexafluoropropylene and vinylidene fluoride; copolymer of tetrafluoroethylene and perfluorinated vinyl ether. In some embodiments, the cathodic material further comprises an electron-conducting additive. Examples of electron-conducting additives include, but are not limited to, a carbon or graphitic material selected from the list consisting of: a graphite, a carbon black, a graphene, a carbon nanotube, a chemically-etched or expanded soft carbon, a chemically-etched or expanded hard carbon, and an exfoliated activated carbon.

Another aspect of the invention provides cathodes comprising any of the cathodic materials or macrocycles described herein.

Another aspect of the invention provides batteries comprising any of the cathodes, cathodic material, or macrocycles described herein. In some embodiments, the batter comprises an electrolyte. Examples of electrolytes include, but are not limited to, non-coordinating anion salts such as lithium hexafluorophosphate, lithium hexafluoroarsenate monohydrate, lithium perchlorate, lithium tetrafluoroborate, and/or lithium triflate.

Another aspect of the invention provides for methods for preparing the rigid macrocycles disclosed herein. In some embodiments, the method comprised cyclocondensing a first reagent, wherein the first reagent comprises one of a first redox-active subunit, and a second reagent, wherein the second reagent comprises a second redox-active subunit, wherein the first redox-active subunit and the second redox-active subunit are different.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

FIG. 2C shows a comparison of the annotated $^1$H NMR spectra (500 MHz, CDCl$_3$, 298 K) of the molecular triangle (−)-2PMDI-1NDI-Δ.

FIG. 2D shows a comparison of the annotated $^1$H NMR spectra (500 MHz, CDCl$_3$, 298 K) of the molecular triangle (−)-3PMDI-Δ.

DETAILED DESCRIPTION OF THE INVENTION

Figure 1A:
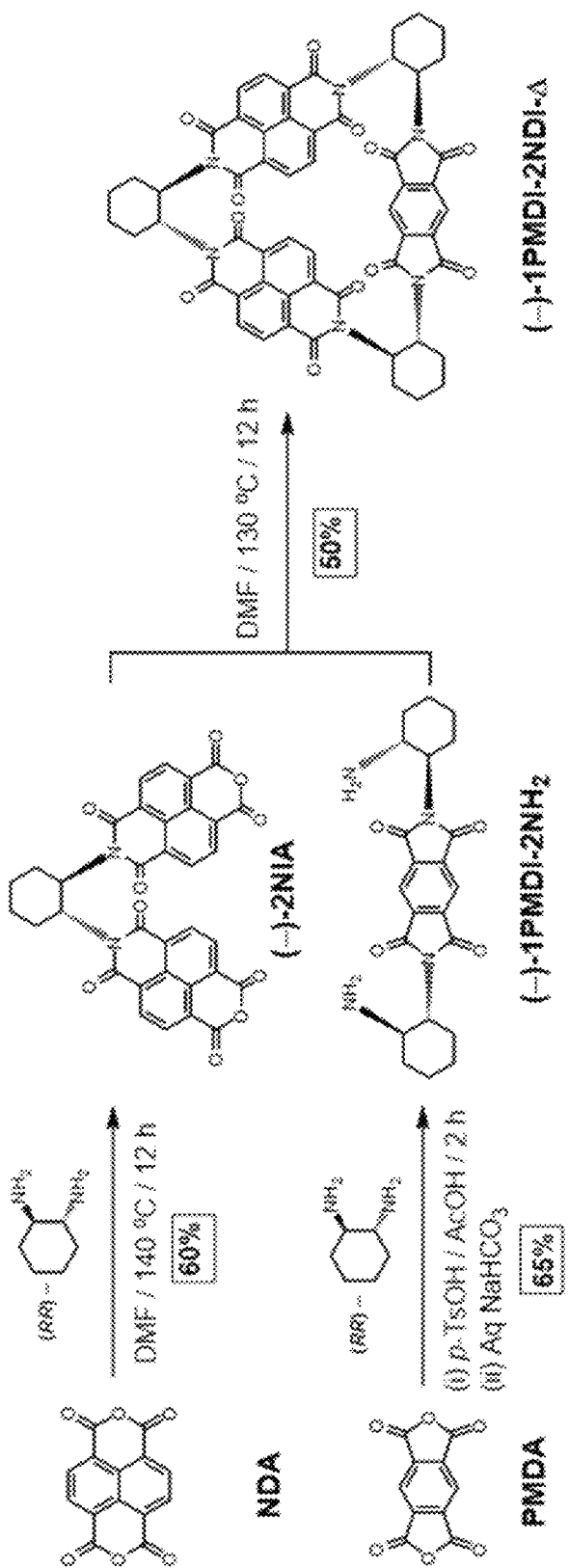
FIG. 1A shows a stereospecific stepwise preparation of chiral isosceles triangle (−)-1PMDI-2NDI-Δ from (RR)-trans-1,2-cyclohexanediamine, naphthalenetetra-carboxylic dianhydride (NDA) and pyromellitic dianhydride (PMDA).

Disclosed herein are rigid chiral redox-active triangular macrocycles. Also disclosed are methods of synthesizing the redox-active macrocycles as well as devices fabricated from the disclosed macrocycles. The redox-active macrocycles comprise a mixture of redox-active subunits that are capable of undergoing reversibly accept electrons. Because of the use of different redox-active subunits, the subunits may be sequentially reduced and the reduction potentials for the macrocycle may be significantly tuned to provide unique electrochemical behavior. As a result, these redox-active macrocycles may be exploited for novel device fabrication.

Rigid macrocycles are cyclic macromolecules or a macromolecular cyclic portion of a molecule that is constrained against large-amplitude conformational rearrangement around the cyclic portion of the molecule. Rigid macrocycles may be composed of one or more subunits arranged in a cyclic manor. In certain embodiments, the rigid macrocycle is composed of two or more subunits. In particular embodiments, the rigid macrocycle is composed of two alternating subunits where the first alternating subunit is a redox-active subunit and the second alternating subunit is a linking subunit. The rigid macrocycles disclosed herein may have three redox-active subunits and three linking subunits.

The rigid macrocycles disclosed herein comprise a first redox-active subunit and a second redox-active subunit, wherein the first redox-active unit and the second redox-active unit are different subunits. The macrocycles may further comprise a third redox-active subunit. In particular embodiments, the second redox-active subunit and the third redox-active subunit are the same subunits. In particular embodiments, the macrocycle comprises a first, a second, and a third redox-active subunit where the second and third are the same subunit but the first is different than either the second or third subunit. Macrocycles of this type may have $C_2$ symmetry.

The first and/or second redox-active subunit may be a n-conjugated aromatic diimide. In certain embodiments, the first and/or second redox-active subunit is a pyromellitic diimide-based (PMDI) subunit, a naphthalene diimide-based (NDI) subunit, or a perylene diimide-based (PDI) subunit.

In a particular embodiment, the NDI subunit is derived from a compound of Formula

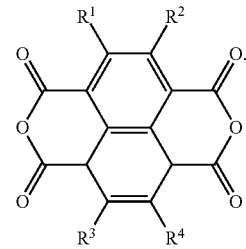

Each of $R^1$, $R^2$, $R^3$, and $R^4$ may be, independently, hydrogen, a halogen, an alkyl moiety, an alkenyl moiety, an alkynyl moiety, a hydroxyl moiety, an alkoxy moiety, a phenoxy moiety, a carbonyl moiety, a cyanide moiety, a sulfate moiety, or other functional group. In particular embodiments, each of R1, R2, R3, and R4 may be, independently, hydrogen, fluorine, chlorine, bromine, iodine, a $C_1$-$C_4$ alkyl moiety, a $C_1$-$C_4$ alkenyl moiety, a $C_1$-$C_4$ alkynyl moiety, a $C_0$-$C_4$ hydroxyl moiety, a $C_1$-$C_4$ alkoxy moiety, a $C_1$-$C_4$ phenoxy moiety, a $C_1$-$C_4$ carbonyl moiety, a $C_1$-$C_4$ cyano moiety, or a $C_1$-$C_4$ sulfate moiety. In the Examples that follow, macrocycles prepared from the compound of Formula (1) where each of R1, R2, R3, and R4 are hydrogen and the use thereof in the preparation of batteries is demonstrated. A person of skill in the art is capable of preparing derivatives of the macrocycles disclosed in the Examples by substituting those particular NDI subunits with any of the other NDI subunits disclosed herein.

In a particular embodiment, the PMDI subunit is derived from a compound of Formula (2):

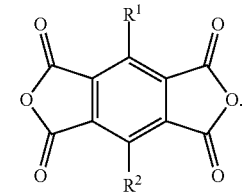

Each of $R^1$ and $R^2$ may be, independently, hydrogen, a halogen, an alkyl moiety, an alkenyl moiety, an alkynyl moiety, a hydroxyl moiety, an alkoxy moiety, a phenoxy moiety, a carbonyl moiety, a cyanide moiety, a sulfate moiety, or other functional group. In particular embodiments, each of R1, R2, R3, and R4 may be, independently, hydrogen, fluorine, chlorine, bromine, iodine, a $C_1$-$C_4$ alkyl moiety, a $C_1$-$C_4$ alkenyl moiety, a $C_1$-$C_4$ alkynyl moiety, a $C_0$-$C_4$ hydroxyl moiety, a $C_1$-$C_4$ alkoxy moiety, a $C_1$-$C_4$ phenoxy moiety, a $C_1$-$C_4$ carbonyl, a $C_1$-$C_4$ cyano moiety, or a $C_1$-$C_4$ sulfate moiety. In the Examples that follow, macrocycles prepared from the compound of Formula (2) where each of R1 and R2 are hydrogen and the use thereof in the preparation of batteries is demonstrated. A person of skill in the art is capable of preparing derivatives of the macrocycles disclosed in the Examples by substituting those particular PMDI subunits with any of the other PMDI subunits disclosed herein.

The macrocycles further comprise a linking subunit that links one or more combinations of the first redox-active subunit and the second redox-active subunit, the second redox-active subunit and the third redox-active subunit, or the third redox-active subunit and the first redox-active subunit. A macrocycle may have three identical linking subunits in some embodiments, but may also have two different linking subunits or three different linking subunits in other embodiments. The linking subunit may be a cycloalkyl subunit, but need not be. In some embodiments, the linking subunit is chiral.

In particular embodiments, the linking subunits are chiral cycloalkyl subunits. The cycloalkyl subunits may have two chiral centers at adjacent carbon positions. In particular embodiments, the linking subunit is an (RR)-1,2-trans-cycloalky subunit or a (SS)-1,2-trans-cycloalky subunit. In particular embodiments, the cycloalkyl subunit is a $C_4$-$C_8$ cycloalkyl subunit. The cycloalkyl subunit may be a substituted or unsubstituted cycloalkyl subunit. Substituents may include hydrocarbon moieties, halogen moieties, oxygen-containing moieties, nitrogen-containing moieties, sulfur containing moieties, or combinations thereof. In certain embodiments, substituents may be $C_{1-6}$ alkyl moieties, $C_{1-6}$ alkenyl moieties, $C_{1-6}$ alkynyl moieties, phenyl moieties, halo moieties, $C_{0-6}$ hydroxyl moieties, $C_{1-6}$ ether moieties, $C_{1-6}$ carbonyl moieties, $C_{1-6}$ aldehyde moieties, $C_{1-6}$ carboxyl moieties, $C_{1-6}$ ester moieties, or combinations thereof. In the Examples that follow, the macrocycles are prepared from (RR)-1,2-trans-cyclohexyl subunits, but other linking subunits may also be used. A person of skill in the art is capable of preparing derivatives of the macrocycles disclosed in the Examples by substituting those particular from (RR)-1,2-trans-cyclohexyl subunits with any of the other linking subunits disclosed herein.

In some embodiments, the macrocycle comprises a compound of Formula (3)

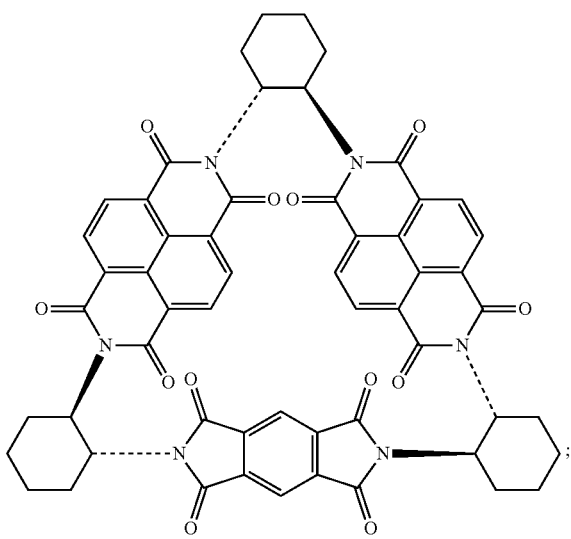

or a compound of Formula (4)

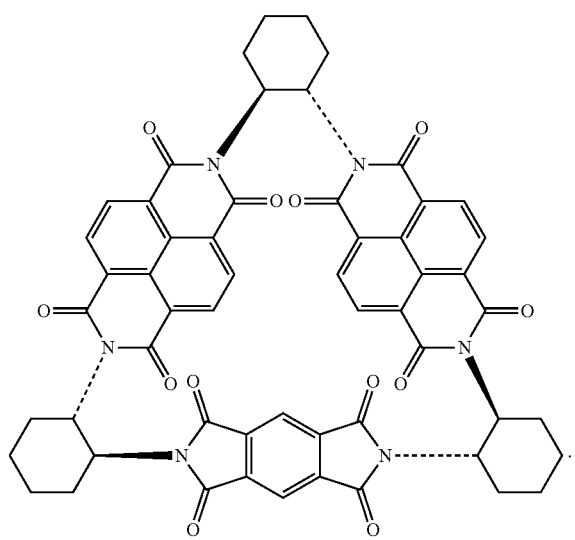

Compounds of Formulas (3) or (4) may be prepared by the cyclocondensation of two NDI redox-active subunits and one redox active PMDI subunit. The compound of Formulas (3) and (4) differs in the choice of the linking subunit. One uses (RR)-1,2-trans-cyclohexyl subunits and the other uses a (SS)-1,2-trans-cyclohexyl subunits. Derivatives of the compounds of Formulas (3) or (4) may be prepared by replacing a NDI redox-active subunit with any of the NDI redox-active subunits disclosed above, the PMDI redox-active subunit with any of the PMDI redox-active subunits disclosed above, replacing a linking subunit with any of the linking subunits disclosed above, or any combination thereof. Derivative of the compounds of Formulas (3) or (4) may be substituted derivative, where the substituent may be an alkyl moiety, an alkenyl moiety, an alkynyl moiety, a hydroxyl moiety, an alkoxy moiety, a phenoxy moiety, a carbonyl moiety, a cyanide moiety, a sulfate moiety, or other functional group. The compound of Formula (3) may be referred to as (−)-1PMDI-2NDI-Δ.

In some embodiments, the macrocycle comprises a compound of Formula (5)

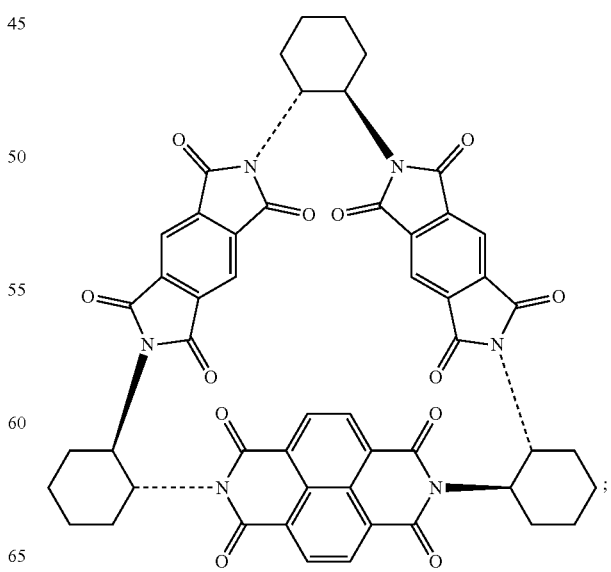

or a compound of Formula (6)

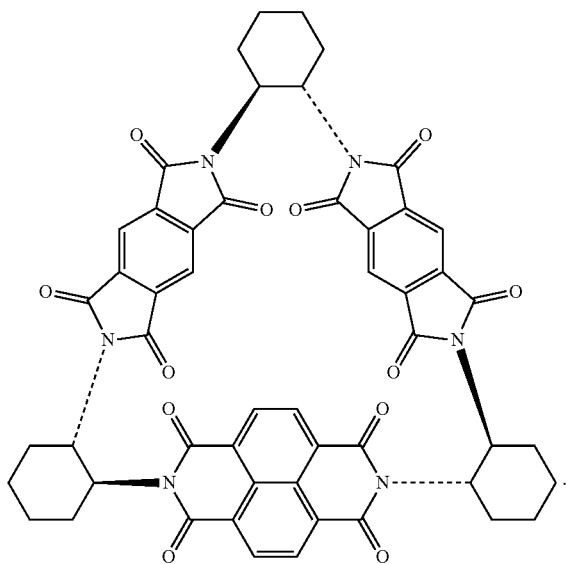

Compounds of Formulas (5) or (6) may be prepared by the cyclocondensation of two NDI redox-active subunits and one redox active PMDI subunit. The compound of Formulas (5) and (6) different in the choice of the linking subunit. One uses (RR)-1,2-trans-cyclohexyl subunits and the other uses a (SS)-1,2-trans-cyclohexyl subunits. Derivatives of the compounds of Formulas (5) or (6) may be prepared by replacing a PMDI redox-active subunit with any of the PMDI redox-active subunits disclosed above, the NDI redox-active subunit with any of the NDI redox-active subunits disclosed above, replacing a linking subunit with any of the linking subunits disclosed above, or any combination thereof. Derivative of the compounds of Formulas (5) or (6) may be substituted derivative, where the substituent may be an alkyl moiety, an alkenyl moiety, an alkynyl moiety, a hydroxyl moiety, an alkoxy moiety, a phenoxy moiety, a carbonyl moiety, a cyanide moiety, a sulfate moiety, or other functional group. The compound of Formula (5) may be referred to as (−)-2PMDI-1NDI-Δ.

As further described below, $^1$H and $^{13}$C NMR spectroscopic investigations in solution confirm the lower symmetry ($C_2$ point group) associated with the isosceles triangles of Formulas (3) and (5). Single-crystal X-ray diffraction analyses reveal their rigid triangular prism-like geometries. Unlike previously investigated equilateral triangles containing three identical PMDI or NDI subunits, both isosceles triangles do not choose to form one-dimensional supramolecular nanotubes by dint of [C—H . . . O] interaction-driven columnar stacking. Intriguingly, the rigid isosceles triangle, composed of one NDI and two PMDI subunits, forms—in the presence of N,N-dimethylformamide (DMF)—two different types of intermolecular NDI-NDI and NDI-PMDI π-π stacking dimers with opposite helicities in the solid-state. Cyclic voltammetry reveals that both isosceles triangles can accept reversibly up to six electrons. Continuous-wave electron paramagnetic resonance (EPR) and electron-nuclear double resonance (ENDOR) spectroscopic investigations, supported by DFT calculations, on the single-electron reduced radical anions of the isosceles triangles confirm the selective sharing of the unpaired electrons among the adjacent redox-active NDI subunit(s) within both molecules. The isosceles triangles have been employed as electrode-active materials in organic rechargeable lithium-ion batteries.

The redox-active macrocycles may be prepared by cyclocondensing a first reagent, wherein the first reagent comprises one of a first redox-active subunit, and a second reagent, wherein the second reagent comprises a second redox-active subunit. The first redox-active subunit and the second redox-active subunit are different. The second reagent may further comprises a third redox active subunit. In certain embodiments, the second redox-active subunit and the third redox-active subunit are the same.

In some embodiments, the second reagent comprises two NDI subunits linked via a linking subunit and the first reagent comprises a PMDI subunit linking two linking subunits. The NDI subunits may be any of the NDI subunits described above. In some embodiments, the NDI subunits are the same. The PMDI subunit may be any of the PMDI subunits described above. The linking subunit may be any of the linking subunits described above. In particular embodiments, the linking subunit is a (RR)-trans-1,2-cycloalkyl subunit, a (SS)-trans-1,2-cycloalkyl subunit or a derivative of either.

In particular embodiments, the second reagent comprises a compound of Formula (7):

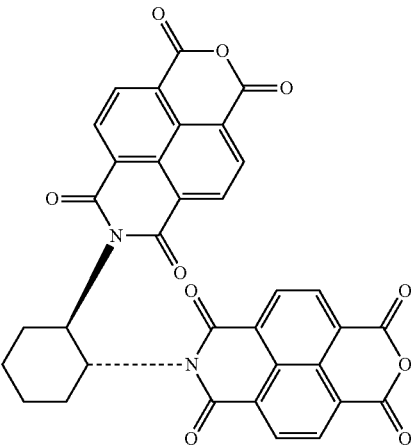

or a compound of Formula (8)

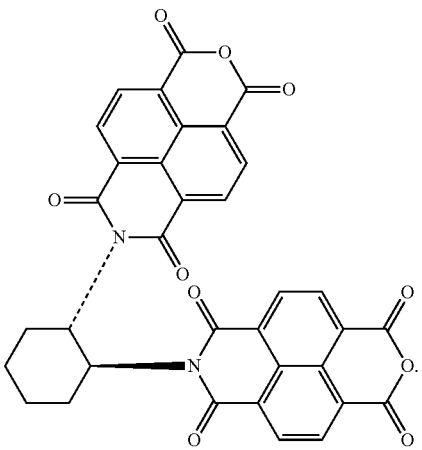 [SMILES: O=C1OC(=O)c2ccc3c4c(ccc1c24)C(=O)N([C@H]1CCCC[C@@H]1N1C(=O)c2ccc4c5c(ccc(c25)C1=O)C(=O)OC4=O)C3=O]

Derivative of either of Formulas (7) or (8) may also be used to prepare the macrocycle.

Compounds of Formulas (7) or (8) as well as derivatives of either Formulas (7) or (8) may be cyclocondensed with a compound of Formula (9)

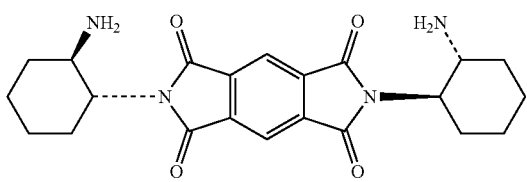

or a compound of Formula (10)

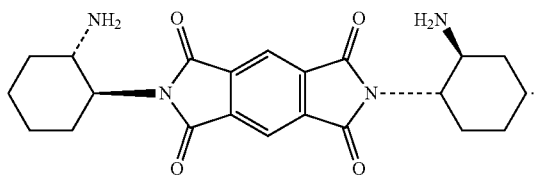

Derivative of either of Formulas (9) or (10) may also be used to prepare the macrocycle.

In particular embodiments, the second reagent comprises a compound of Formula (11):

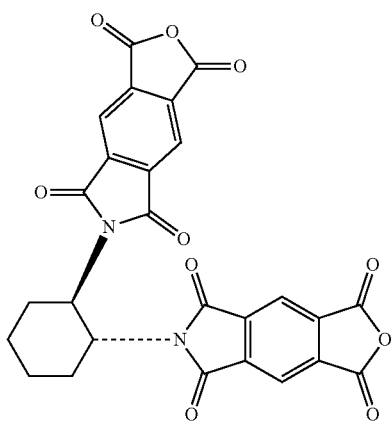 [SMILES: O=c1oc(=O)c2cc3c(=O)n([C@@H]4CCCC[C@H]4n4c(=O)c5cc6c(=O)oc(=O)c6cc5c4=O)c(=O)c3cc12]

or a compound of Formula (12)

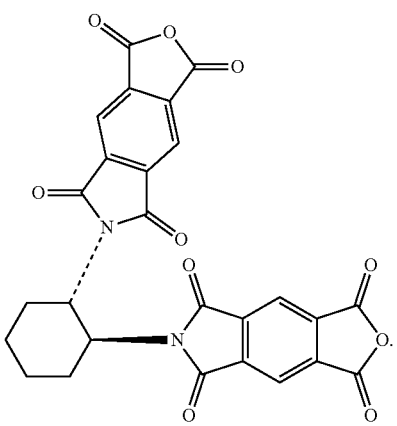 [SMILES: O=c1oc(=O)c2cc3c(=O)n([C@H]4CCCC[C@@H]4n4c(=O)c5cc6c(=O)oc(=O)c6cc5c4=O)c(=O)c3cc12]

Derivative of either of Formulas (11) or (12) may also be used to prepare the macrocycle.

Compounds of Formulas (11) or (12) as well as derivatives of either Formulas (11) or (12) may be cyclocondensed with a compound of Formula (13)

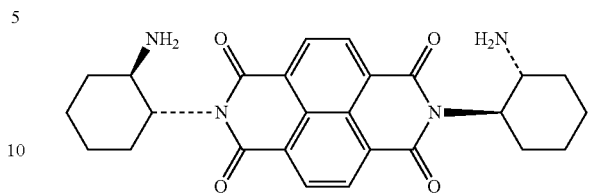

or a compound of Formula (14)

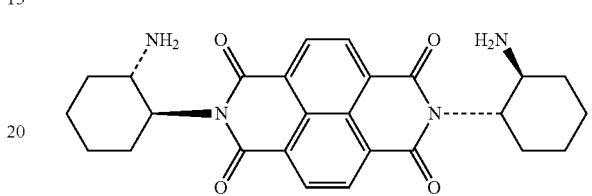

Derivative of either of Formulas (13) or (14) may also be used to prepare the macrocycle.

The macrocycles disclosed herein, may be used to prepare cathodic materials, cathodes, and batteries. These cathodic materials, cathodes, and batteries may comprise any of the rigid macrocycles described here, including, without limitation a macrocycle comprising a compound of Formulas (3), (4), (5), or (6) and any derivatives a compound of Formulas (3), (4), (5), or (6). Derivatives of the compounds of Formulas (3), (4), (5), or (6) also include lithiated derivatives. In some embodiments, the cathode material is lithiated.

The cathodic materials may further comprise a binder material and an electron-conducting material. In some embodiments, the cathode material further comprises a solvent.

In some embodiments, the macrocycle is 1-90 wt % (e.g., 1 wt %, 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, 15 wt %, 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, 90 wt %, or any ranges therebetween) of the cathodic material. In some embodiments, the macrocycle is 5-85 wt %, 10-80 wt %, 20-80 wt %, 40-70 wt %, etc. of the cathode material.

In some embodiments, the binder material comprises a polymer selected from the group consisting of: styrene-butadiene rubber (SBR); polyvinylidene fluoride (PVDF); polytetrafluoroethylene (PTFE); copolymer of tetrafluoroethylene, hexafluoropropylene, and vinylidene fluoride; copolymer of hexafluoropropylene and vinylidene fluoride; copolymer of tetrafluoroethylene and perfluorinated vinyl ether; methyl cellulose; carboxymethyl cellulose; hydroxymethyl cellulose; hydroxyethyl cellulose; hydroxypropylcellulose;

carboxymethylhydroxyethyl cellulose; nitrocellulose; colloidal silica; and combinations thereof. In some embodiments, binder material comprises PVDF. In some embodiments, the binder material is 1-25 wt % (e.g., 1 wt %, 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, 15 wt %, 20 wt %, 25 wt %, or any ranges therebetween) of the cathodic material. In some embodiments, the binder material is 5-15 wt % of the cathode material.

In some embodiments, the solvent comprises N-methylpyrrolidone (NMP).

In some embodiments, the electron-conducting additive is a carbon or graphitic material. In some embodiments, the carbon or graphitic material is selected from the list consisting of: a graphite, a carbon black, a graphene, and a carbon nanotube. In some embodiments, the carbon or graphitic material is a graphite selected from the group consisting of: graphite worms, exfoliated graphite flakes, and expanded graphite. In some embodiments, the carbon or graphitic material is chemically-etched or expanded soft carbon, chemically-etched or expanded hard carbon, or exfoliated activated carbon. In some embodiments, the carbon or graphitic material is a carbon black selected from the group consisting of: acetylene black, channel black, furnace black, lamp black thermal black, chemically-etched or expanded carbon black, and combinations thereof. In some embodiments, the carbon or graphitic material is a carbon nanotube selected from the group consisting of: chemically-etched multi-walled carbon nanotube, nitrogen-doped carbon nanotube, boron-doped carbon nanotube, chemically-doped carbonnanotube, ion-implanted carbon nanotube, and combinations thereof. In some embodiments, the electron-conducting additive comprises carbon black. In some embodiments, the electron-conducting additive is 1-99 wt % (e.g., 1 wt %, 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, 15 wt %, 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, 90 wt %, 91 wt %, 92 wt %, 93 wt %, 94 wt %, 95 wt %, 96 wt %, 97 wt %, 98 wt %, 99 wt %, or any ranges therebetween) of the cathode material. In some embodiments, the electron-conducting additive is 5-85 wt % of the cathode material.

In some embodiments, the cathodic material is present as a slurry. In some embodiments, the slurry comprises a solid content of 40-80% 40 wt %, 45 wt %, 50 wt %, 55 wt %, 60 wt %, 65 wt %, 70 wt %, 75 wt %, 80 wt %, or any ranges therebetween).

In some embodiments, the cathodic material is dried (e.g., solvent evaporated out of a slurry). In some embodiments, the cathodic material is dried under increased heat (e.g., above room temperature (e.g., 40° C., 50° C., 60° C., 70° C., 80° C., 90° C., 100° C., 110° C., 120° C., 130° C., 140° C., 150° C.,), reduced pressure (e.g., below atmospheric pressure, under vaccum), etc. In some embodiments, provided herein are cathodes comprising a cathode material described herein. In some embodiments, a cathode further comprises a foil substrate. In some embodiments, the foil substrate is an aluminum foil substrate. In some embodiments, a slurry comprising the cathode material is coated onto the foil substrate and dried.

In some embodiments provided herein are batteries comprising a cathode described herein. In some embodiments, a battery described herein is rechargeable. In some embodiments, provided herein are methods of storing energy within a batter described herein.

The battery may further comprise an anode. In some embodiments, an anode comprises: (a) a graphite or other carbon-based active material; (b) a binder material; (c) an electron-conducting additive; and (e) a substrate. In some embodiments, an anode further comprises a solvent. In some embodiments, the binder material, electron-conducting additive, and/or solvent of the anode are selected from the binder materials, electron-conducting additives, and/or solvents described herein for use in cathodes. In some embodiments, the anode comprises a lithium active material rather than a graphite or other carbon-based active material. In some embodiments, the graphite or other carbon-based active material of the anode is lithiated.

In some embodiments, a battery further comprises a separator. In some embodiments, the separator comprises polypropylene (PP), polyethylene (PE), or a combination of layers thereof.

In some embodiments, a battery further comprises an electrolyte material. In some embodiments, the electrolyte material comprises NiCd, NiMH, Li-ion, Li-ion polymer, lead acid, and/or alkaline. In some embodiments, the electrolyte material comprises Lithium ions. In some embodiments, the electrolyte material comprises non-coordinating anion salts such as lithium hexafluorophosphate ($LiPF_6$), lithium hexafluoroarsenate monohydrate ($LiAsF_6$), lithium perchlorate ($LiClO_4$), lithium tetrafluoroborate ($LiBF_4$), and/or lithium triflate ($LiCF_3SO_3$). In some embodiments, the electrolyte material further comprises a mixture of organic carbonates. In some embodiments, the mixture of organic carbonates comprises ethylene carbonate and/or diethyl carbonate.

In some embodiments, provided herein are methods of preparing a cathode material comprising a macrocycle described herein; methods of preparing a cathode comprising said cathode material; methods of preparing a battery comprising said cathode; and methods of preparing a device comprising said battery.

In some embodiments, provided herein are systems, compositions, and devices comprising oganic capacitors, super capacitors, organic dopants, redox-active charge carriers, photovoltaics, solar cells, organic thin-film semiconductors, etc. comprising a macrocycle described herein.

Figure 1B:
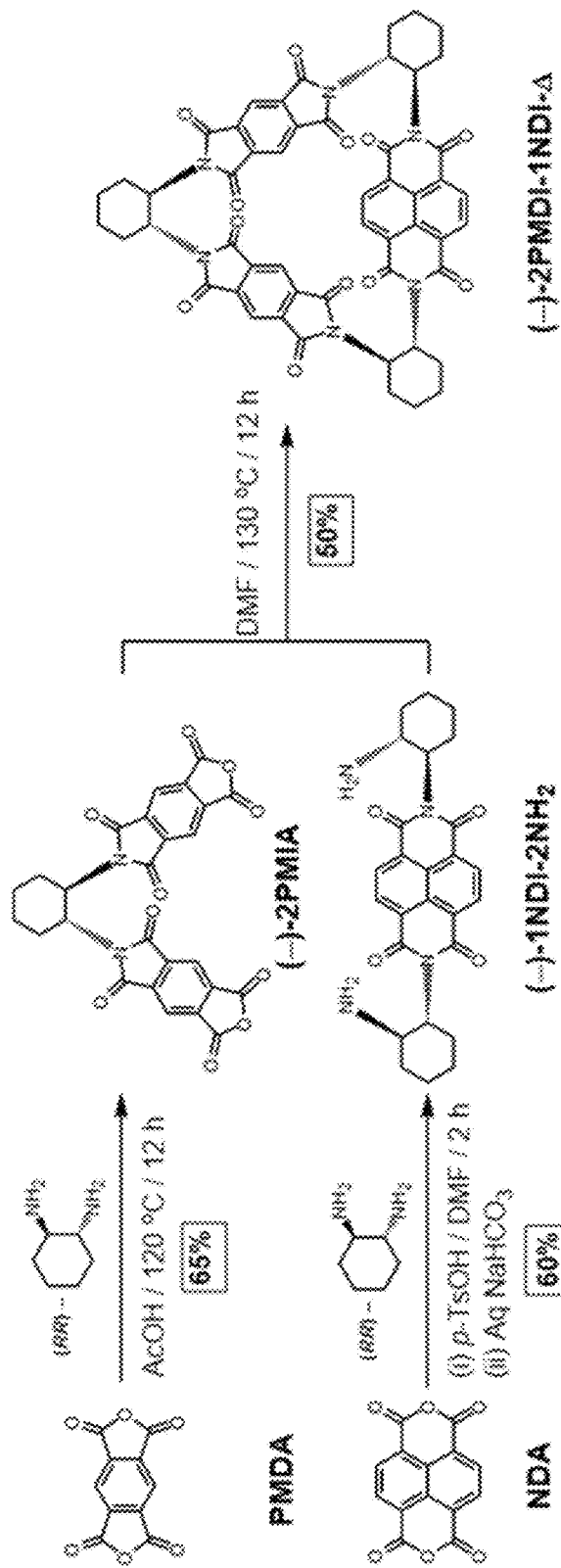
FIG. 1B shows a stereospecific stepwise preparation of chiral isosceles triangle (−)-2PMDI-1NDI-Δ from (RR)-trans-1,2-cyclohexanediamine, naphthalenetetra-carboxylic dianhydride (NDA) and pyromellitic dianhydride (PMDA).
Figure 1C:
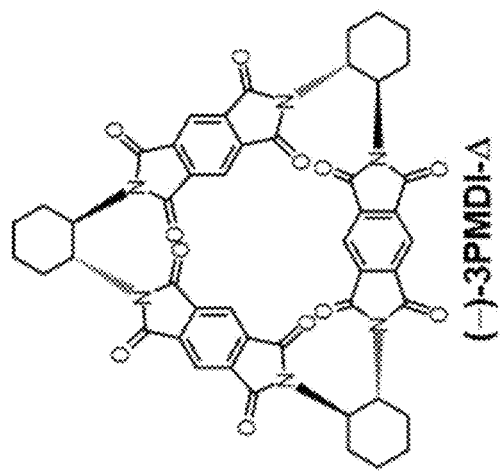
FIG. 1C shows structural formulas of the monomeric reference compounds (Ref-NDI and Ref-PMDI) and the chiral equilateral triangles [(−)-3NDI-Δ and (−)-3PMDI-Δ].
Figure 1C:
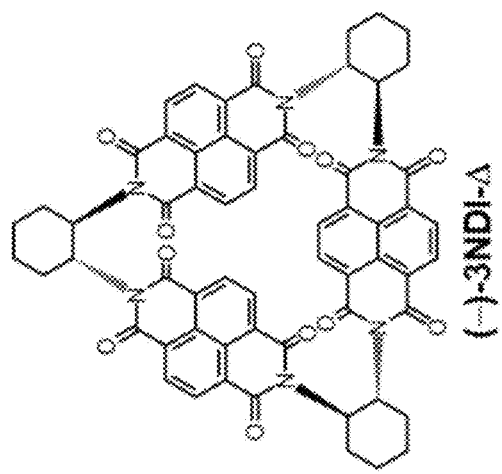
Figure 1C:
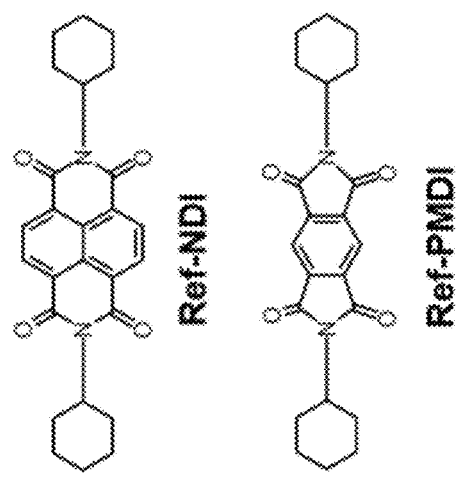

As further described in the Examples, two chiral isosceles triangles were prepared by stepwise condensations between commercially available (RR)-trans-1,2-cyclohexanediamine and two different dianhydride derivatives—namely, naphthalenetetracarboxylic dianhydride (NDA) and pyromellitic dianhydride (PMDA). The condensation between (RR)-trans-1,2-cyclohexanediamine and a five-fold excess of either NDA or PMDA in either DMF or acetic acid gave (FIGS. 1A and 1B) the corresponding dimers—namely, (−)-2NIA and (−)-2PMIA, respectively, in 60-65% yield. The condensation of 2 equiv of (RR)-trans-1,2-cyclohexanediamine with 1 equiv of either NDA or PMDA in the presence of 2 equiv of p-TsOH in DMF or acetic acid gave the corresponding ditosylates of (−)-1NDI-$2NH_2$ and (−)-1PMDI-$2NH_2$, respectively. The subsequent extraction of these salts with a saturated aqueous $NaHCO_3$ solution afforded (FIGS. 1A and 1B) the diamines (−)-1NDI-$2NH_2$ and (−)-1PMDI-$2NH_2$ in 60-65% yield. Macrocyclizations were carried out in DMF at 130° C. by the cyclocondensation of 1 equiv of (−)-2NIA with 1 equiv of (−)-1PMDI-$2NH_2$ afforded the desired isosceles triangle (−)-1PMDI-2NDI-Δ in 50% yield, while the cyclocondensation of 1 equiv of (−)-2PMIA with 1 equiv of (−)-1NDI-$2NH_2$ afforded (FIGS. 1A and 1B) the desired isosceles triangle (−)-2PMDI-1NDI-Δ in 50% yield. Characterization of both (−)-1PMDI-2NDI-Δ and (−)-2PMDI-1NDI-Δ was achieved by electrospray ionization high-resolution mass spectrometry (ESI-HRMS) which confirmed the presence of the species $[M+H]^+$ in the gas phase at m/z=989.2779 and 939.2607, respectively.

Figure 2A:
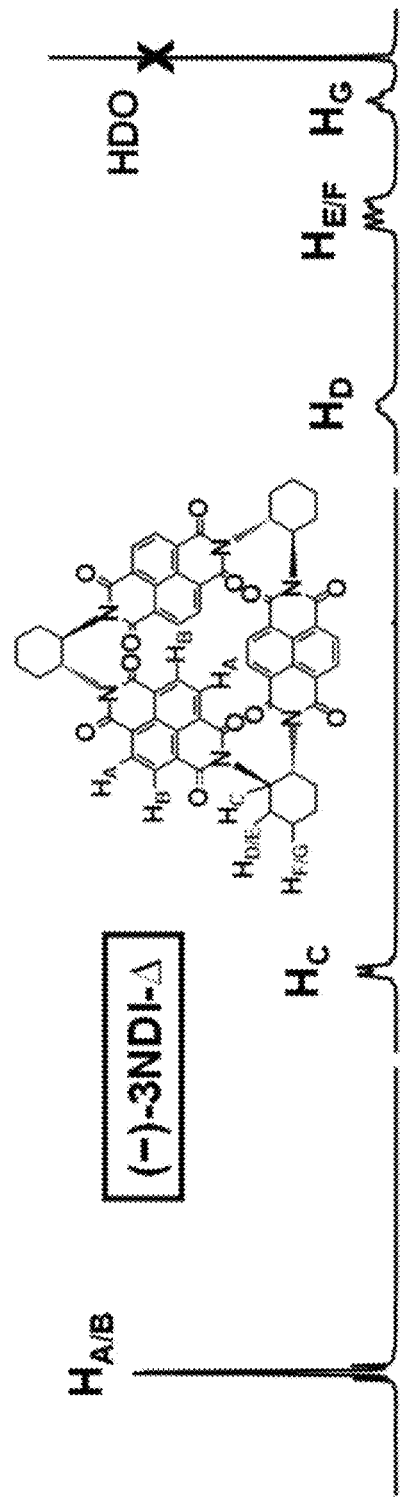
FIG. 2A shows a comparison of the annotated $^1$H NMR spectra (500 MHz, CDCl$_3$, 298 K) of the molecular triangle (−)-3NDI-Δ.
Figure 2B:
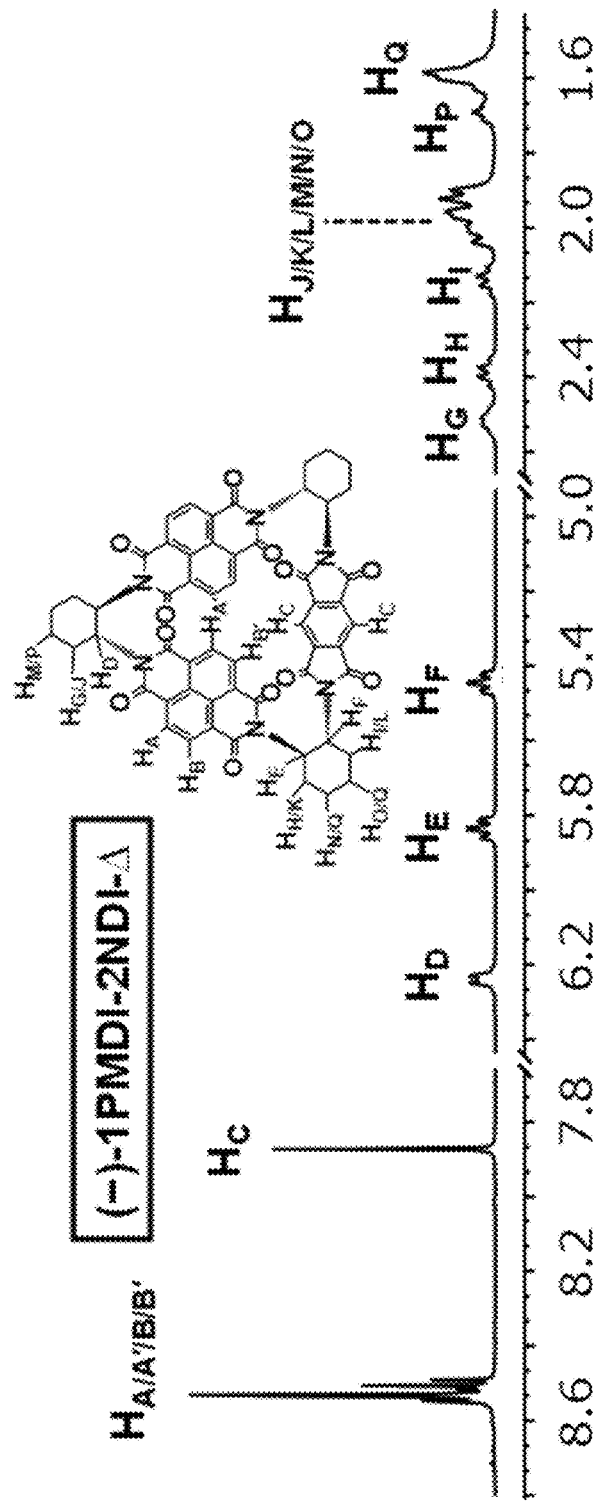
FIG. 2B shows a comparison of the annotated $^1$H NMR spectra (500 MHz, CDCl$_3$, 298 K) of the molecular triangle (−)-1PMDI-2NDI-Δ.
Figure 2E:
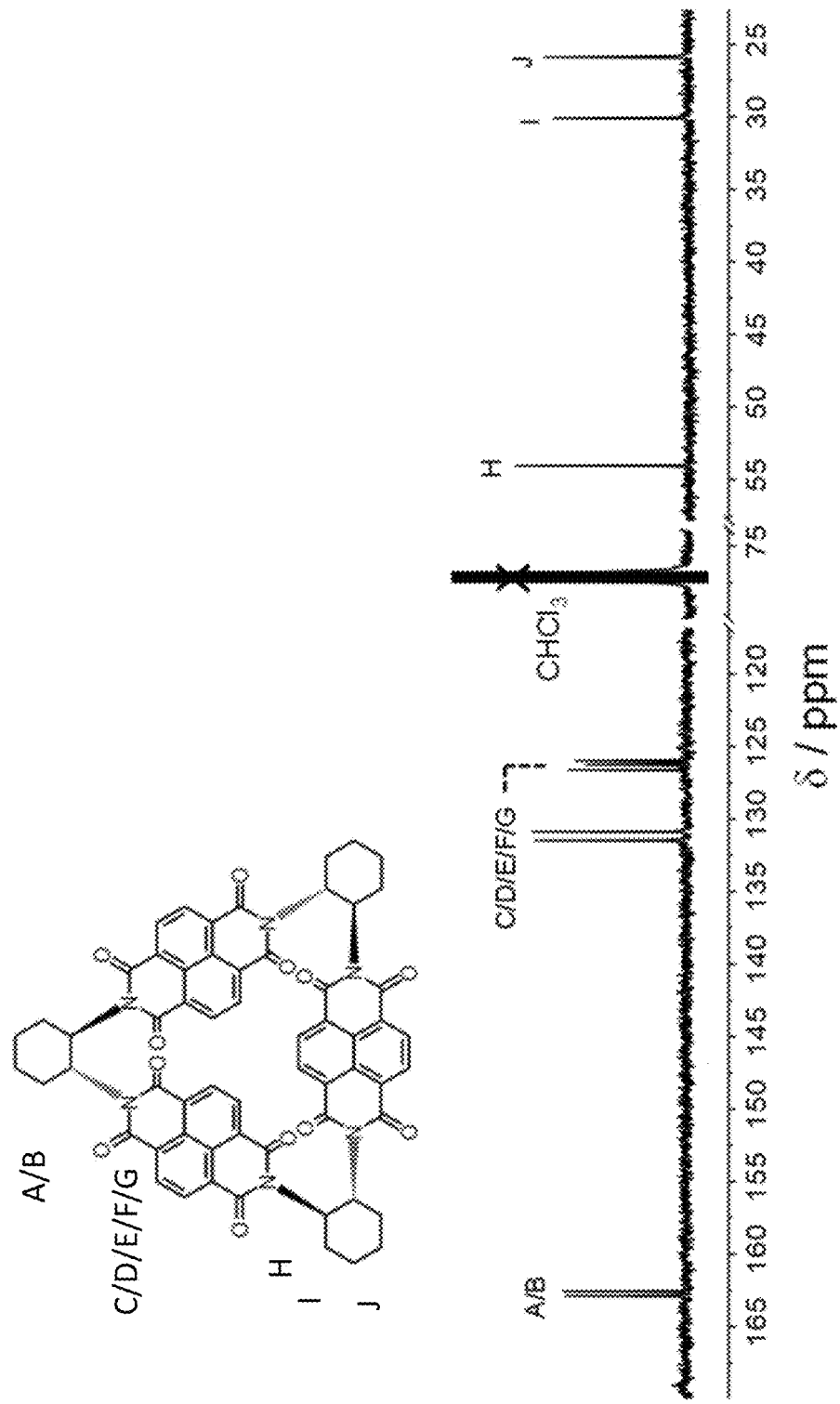
FIG. 2E shows a comparison of the annotated $^{13}$C NMR spectra (125 MHz, CDCl$_3$, 298 K) of (−)-3NDI-Δ.
Figure 2F:
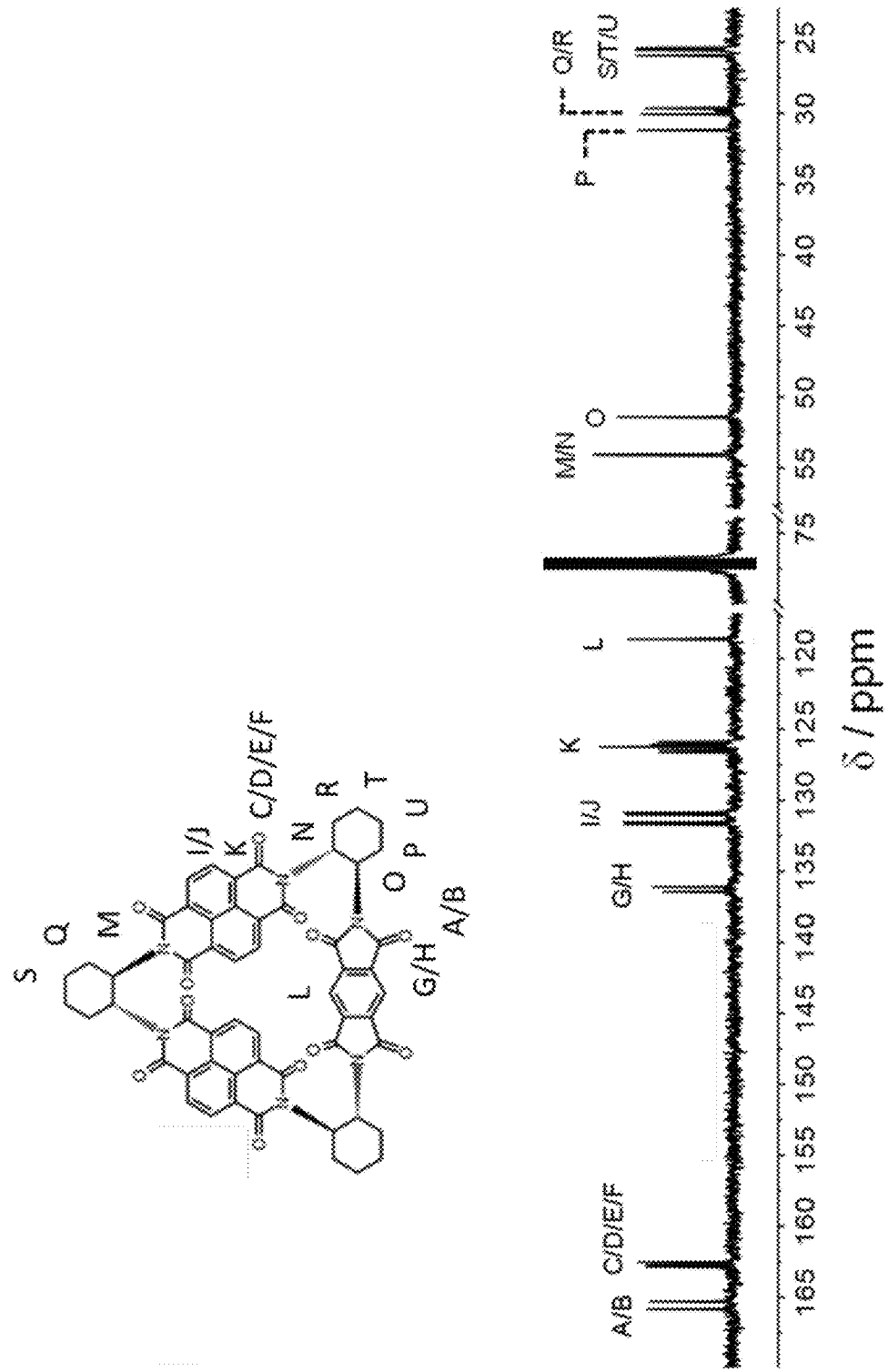
FIG. 2F shows a comparison of the annotated $^{13}$C NMR spectra (125 MHz, CDCl$_3$, 298 K) of (−)-1PMDI-2NDI-Δ.
Figure 2G:
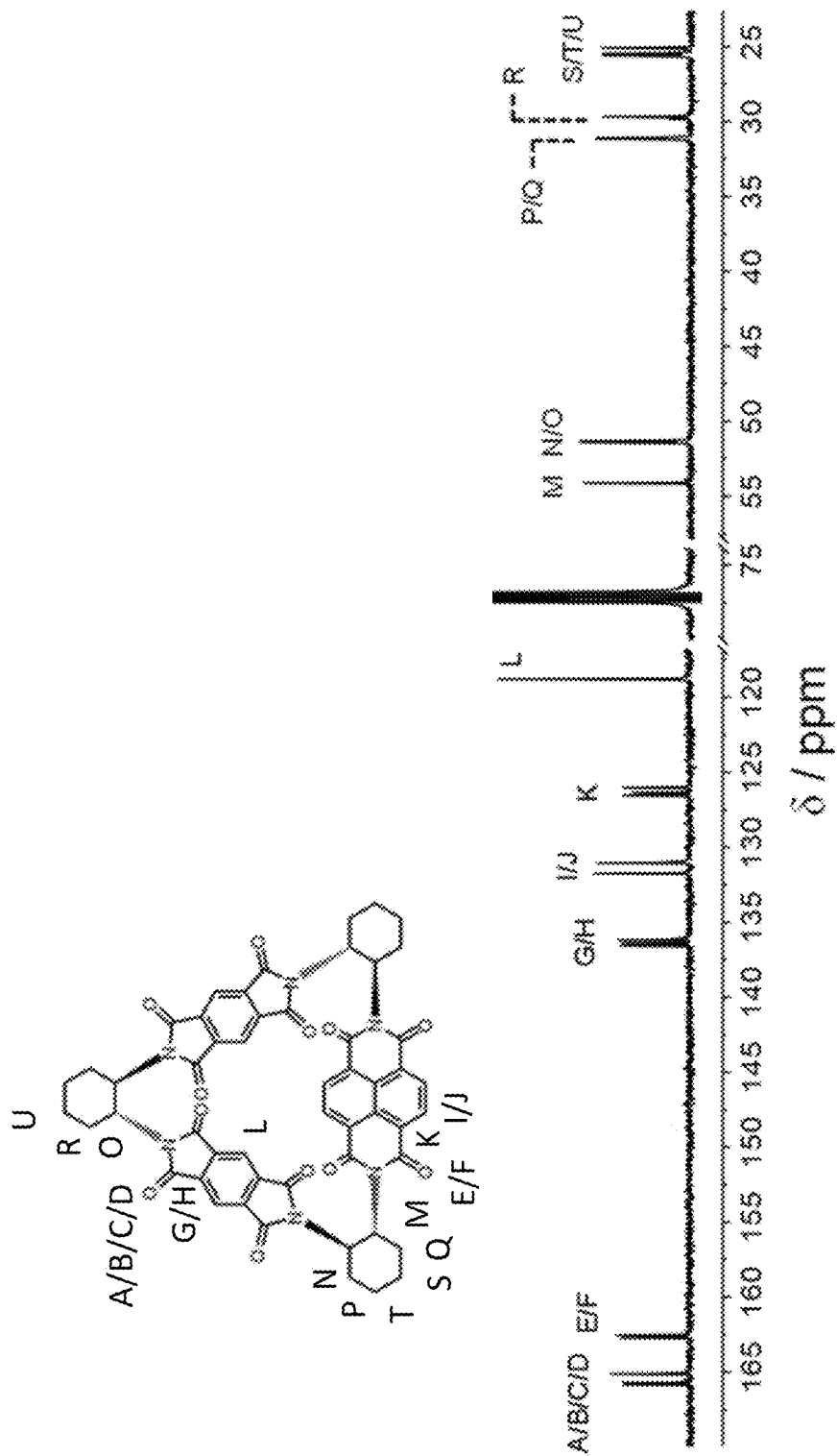
FIG. 2G shows a comparison of the annotated $^{13}$C NMR spectra (125 MHz, CDCl$_3$, 298 K) of (−)-2PMDI-1NDI-Δ.
Figure 2H:
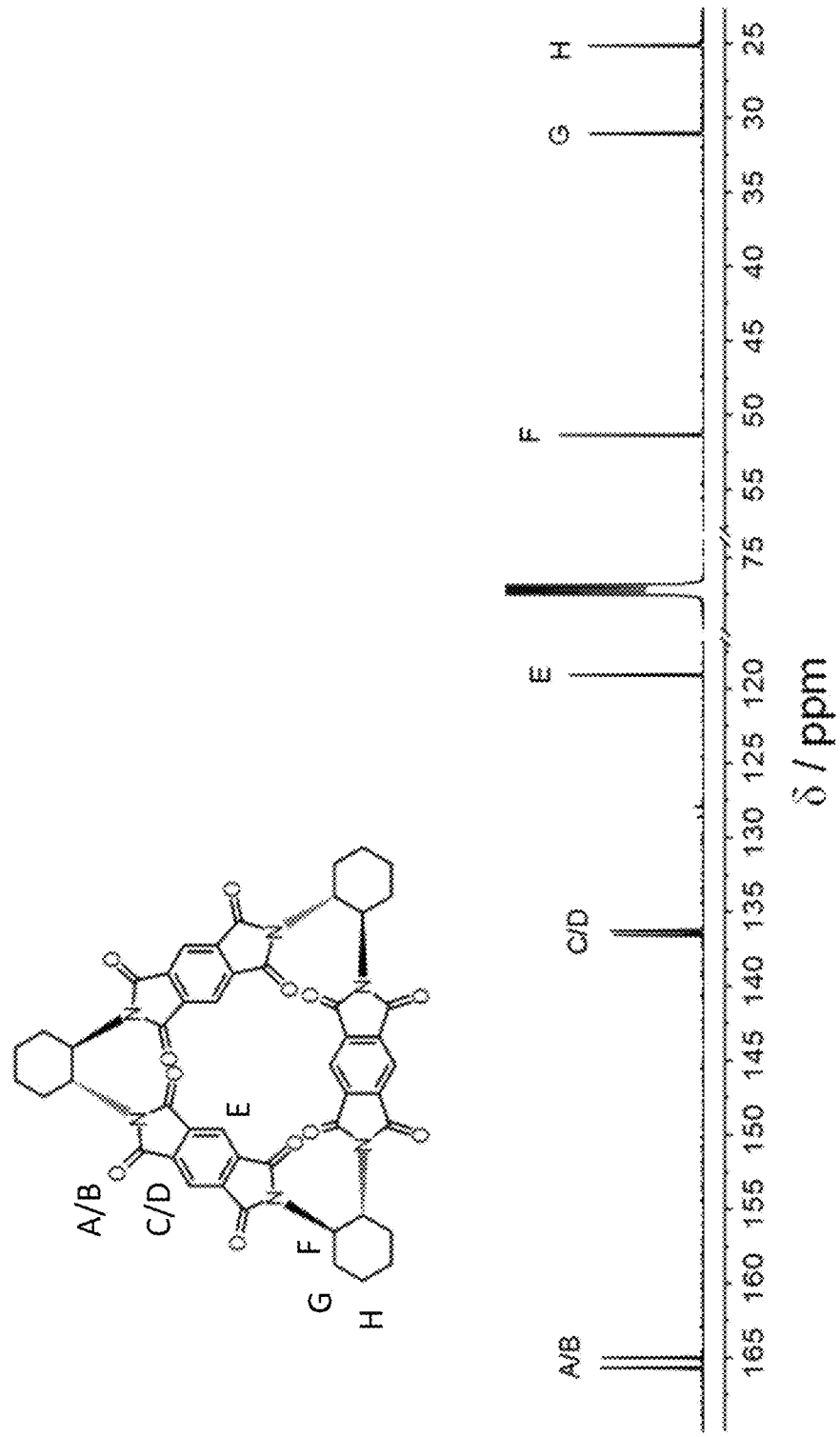
FIG. 2H shows a comparison of the annotated $^{13}$C NMR spectra (125 MHz, CDCl$_3$, 298 K) of (−)-3PMDI-Δ.
Figure 3:
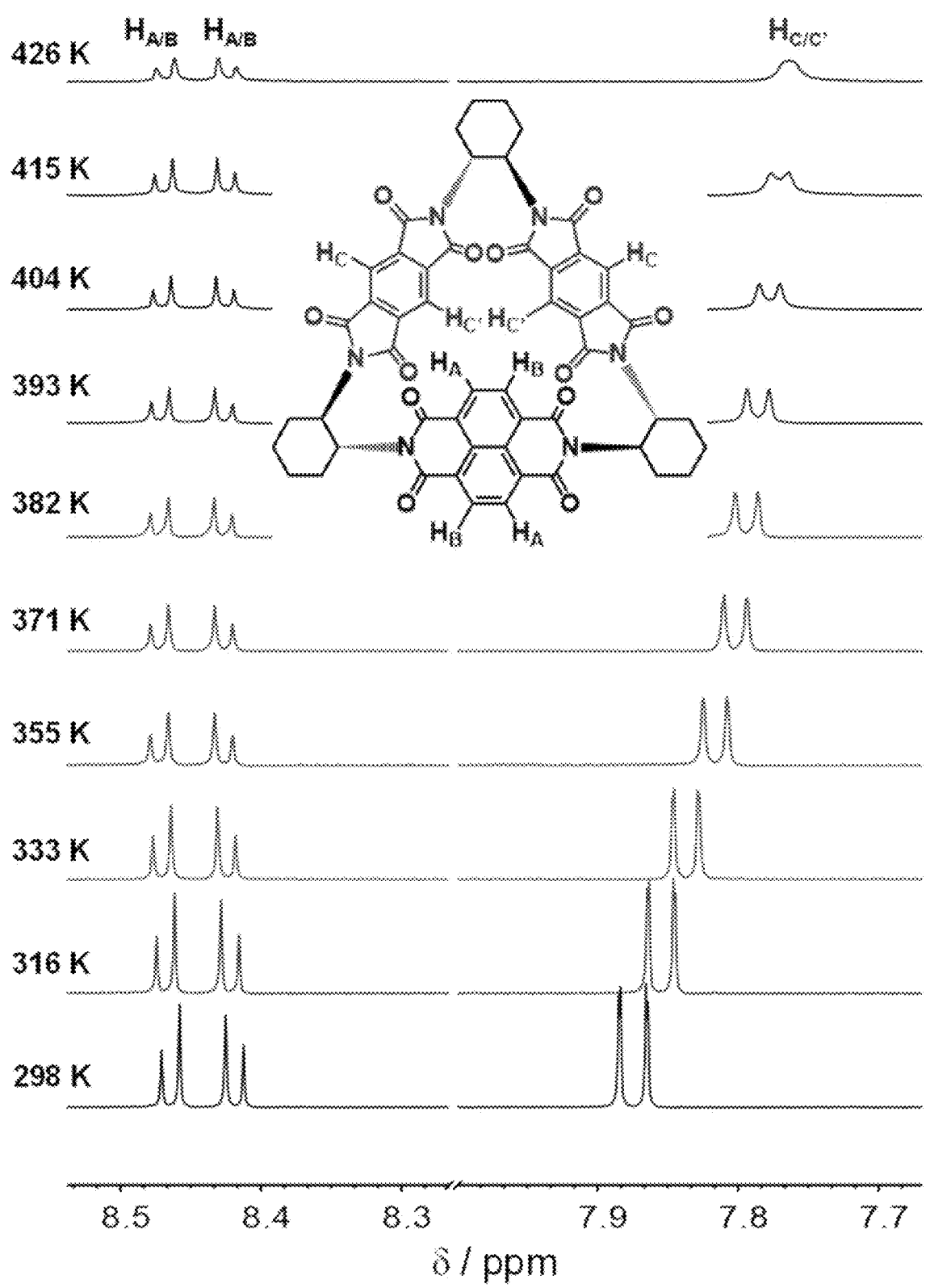
FIG. 3 shows variable temperature $^1$H NMR spectra (600 MHz, CD$_3$SOCD$_3$) in the aromatic region of the isosceles triangle (−)-2PMDI-1NDI-Δ. The coalescence temperature of the resonances for the PMDI protons (H$_C$ and H$_{C'}$) is observed at 426 K.

$^1$H NMR Spectra (FIG. 2) of (−)-1PMDI-2NDI-Δ and (−)-2PMDI-1NDI-Δ recorded in $CDCl_3$ display characteristic resonances for the protons of both the NDI and PMDI subunits in the downfield regions with δ=8.2-9.0 and 7.8-8.2 ppm, respectively, as well as the aliphatic methine (CH) and methylene (CH$_2$) protons of the cyclohexane-linkers in the upfield regions with δ=3.0-6.5 and 1.5-3.0 ppm, respectively. In particular, $^1$H NMR spectrum of (−)-1PMDI-2NDI-Δ shows (FIG. 2B) four sets of signals for the 8 NDI protons and only one singlet for the 2 PMDI protons, while that of (−)-2PMDI-1NDI-Δ shows (FIG. 2C) two sets of signals for the 4 NDI protons and two doublets for the 4 PMDI protons. At higher field, three sets of signals were observed for the six methine protons in both (−)-1PMDI-2NDI-Δ and (−)-2PMDI-1NDI-Δ. A comparison of the $^1$H NMR spectra (FIGS. 2A-2D), along with $^{13}$C NMR spectra (FIGS. 2E-2H), of this series of triangles confirms the lower symmetry (C$_2$ point group) of the isosceles triangles (−)-1PMDI-2NDI-Δ and (−)-2PMDI-1NDI-Δ in comparison to the equilateral triangles (−)-3NDI-Δ and (−)-3PMDI-Δ belonging to the D$_3$ point group. Furthermore, variable temperature $^1$H NMR was performed (FIG. 3) on (−)-2PMDI-1NDI-Δ to evaluate the rates of rotation of the PMDI and NDI units around the C—N . . . N—C bond axis of the isosceles triangle. At higher temperatures, coalescence of the two doublets into one broad signal was observed for the PMDI protons (H$_C$ and H$_{C'}$). The free energy of activation at the coalescence temperature (426 K) was calculated to be 23 kcal mol$^{-1}$.

Figure 4B:
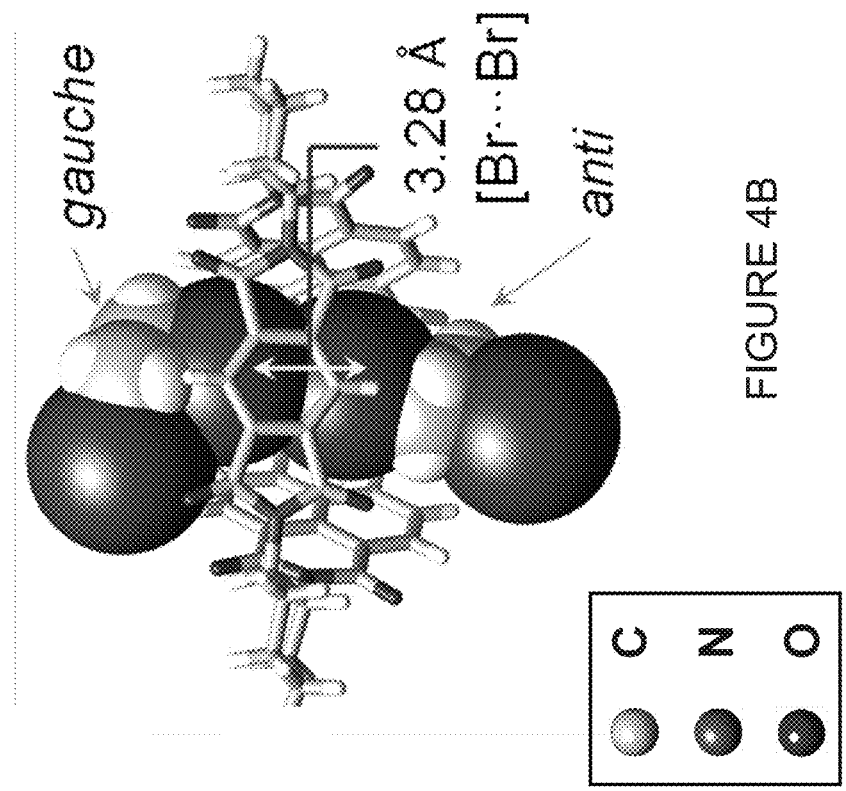
FIG. 4B shows a solid-state (super)structures of (−)-1PMDI-2NDI-Δ in a side-on view of the inclusion complex formed between (−)-1PMDI-2NDI-Δ and two [Br . . . Br]-bonded 1,2-dibromoethane which are depicted in space-filling representations.
Figure 4A:
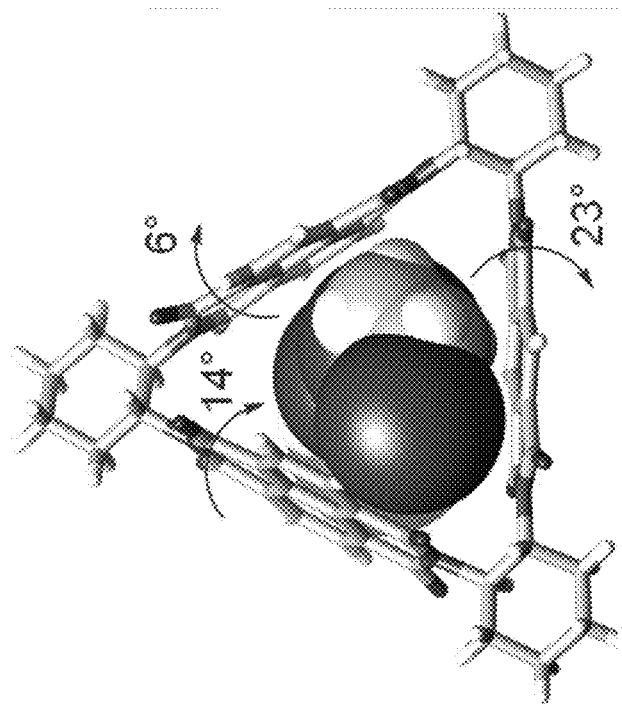
FIG. 4A shows a solid-state (super)structures of (−)-1PMDI-2NDI-Δ in a plane view of the inclusion complex formed between (−)-1PMDI-2NDI-Δ and two [Br . . . Br]-bonded 1,2-dibromoethane which are depicted in space-filling representations.
Figures 4C, 4D:
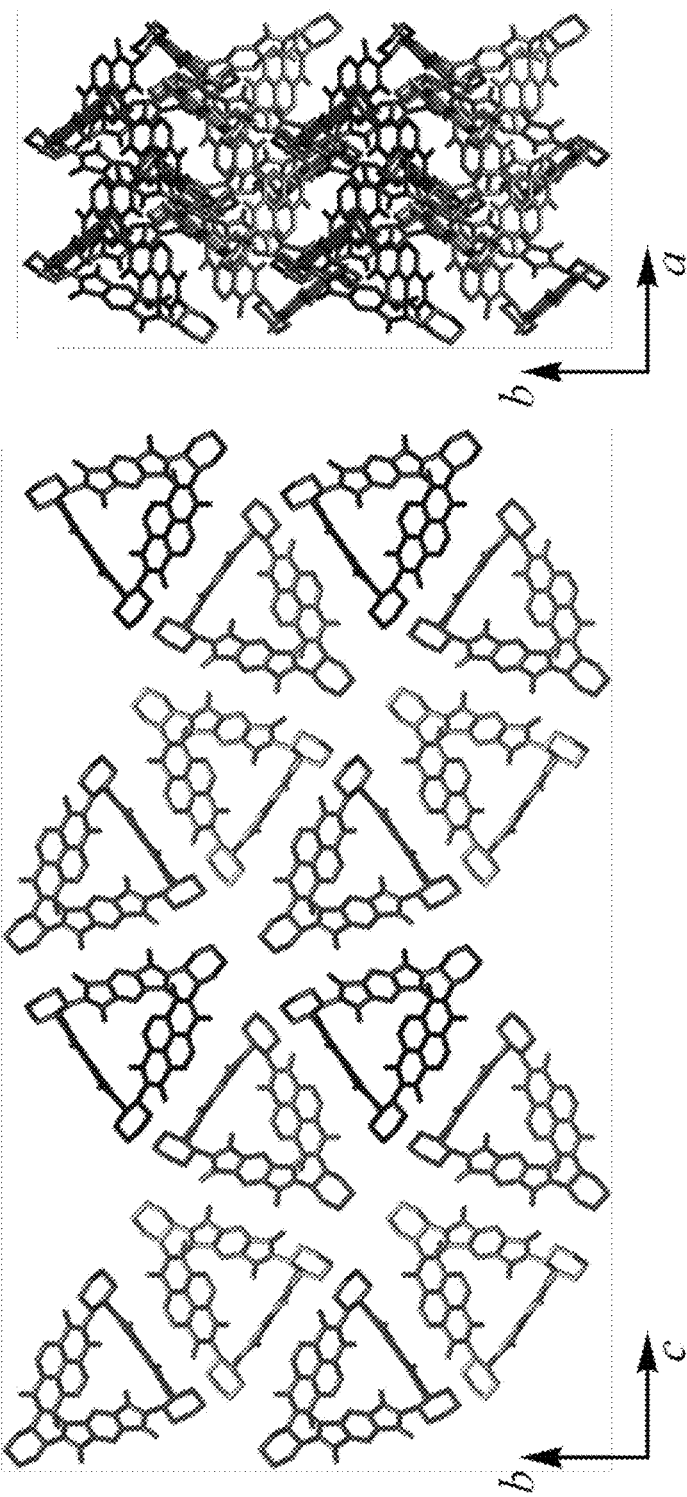
FIG. 4C shows a first view of the packing superstructure of (−)-1PMDI-2NDI-Δ, where the 1,2-dibromoethane molecules and H atoms are omitted for the sake of clarity.
FIG. 4D shows a second view of the packing superstructure of (−)-1PMDI-2NDI-Δ, where the 1,2-dibromoethane molecules and H atoms are omitted for the sake of clarity.
Figure 4E:
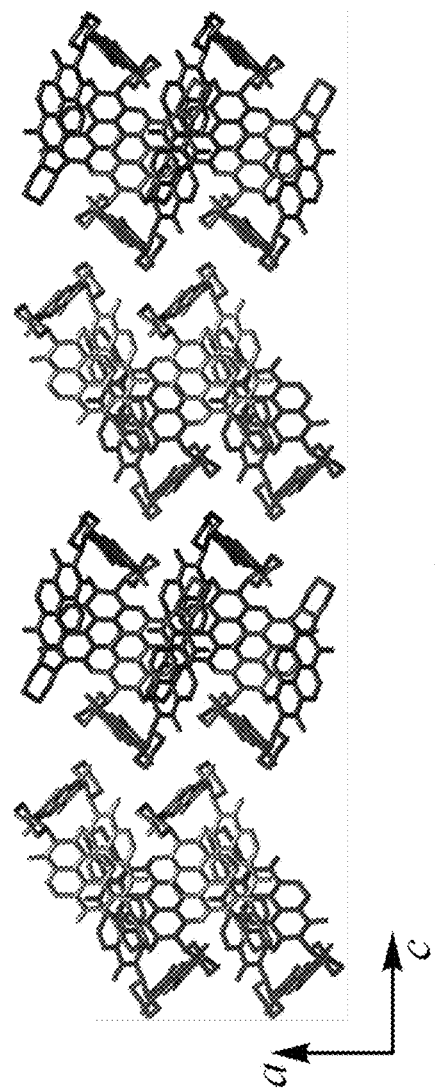
FIG. 4E shows a third view of the packing superstructure of (−)-1PMDI-2NDI-Δ, where the 1,2-dibromoethane molecules and H atoms are omitted for the sake of clarity.
Figure 5A:
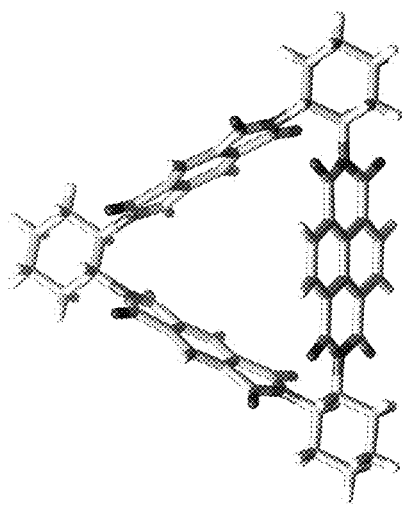
FIG. 5A shows a solid-state (super)structures of (−)-2PMDI-1NDI-Δ in a tubular representation.
Figure 5B:
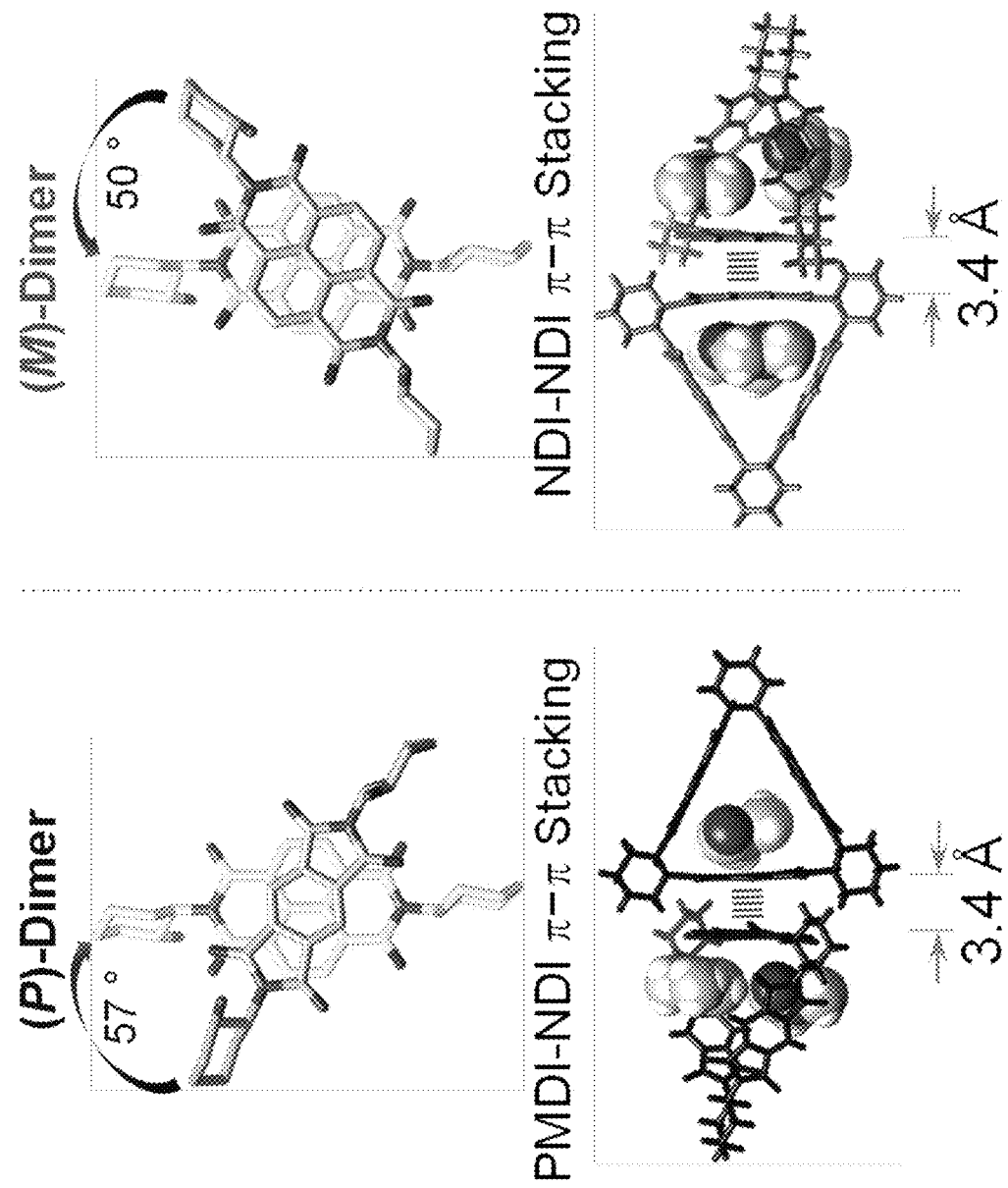
FIG. 5B shows two different types of nn stacking dimers [(P)- and (M)-Dimers] exhibiting opposite supramolecular helicities: the NDI and PMDI moieties not involved in π-π stacking are omitted for the sake of clarity (top) and the location of DMF molecules inside the triangles and the π-π stacking of NDINDI as well as PMDINDI (bottom).
Figure 5D:
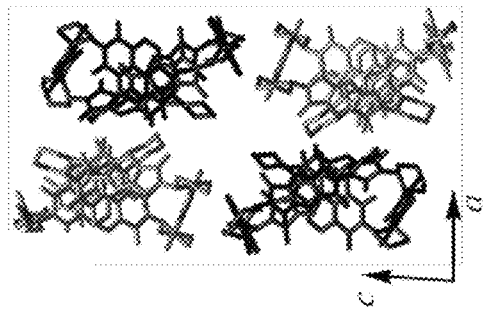
FIG. 5D shows a side-on view of the superstructure of both the (P)- and (M)-Dimers. Hatched lines indicate the π-π stacking interactions between the aromatic subunits.
Figure 5C:
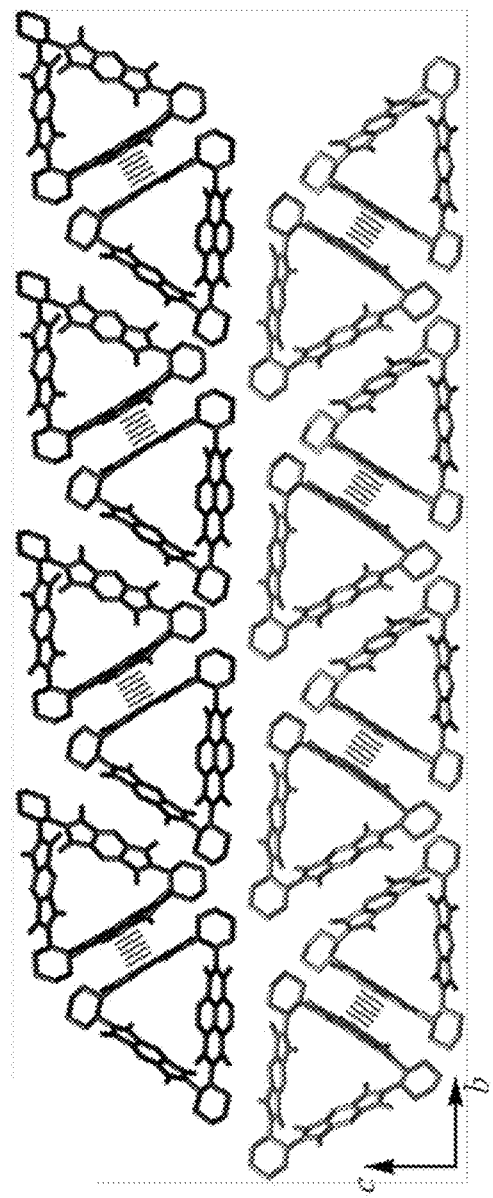
FIG. 5C shows a plan view of the superstructure of both the (P)- and (M)-Dimers. Hatched lines indicate the π-π stacking interactions between the aromatic subunits.

In order to gain more insight into the structural details of (−)-1PMDI-2NDI-Δ and (−)-2PMDI-1NDI-Δ, we performed single-crystal X-ray diffraction analyses (FIGS. 4 and 5) on the crystals obtained (i) by slow vapor diffusion of n-hexane into a 3.0 mM solution of (−)-1PMDI-2NDI-Δ in 1,2-dibromoethane (DBE) and (ii) by slow vapor diffusion of H$_2$O into a 5.0 mM solution of (−)-2PMDI-1NDI-Δ in DMF over the course of 3 days. The solid-state (super) structure (FIG. 4) of (−)-1PMDI-2NDI-Δ reveals the rigid geometries of the triangular hollow prism in which the tilt angles of the PMDI (23°) and the two NDI subunits (6 and 14°) are much greater than those of three NDI subunits (~3°) in the equilateral triangle (−)-3NDI-Δ. This observation indicates that the less bulky PMDI unit facilitates the tilting of all three π-surfaces. In striking contrast to the tubular superstructure of (−)-3NDI-Δ in DBE, that of (−)-1PMDI-2NDI-Δ in DBE reveals (FIGS. 4C-4E) neither columnar stacking of the triangular units to form one-dimensional (1D) nanotubes nor π-π stacking between two NDI units or PMDI and NDI units. Although the cavity of (−)-1PMDI-2NDI-Δ is penetrated (FIGS. 4A-4B) by two [Br . . . Br]-bonded (3.28 Å) DBE molecules which are stabilized by [Br . . . π] interactions (~3.5 Å) with π-surfaces, only one DBE molecule is in anti-conformation and the other is in the gauche-conformation (FIG. 4B), which prohibits the formation of continuous 1D [Br . . . Br]-bonded solvent chains that would template the formation of the nanotubes. The replacement of the NDI subunits with PMDI ones within the triangle also breaks the complementarity of [C—H . . . O] interactions between two triangles, a situation which is crucial for their columnar stacking.

Although we were unable to obtain suitable single crystals of (−)-2PMDI-1NDI-Δ from DBE/n-hexane for X-ray diffraction analysis, the compound did crystallize from the aqueous DMF system. The solid-state structure of (−)-2PMDI-1NDI-Δ reveals (FIG. 5A) a similar rigid triangular geometry. Among the three of four asymmetric units in the unit cell, one or two DMF molecules are bound (FIG. 5B) to their cavities by means of very short π-π overlap (~3.0 Å) between the amide groups of DMF and the NDI planes. Much to our surprise, these four isosceles triangles assemble (FIG. 5B) into two types of π-π stacking supramolecular dimers—(i) (P)-helical dimer ((P)-Dimer) with a right-twisted angle of 57° formed through π-π stacking (3.4 Å) between the DMF-bound NDI plane of one triangle and a PMDI plane of another triangle, and (ii) (M)-helical dimer ((M)-Dimer) with a left-twisted angle of 50° formed through π-π stacking (3.4 Å) between DMF-bound NDI planes of another two triangles. It is worth noting that prior to this work, π-π stacking between NDI units of molecular triangles had been observed only in the cases of hostguest complexes [I$_3^-$ ⊂ 3NDI-Δ] of 3NDI-Δ with I$_3^-$ and the radical anion [(−)-3NDI-Δ]$^{·-}$ of (−)-3NDI-Δ on account of the increase in the electron density of the neutral NDI unit as a result of anion binding and reduction, respectively. In the case of (−)-2PMDI-1NDI-Δ, it appears that DMF acts in a role similar to that of I$_3^-$ in increasing the electron density of the NDI unit through very short π-π stacking which favors the π-π stacking of another facet of the NDI unit with the other π-plane. The helicity of supramolecular assembles are determined predominantly by the chirality of the chiral monomer. In the superstructure of (−)-2PMDI-1NDI-Δ, however, the assembly of the homochiral monomers gives rise to two types of dimers with opposite supramolecular helicities. While the (M)-Dimer, formed through NDI-NDI π-π stacking, retains (M)-helicity which is consistent with that observed in the π-π stacking assemblies of (−)-3NDI-Δ, the (P)-Dimer formed through NDI-PMDI π-π stacking shows (P)-helicity. The plausible mechanism for the coexistence of both these dimers can be explained by the fact that the less-bulky PMDI is unable to restrict the effect of the stereogenic centers of the (RR)-trans-1,2-cyclohexano groups for specifically forming the corresponding (M)-helicity. Both (P)- and (M)-Dimers assemble (FIG. 5C) to form 1D tapes along the b-axis, respectively, which then pack (FIG. 5D) alternatively in the a-c plane to form the crystals. Strikingly, both X-ray superstructures of (−)-1PMDI-2NDI-Δ and (−)-2PMDI-1NDI-Δ exhibit a common feature—that is, there is no columnar stacking of either triangle to form 1D nanotubes, an observation which indicates that the breaking of symmetry of the triangles hinders the complementarity of [C—H . . . O] hydrogen bonding interactions between the columnar stacked triangles, and consequently, these observations highlight the necessity of the symmetry of (−)-3NDI-Δ in order to provide complementary [C—H . . . O] interactions for driving the formation of 1D columnar stacking nanotubes.

Figure 6A:
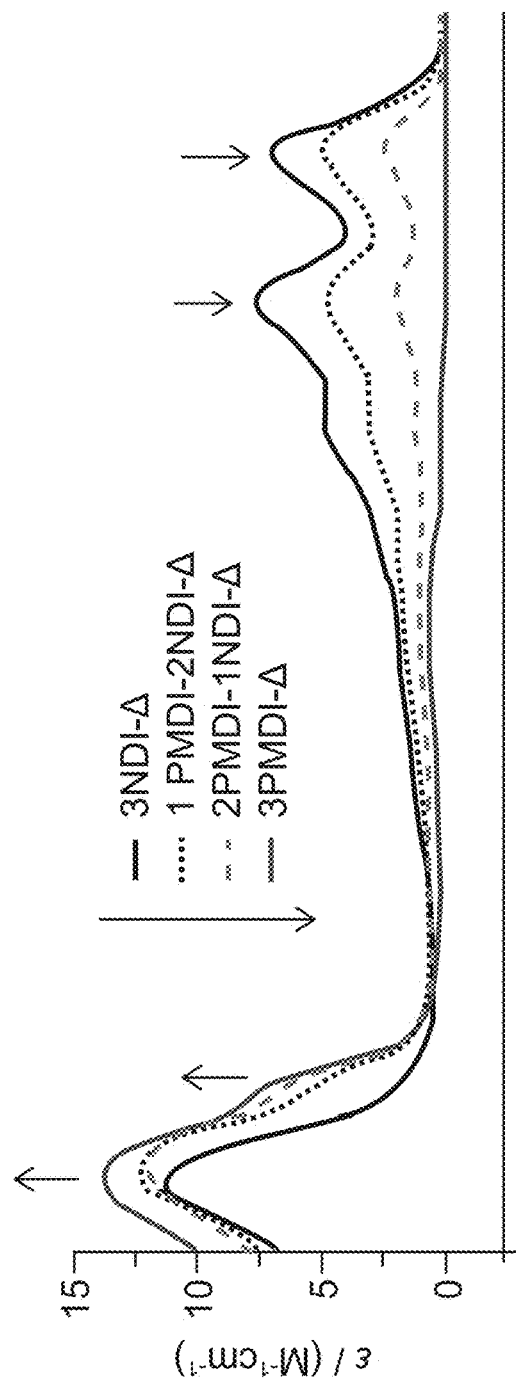
FIG. 6A shows a UV/Vis absorption spectra of (−)-3NDI-Δ, (−)-1PMDI-2NDI-Δ, (−)-2PMDI-1NDI-Δ, and (−)-3PMDI-Δ recorded in CH$_2$Cl$_2$ at 298 K.

The optical properties of all the triangles were investigated (FIG. 6A) by UV/Vis absorption spectroscopy. The comparison of the absorption spectra of this series of triangles suggests that the intensity of the absorption peaks with maxima at 360 and 380 nm decreases gradually on going from (−)-3NDI-Δ to (−)-1PMDI-2NDI-Δ to (−)-2PMDI-1NDI-Δ and eventually disappears in the case of (−)-3PMDI-Δ, in line with the decrease in the number of NDI subunits present in the triangle. This observation is consistent with the characteristic 0←0 and 0←1 vibronic bands corresponding to the S$_1$←S$_0$ electronic transition of the NDI subunits. On the other hand, the intensity of the absorption peaks in the region 225-280 nm rises with the increase in the number of PMDI subunits, an observation which is in good agreement with the characteristic z-polarized π-π* electronic transitions of the PMDI units.

Figure 6B:
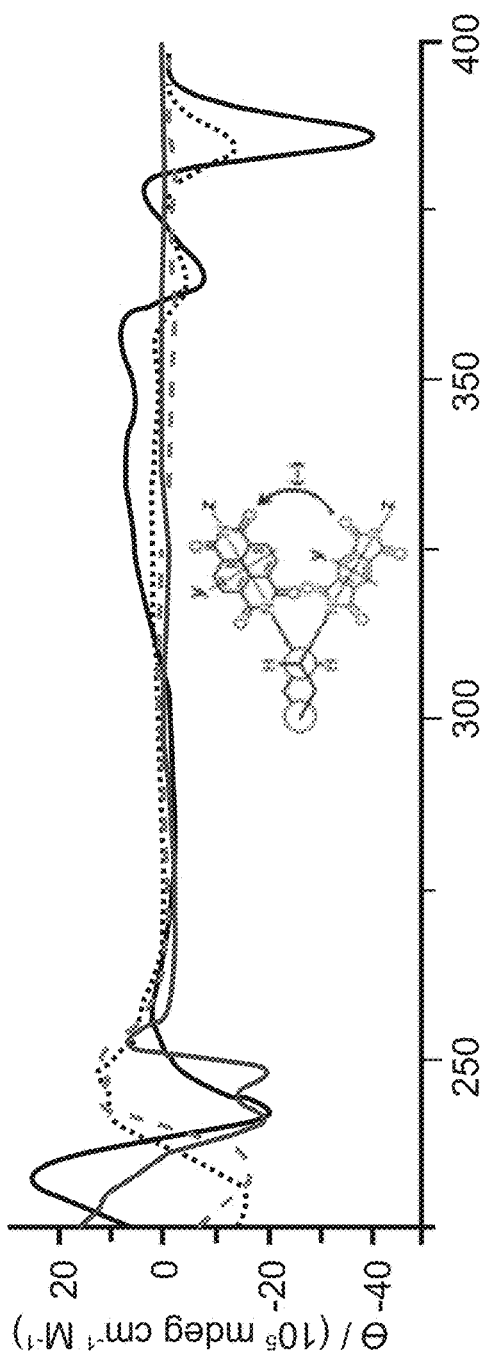
FIG. 6B shows a CD spectra of (−)-3NDI-Δ, (−)-1PMDI-2NDI-Δ, (−)-2PMDI-1NDI-Δ, and (−)-3PMDI-Δ recorded in CH$_2$Cl$_2$ at 298 K.

Circular dichroism (CD) spectroscopy (FIG. 6B) was also performed in order to probe the chiroptical properties and Cotton effects generated by the interchromophoric exciton coupling of the neighboring NDI or PMDI subunits within a given triangle. Characteristically strong negative exciton Cotton effects are observed (FIG. 6B) in the range 350-400 nm, originating from the coupling of the π-π* electronic transitions polarized along the long z-axis of the NDI subunits (Band I region) in the case of the triangles (−)-3NDI-Δ and (−)-1PMDI-2NDI-Δ, while these strong negative exciton Cotton effects in this region are not observed in the case of the triangles (−)-2PMDI-1NDI-Δ and (−)-3PMDI-Δ, because of the absence of more than one neighboring NDI unit to promote the exciton coupling. It should be noted that the negative Cotton effects observed here are consistent with the absolute (RRRRRR)-configuration of the triangles. In the case of (−)-3NDI-Δ, the strong negative Cotton effect observed (FIG. 6B) at 242 nm originates from the coupling of the π-π* transitions polarized along the short y-axis of the NDI subunits (Band II region). On the other hand, the strong negative exciton couplet at 240 and 248 nm in the case of (−)-3PMDI-Δ appears as a consequence of the coupling of the π-π* transitions polarized along both the long z-axis and the short y-axis of the PMDI subunits, respectively. In the case of the isosceles triangles (−)-1PMDI-2NDI-Δ and (−)-2PMDI-1NDI-Δ, the negative exciton Cotton effects observed in the region 225-240 nm are presumably influenced by the multiple exciton couplings of the transition dipoles polarized along both the long z- and the short y-axes of the PMDI and the short y-axis of the NDI subunits.

Figure 7:
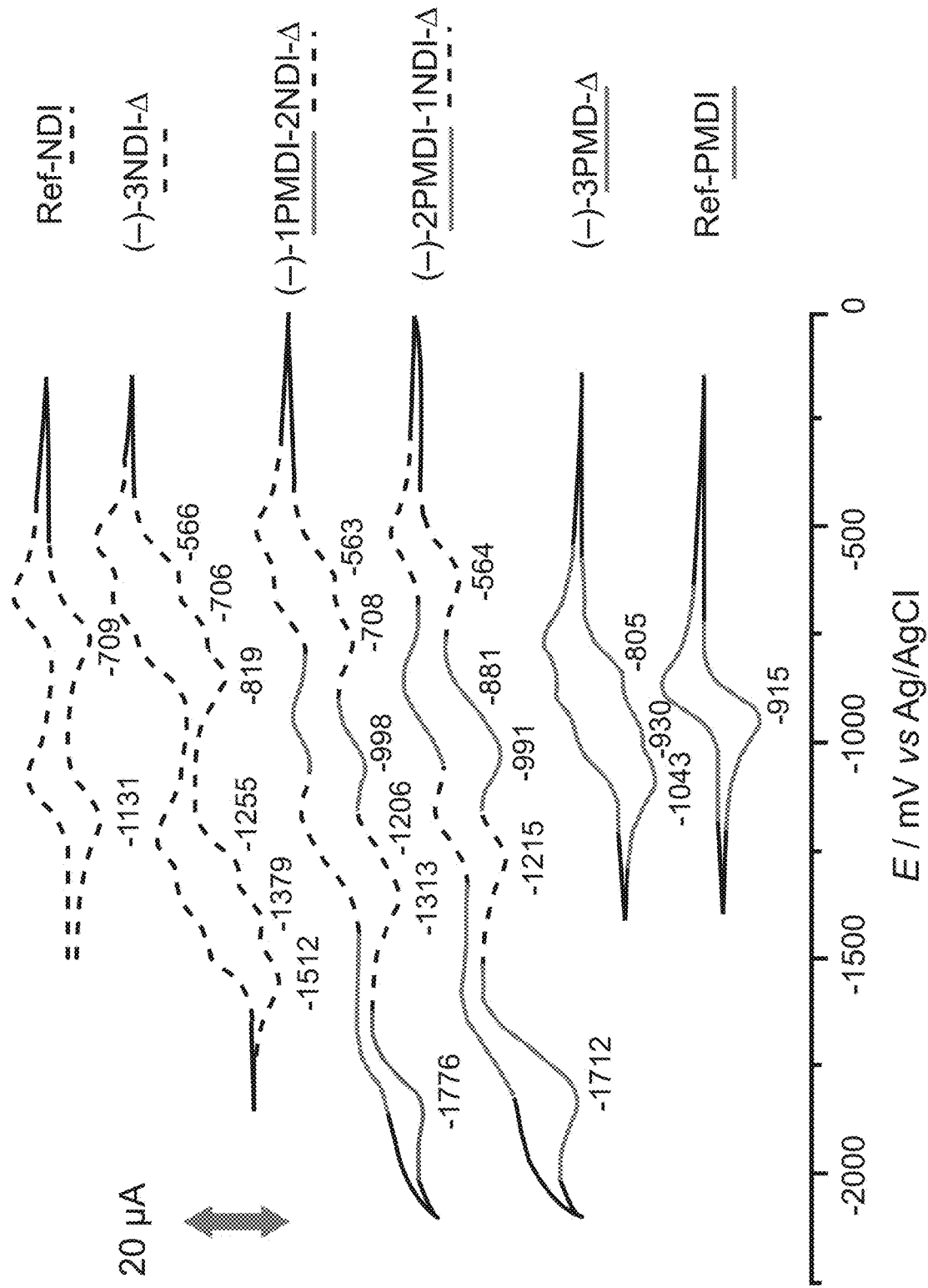
FIG. 7 shows solution-state CVs (0.5 mM in CH$_2$Cl$_2$, 100 mM TBAPF$_6$, 50 mVs$^{-1}$, 298 K) of Ref-NDI, (−)-3NDI-Δ, (−)-1PMDI-2NDI-Δ, (−)-2PMDI-1NDI-Δ, (−)-3PMDI-Δ and Ref-PMDI. Half-wave peak potentials (E$_{1/2}$) are shown in mV.
Figure 8A:
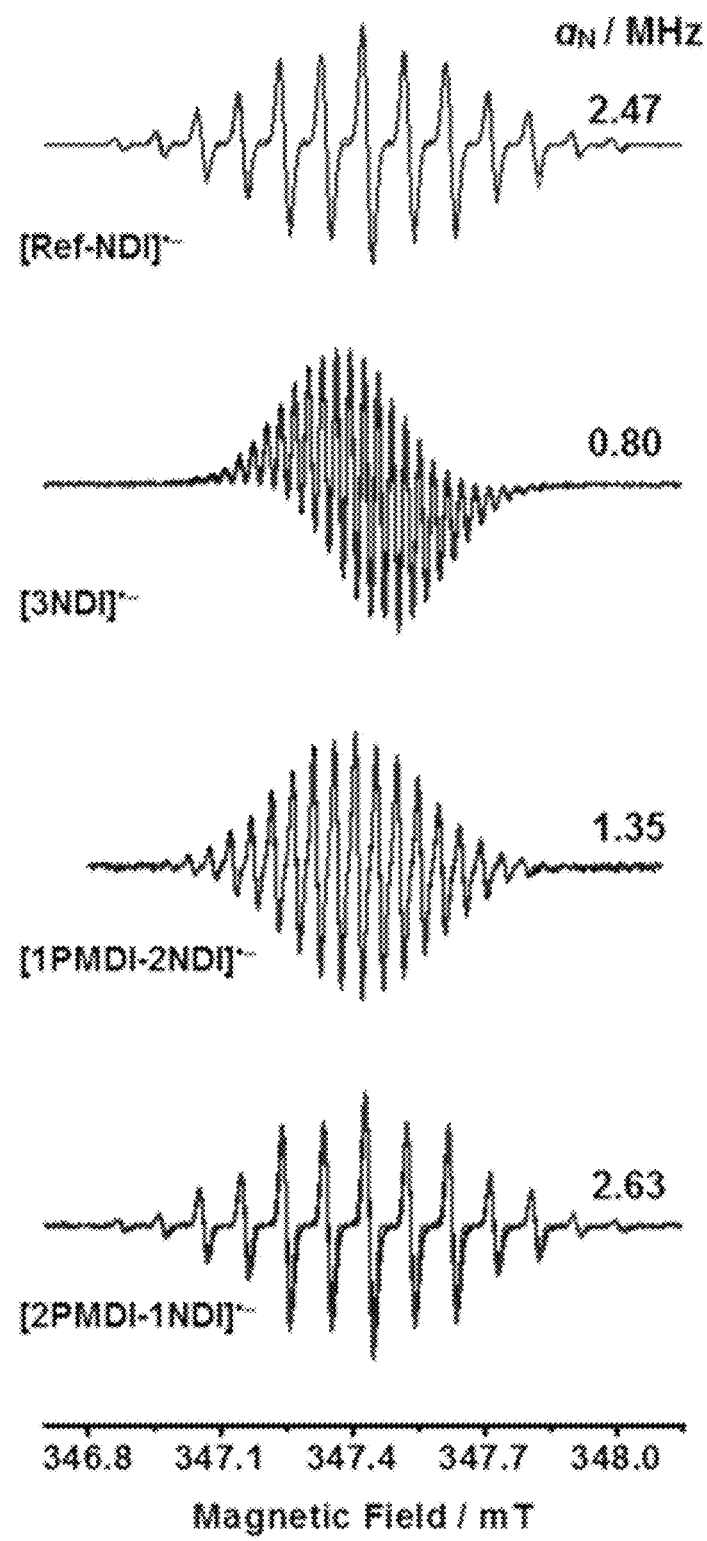
FIG. 8A shows CW-EPR spectra (0.25 mM in CH$_2$Cl$_2$, 298 K) of [Ref-NDI]$^{\cdot-}$, [(−)-3NDI-Δ]$^{\cdot-}$, [(−)-1PMDI-2NDI-Δ]$^{\cdot-}$ and [(−)-2PMDI-1NDI-Δ]$^{\cdot-}$, formed by the monoreduction of their corresponding neutral states by adding 1 equiv of cobaltocene. Overlay between the experimental spectra (black traces) and their simulated spectra (red traces). Isotropic nitrogen and proton hyperfine coupling constants are obtained from CW-EPR and $^1$H ENDOR, respectively.
Figure 8B:
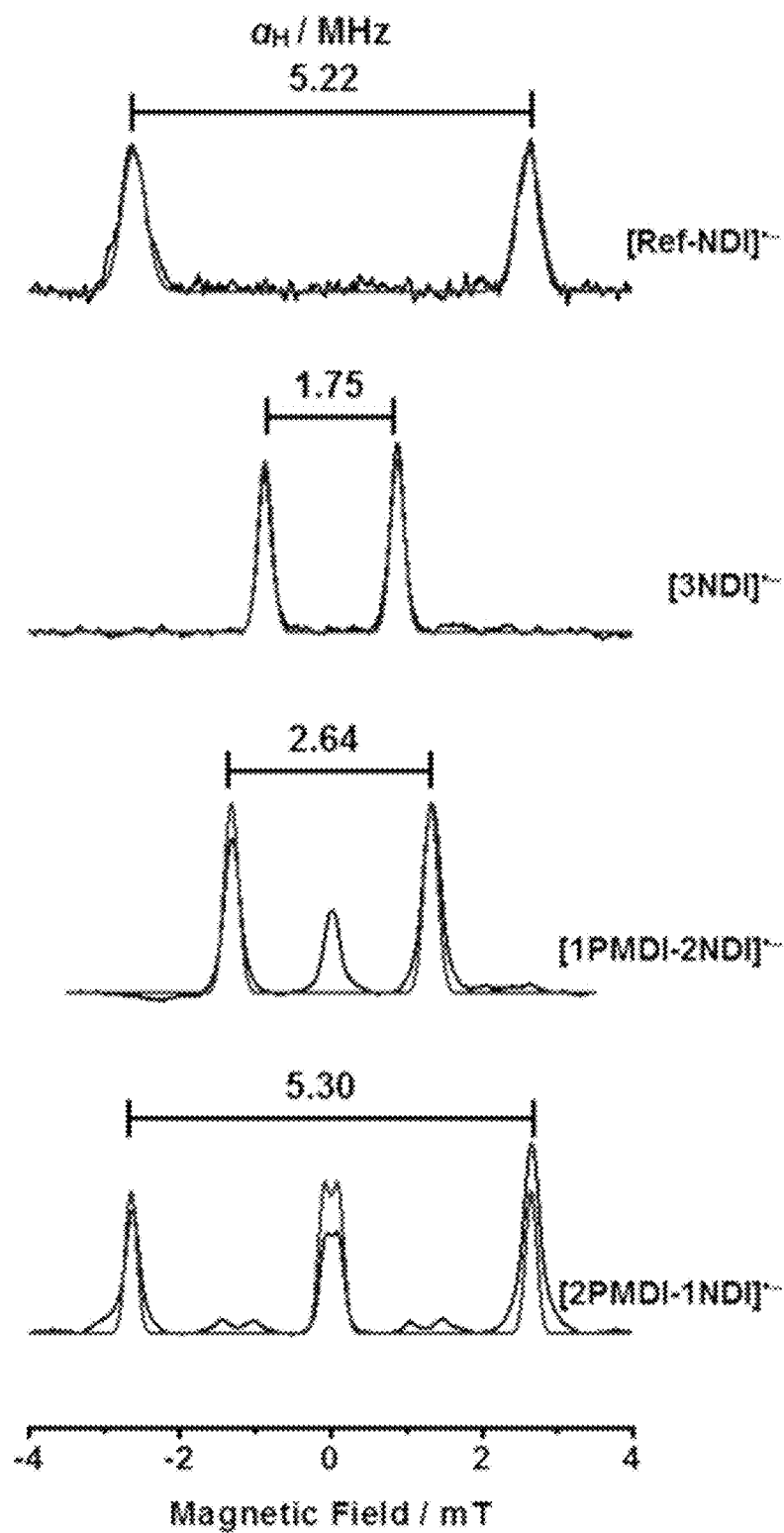
FIG. 8B shows $^1$H ENDOR spectra (0.25 mM in CH$_2$Cl$_2$, 298 K) of [Ref-NDI]$^{\cdot-}$, [(−)-3NDI-Δ]$^{\cdot-}$, [(−)-1PMDI-2NDI-Δ]$^{\cdot-}$ and [(−)-2PMDI-1NDI-Δ]$^{\cdot-}$, formed by the monoreduction of their corresponding neutral states by adding 1 equiv of cobaltocene. Overlay between the experimental spectra and their simulated spectra.

Cyclic voltammetry (CV) experiments (FIG. 7) in $CH_2Cl_2$ on the two isosceles triangles [(−)-1PMDI-2NDI-Δ and (−)-2PMDI-1NDI-Δ], and compared these results with the equilateral triangles [(−)-3NDI-Δ and (−)-3PMDI-Δ] as well as with the monomeric reference compounds (Ref-NDI and Ref-PMDI). While the CV of the Ref-NDI shows two distinct reversible one-electron waves with half-wave potentials at −709 and −1131 mV vs Ag/AgCl, corresponding to the formation of the [Ref-NDI]$^{•−}$ radical anion and the [Ref-NDI]$^{2−}$ dianion, respectively, the CV of (−)-3NDI-Δ shows clear splittings into six distinct reversible one-electron redox processes. Similarly, the CV of the Ref-PMDI shows a reversible one-electron reduction process at −915 mV, corresponding to the formation of the [Ref-PMDI]$^{•−}$ radical anion, while the CV of (−)-3PMDI-Δ also shows clear splittings into three distinct reversible one-electron waves. Strikingly, the CV of (−)-1PMDI-2NDI-Δ displays (FIG. 7) multiple reduction processes involving a total of six-electrons—namely, (i) two sequential distinct reversible one-electron waves at −563 and −708 mV, corresponding to the formation of two singly reduced [NDI]$^{•−}$ radical anions, (ii) a reversible one-electron wave at −998 mV, corresponding to the formation of a singly reduced [PMDI]$^{•−}$ radical anion, (iii) two closely following reversible one-electron processes at −1206 and −1313 mV, corresponding to the formation of two doubly reduced [NDI]$^{2−}$ dianions and (iv) finally, a quasi-reversible one-electron process at −1776 mV, corresponding to the formation of a doubly reduced [PMDI]$^{2−}$ dianion. Also, the CV of (−)-2PMDI-1NDI-Δ displayed (FIG. 7) multiple features containing six electrons in total—namely, (i) a reversible one-electron reduction process at −564 mV, corresponding to the formation of a singly reduced [NDI]$^{•−}$ radical anion, (ii) two closely following reversible one-electron reduction waves at −881 and −991 mV, corresponding to the formation of two singly reduced [PMDI]$^{•−}$ radical anions, (iii) a reversible one-electron reduction wave at −1215 mV, corresponding to the formation of a singly reduced [NDI]$^{2−}$ dianion, and (iv) finally, a quasi-reversible two-electron process at −1712 mV, corresponding to the formation of two doubly reduced [PMDI]$^{2−}$ dianions. Although the first reduction potential ($E_1$=ca.−564 mV) of the NDI unit in all of the NDI-containing triangles [(−)-3NDI-Δ, (−)-1PMDI-2NDI-Δ, (−)-2PMDI-1NDI-Δ] is nearly constant and shifted by 145 mV towards more positive potentials compared with that of Ref-NDI ($E_1$=−709 mV), the subsequent reduction potentials can be tuned significantly, thus establishing a set of unique molecular triangles for structure-property relationship investigations and the device fabrication of efficient energy storage. All of these observations suggest that, despite having two types of non-identical neighboring redox-active units within triangular architectures, each molecular triangle can accept reversibly up to six electrons In order to gain more insight into the through-space electron sharing among the neighboring redox-active NDI and PMDI units within the molecular triangles, we carried out continuous-wave electron paramagnetic resonance (CW-EPR) and electron-nuclear double resonance (ENDOR) spectroscopies on the monoreduced radical anions of the triangles generated by adding one equivalent of cobaltocene ($CoCp_2$) as the chemical reductant. Solution-phase CW-EPR spectra of [(−)-3NDI-Δ]$^{•−}$ and [(−)-1PMDI-2NDI-Δ]$^{•−}$ monoradical anions reveal (FIG. 8A) a decrease in linewidth by a factor of ca. 1.75 and 1.40, respectively, relative to that of [Ref-NDI]$^{•−}$. In striking contrast, the EPR spectrum of [(−)-2PMDI-1NDI-Δ]$^{•−}$ matches perfectly with that of [Ref-NM]$^{•−}$, i.e., no decrease in EPR-linewidth was observed. According to the Norris relationship, sharing of an electron by n NDI or n PMDI subunits should result in a decrease in EPR-linewidth by a factor of √n. Therefore, the observed decrease in linewidth by a factor of √3 and √2 in the EPR spectra of [(−)-3NDI-Δ]$^{•−}$ and [(−)-1PMDI-2NDI-Δ]$^{•−}$, respectively, and the absence of a linewidth decrease in [(−)-2PMDI-1NDI-Δ]$^{•−}$ suggests that the unpaired electron is shared among all NDI subunits present within a given molecular triangle on the timescale of the electron-nuclear hyperfine interaction ($10^7$ s$^{−1}$). Moreover, the CW-ENDOR spectra of [(−)-3NDI-Δ]$^{•−}$ and [(−)-1PMDI-2NDI-Δ]$^{•−}$ reveal (FIG. 8B) an obvious decrease in the isotropic hyperfine coupling constant ($a_H$) by factors of ca. 3 and 2, respectively, relative to that of [(−)-2PMDI-1NDI-Δ]$^{•−}$ and [Ref-NDI]$^{•−}$, once again confirming that the unpaired electron is being shared only by the NDI subunits present within the molecular triangles at a rate (>$10^7$ s$^{−1}$) exceeding the CW-ENDOR timescale.

Figure 6C:
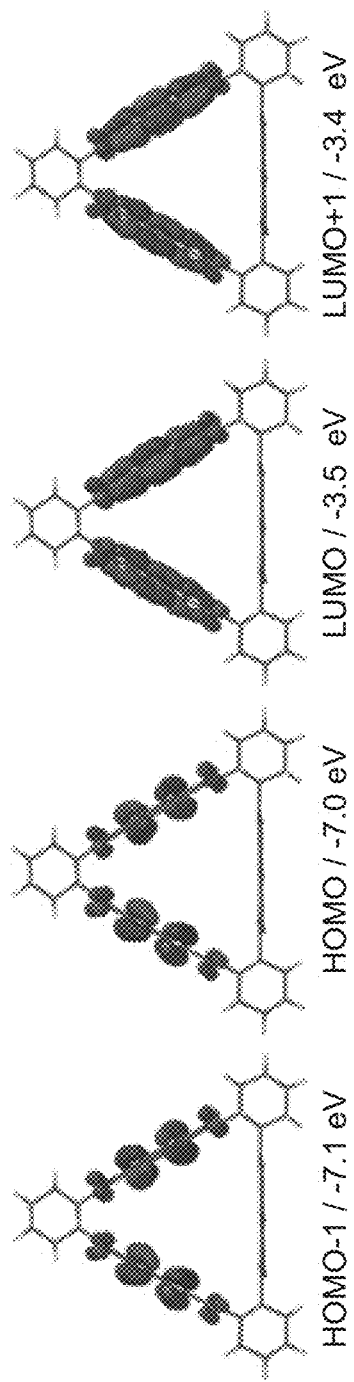
FIG. 6C shows graphical representations of the DFT-calculated (B3LYP/6-31G**) FMOs of the molecular triangles showing the available HOMO−1, HOMO, LUMO and LUMO+1 levels of (−)-1PMDI-2NDI-Δ. FMO refers to the frontier molecular orbital, HOMO refers to the highest occupied molecular orbital and LUMO refers to the lowest unoccupied molecular orbital. Orbital isosurfaces are illustrated at 0.004 electrons Bohr$^{-3}$.
Figure 6D:
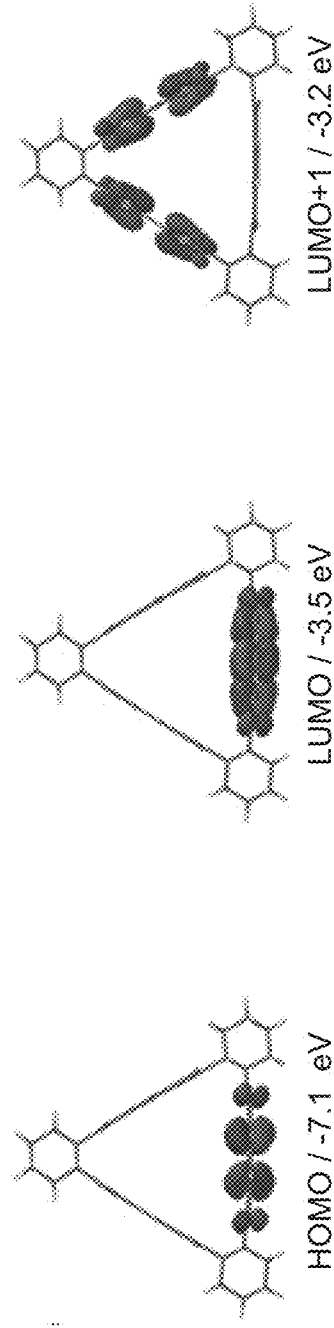
FIG. 6D shows graphical representations of the DFT-calculated (B3LYP/6-31G**) FMOs of the molecular triangles showing the available HOMO, LUMO and LUMO+1 levels of (−)-2PMDI-1NDI-Δ. FMO refers to the frontier molecular orbital, HOMO refers to the highest occupied molecular orbital and LUMO refers to the lowest unoccupied molecular orbital. Orbital isosurfaces are illustrated at 0.004 electrons Bohr$^{-3}$.

Without wishing to be bound to theory, Density Functional Theory (DFT) calculations we performed to assist with our understanding of these molecular systems. The DFT calculations on the equilateral triangles revealed the presence of delocalized frontier molecular orbitals (FMOs) located on all of the three symmetrically equivalent NDI subunits in the LUMO of (−)-3NDI-Δ, supporting the CV and EPR results commensurate with cyclic through-space electron sharing among all the neighboring NDI subunits. We therefore performed (FIG. 6C-6D) similar DFT calculations using a continuum solvent model with the functional B3LYP/6-31G* on the two isosceles triangles (−)-1PMDI-2NDI-Δ and (−)-2PMDI-1NDI-Δ to confirm where the delocalized FMOs are located in each case. We observed (FIG. 6C-6D) that the LUMO, as well as LUMO+1, of (−)-1PMDI-2NDI-Δ are located only on the two NDI subunits present, while the LUMO of (−)-2PMDI-1NDI-Δ is located only on the one available NDI subunit. These calculations are consistent with the CV, as well as EPR/ENDOR results, supporting the through-space sharing of the unpaired electron selectively by the NDI subunits present in the case of the monoreduced radical anions [(−)-1PMDI-2NDI-Δ]$^{•−}$ and [(−)-2PMDI-1NDI-Δ]$^{•−}$. The LUMO+1 of (−)-

2PMDI-1NDI-Δ is located, however, on both the PMDI subunits present in the triangle, indicating that the two subsequent reductions of the monoradical anion to di- and tri-radical anionic states occur on the two electronically communicating PMDI subunits.

We investigated the structure-performance relationship of this unique set of molecular triangles, namely (−)-3NDI-Δ, (−)-1PMDI-2NDI-Δ and (−)-2PMDI-1NDI-Δ. The electrochemical performance of these triangles was characterized using CR2032-type coin cells. The electrodes were prepared by mixing 50 wt % active material [(−)-1PMDI-2NDI-Δ or (−)-2PMDI-1NDI-Δ], 40 wt % carbon black and 10 wt % polyvinylidene fluoride (PVDF) binder in anhydrous N-methyl-2-pyrrolidone (NMP) to form a well-dispersed slurry, followed by coating on aluminum foil and drying under vacuum at 120° C. for 24 h.

The solid-state CV of (−)-1PMDI-2NDI-Δ displayed (FIG. 9A) three sets of peaks, centered at 2.50, 2.43 and 2.10 V vs Li/Li$^+$, presumably corresponding to (i) the two-electron (mono reduction of two NDI subunits to two [NDI] ]$^{.-}$ radical anions), (ii) the three-electron (first reduction of PMDI subunit to [PMDI]]$^{.-}$ radical anion and subsequent reduction of two [NDI]]$^{.-}$ radical anions to [NDI]$^{2-}$ dianions) and (iii) one-electron (subsequent reduction of [PMDI] ]$^{.-}$ radical anion to [PMDI]$^{2-}$ dianion) redox processes, respectively. Also, the solid-state CV of (−)-2PMDI-1NDI-Δ displayed (FIG. 9D) only two sets of peaks, centered at 2.43 and 2.19 V vs Li/Li$^+$, presumably corresponding to the four-electron (double reduction of NDI subunits to [NDI]$^{2-}$ dianions and the monoreduction of the two PMDI subunits to two [PMDI]]$^{.-}$ radical anions) and two-electron (subsequent reduction of two [PMDI]]$^{.-}$ radical anion subunits to two [PMD]$^{2-}$ dianions) redox processes. In addition, the comparison of the solid-state CV (FIGS. 9A and 9D) with the solution-state CV (FIG. 7) of (−)-1PMDI-2NDI-Δ and (−)-2PMDI-1NDI-Δ reveals significant overlapping of the peaks in the solid-state. This overlap leads to a decrease in the total number of peaks observed and some of these peaks are not well-resolved. It is interesting to note (FIGS. 9A and 9D) that the areas of the oxidation and reduction peaks as well as the peak potentials in the solid-state CV remained almost unchanged, with a slight decrease in the current, during cycling for both (−)-1PMDI-2NDI-Δ and (−)-2PMDI-1NDI-Δ, suggesting that all the redox reactions are highly reversible even in the solid-state. In line with the CV results obtained previously for (−)-3NDI-Δ, the good electrochemical stability and reversibility of (−)-1PMDI-2NDI-Δ and (−)-2PMDI-1NDI-Δ obtained here prompted us to evaluate the structure-performance relationship of these triangles as active materials in organic rechargeable LIBs.

Figure 9A:
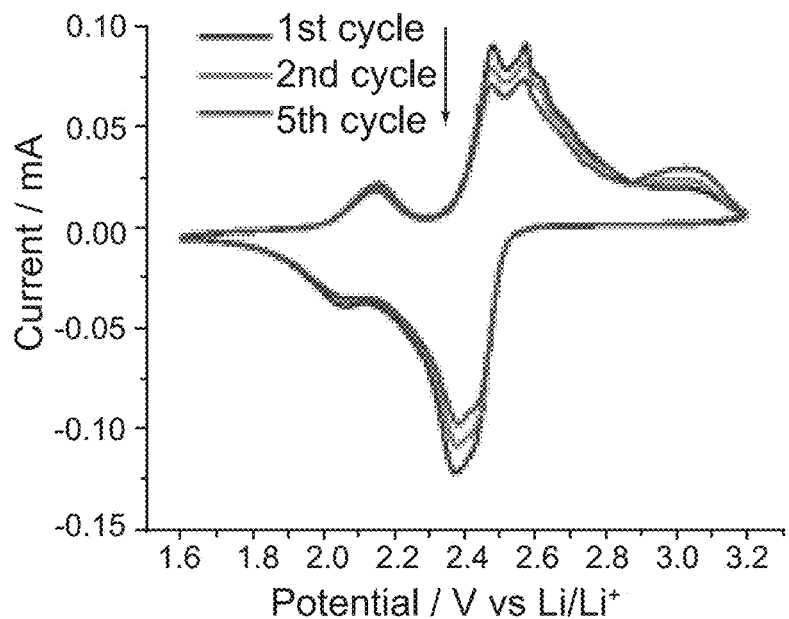
FIG. 9A shows solid-state CVs and charge/discharge properties of the (−)-1PMDI-2NDI-Δ batteries. CV profiles of the first, second and fifth cycles are recorded at a scan rate of 0.05 mVs$^{-1}$.
Figure 9B:
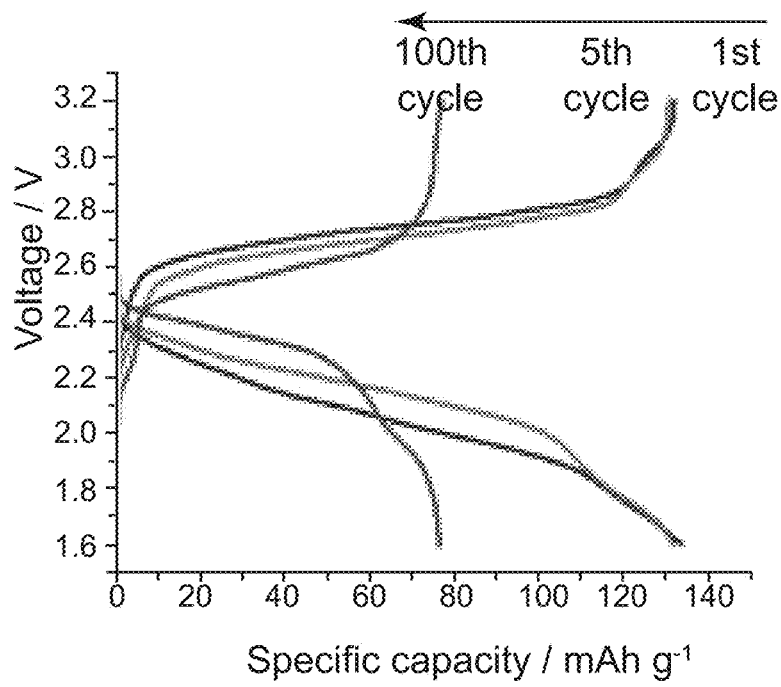
FIG. 9B shows charge/discharge profiles for the first, fifth and hundredth cycles at rates of 0.5C for the (−)-1PMDI-2NDI-Δ battery.
Figure 9C:
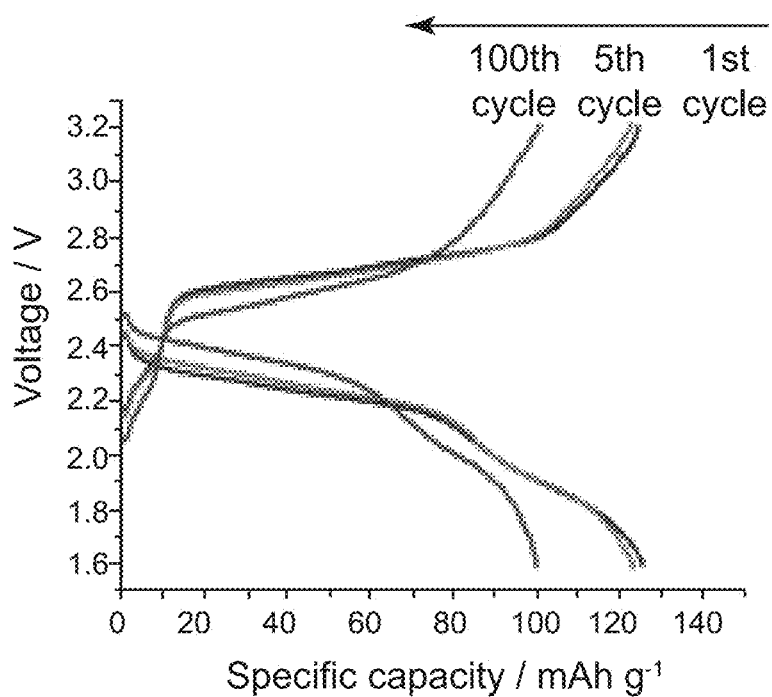
FIG. 9C shows charge/discharge profiles for the first, fifth and hundredth cycles at rates of 1.0C for the (−)-1PMDI-2NDI-Δ battery.
Figure 9D:
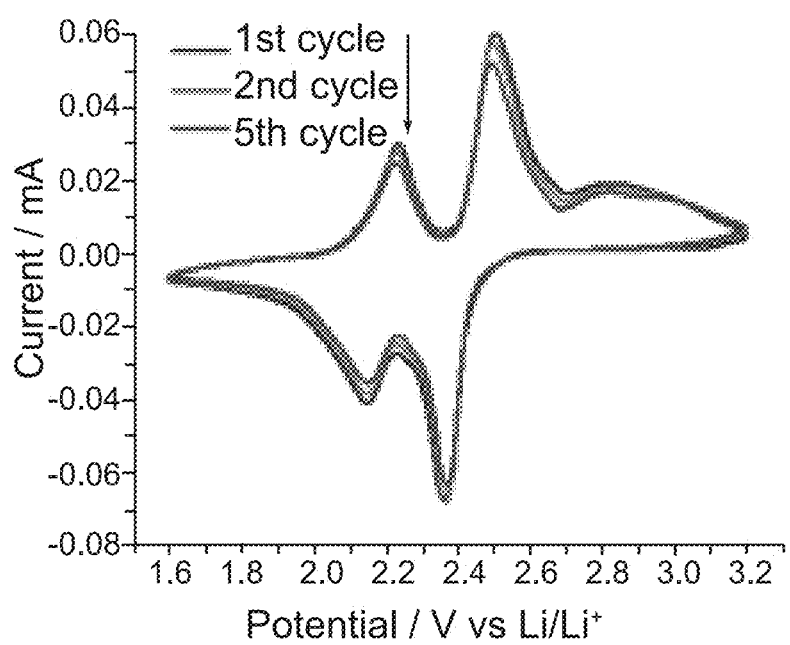
FIG. 9D shows solid-state CVs and charge/discharge properties of the (−)-2PMDI-1NDI-Δ batteries. CV profiles of the first, second and fifth cycles are recorded at a scan rate of 0.05 mVs$^{-1}$.

We investigated the galvanostatic measurements of the batteries at different current rates of 0.5 and 1.0C. In the case of (−)-1PMDI-2NDI-Δ, a three-step charge/discharge profile was noted upon careful observation at rates of 0.5 and 1.0C (FIGS. 9B-9C). The not so well-defined plateaus displayed in the charge/discharge profile of the (−)-1PMDI-2NDI-Δ battery at about 2.3 and 2.0 V match the CV results (FIG. 9A). The experimental charge and discharge capacities (FIG. 9B) of the (−)-1PMDI-2NDI-Δ battery at 0.5C are 132.2 and 133.9 mAh g$^{-1}$, corresponding to 81 and 82% of the theoretical capacity (162.6 mAh g$^{-1}$) of (−)-1PMDI-2NDI-Δ, respectively. The cycling performance of (−)-1PMDI-2NDI-Δ battery was also tested (FIG. 10) at current rates of 0.5 and 1.0C. While a slight discharge capacity decay was observed during the initial cycling, the rate of decay is improved when the rate is increased from 0.5 to 1.0C.

Figure 9E:
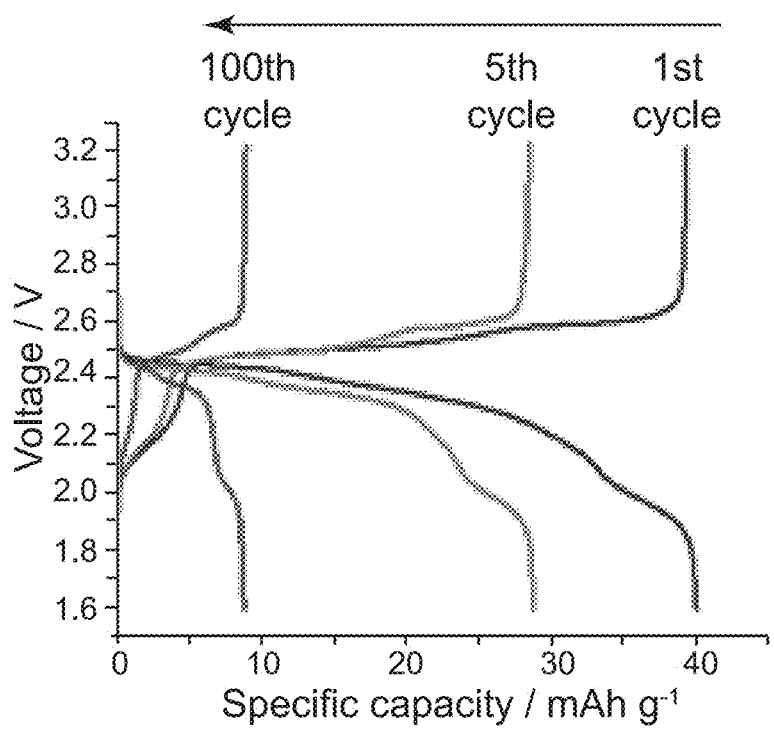
FIG. 9E shows charge/discharge profiles for the first, fifth and hundredth cycles at rates of 0.5C for the (−)-2PMDI-1NDI-Δ battery.
Figure 9F:
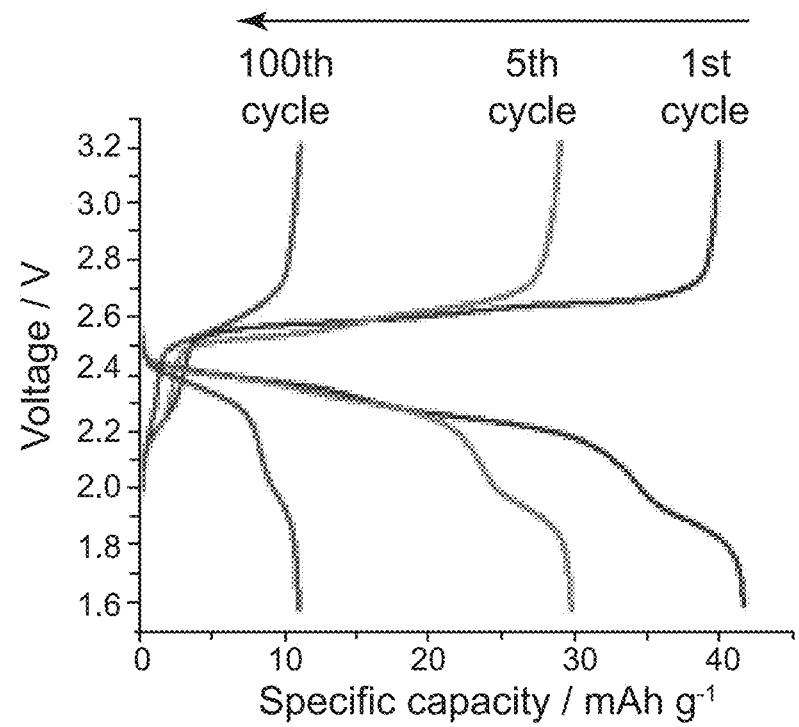
FIG. 9F shows charge/discharge profiles for the first, fifth and hundredth cycles at rates of 1.0C for the (−)-2PMDI-1NDI-Δ battery.
Figure 10A:
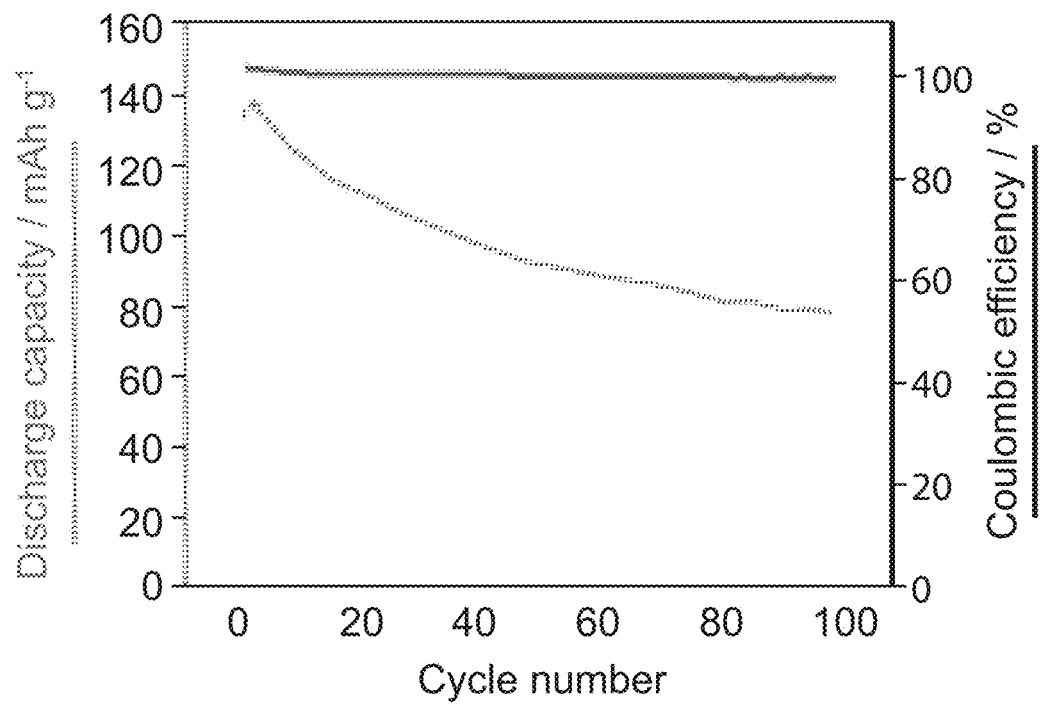
FIG. 10A shows cycling performance and Coulombic efficiency at a rate of 0.5C for the (−)-1PMDI-2NDI-Δ battery over 100 cycles.
Figure 10B:
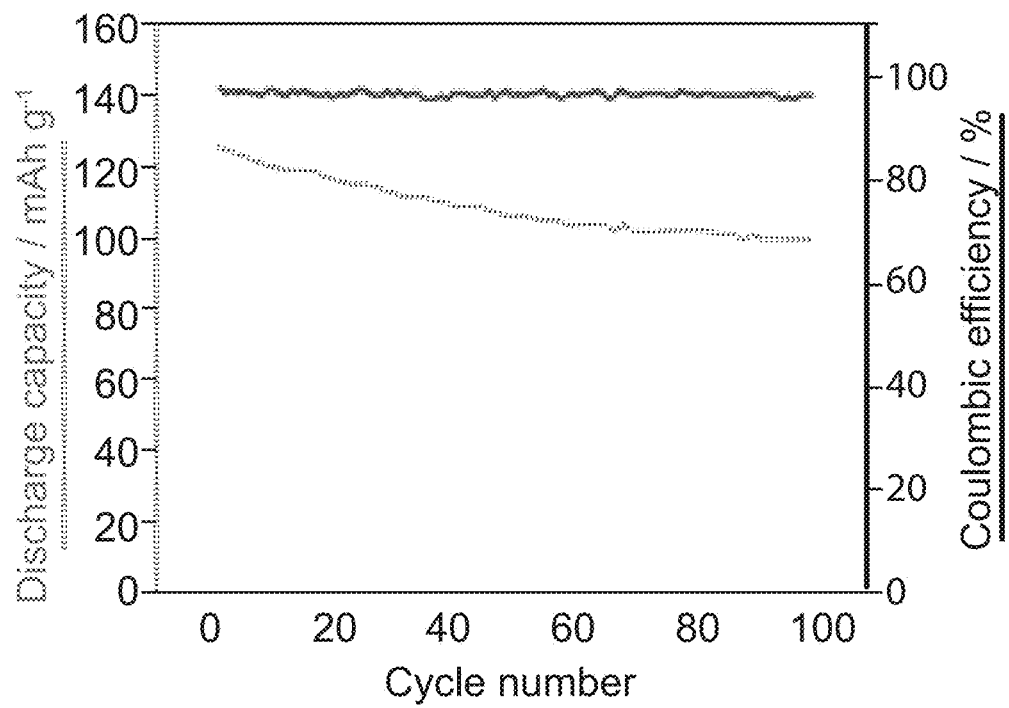
FIG. 10B shows cycling performance and Coulombic efficiency at a rate of 1.0C for the (−)-1PMDI-2NDI-Δ battery over 100 cycles.
Figure 10C:
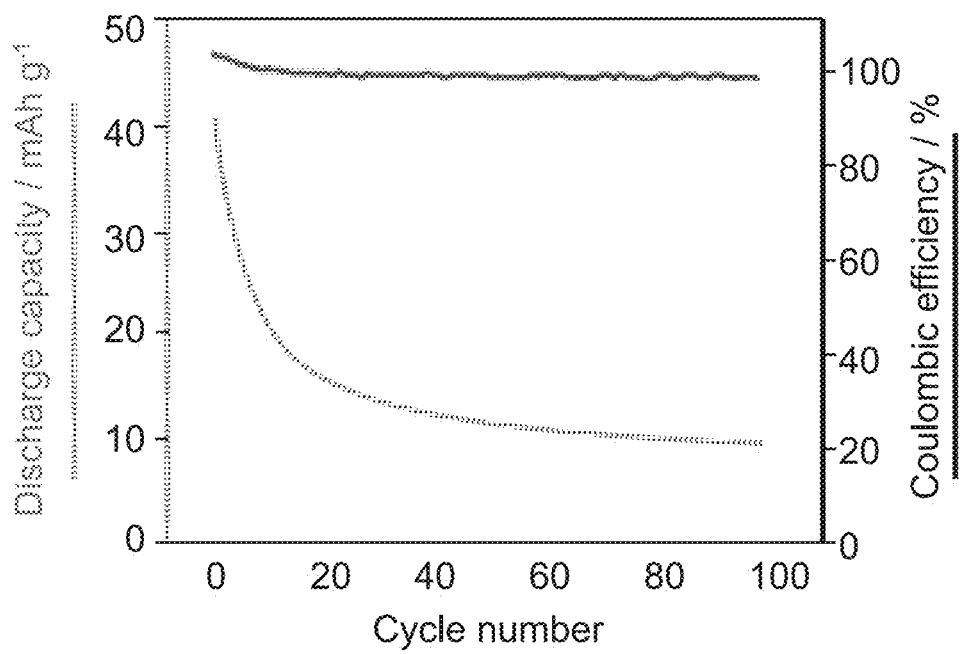
FIG. 10C shows cycling performance and Coulombic efficiency at a rate of 0.5C for the (−)-2PMDI-1NDI-Δ battery over 100 cycles.
Figure 10D:
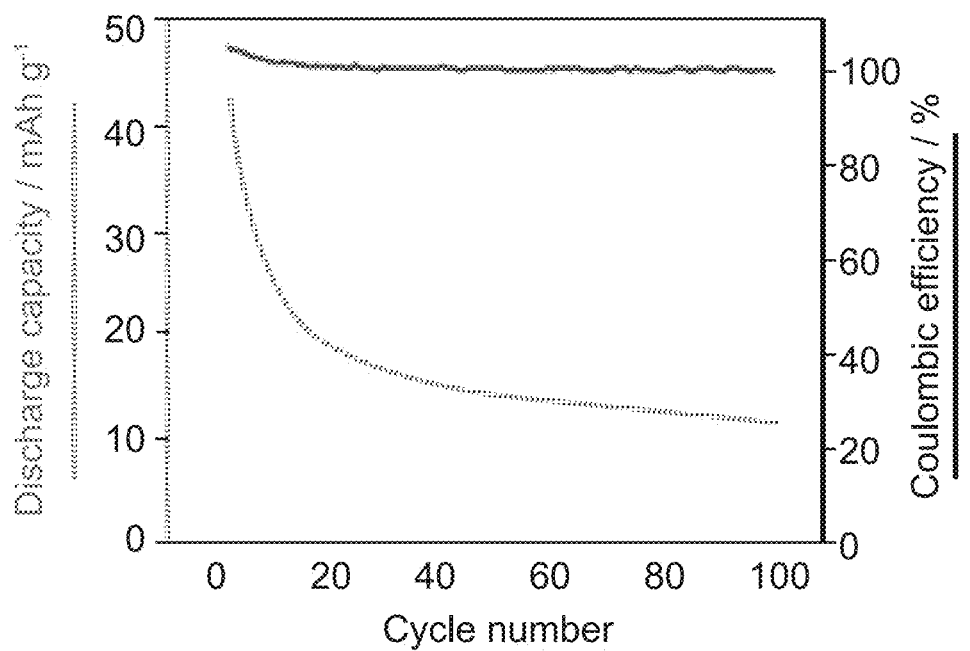
FIG. 10D shows cycling performance and Coulombic efficiency at a rate of 1.0C for the (−)-2PMDI-1NDI-Δ battery over 100 cycles.

Similar experiments performed on the (−)-2PMDI-1NDI-Δ battery also revealed (FIGS. 9E-9F) a more well-defined charge/discharge profile upon careful observation at rates of 0.5 and 1.0C. Surprisingly, the experimental charge and discharge capacities of (−)-2PMDI-1NDI-Δ battery at 0.5C are 39.4 and 40.1 mAh g$^{-1}$, corresponding to only 23.0 and 23.5% of the theoretical capacity (171.3 mAh g$^{-1}$) of (−)-2PMDI-1NDI-Δ. By contrast, the cycling performance of the (−)-2PMDI-1NDI-Δ battery showed (FIG. 10) a rapid decay of the capacity. The poor performance observed for the (−)-2PMDI-1NDI-Δ battery, compared with that of the (−)-1PMDI-2NDI-Δ battery, could be attributed to the increased solubility of the neutral as well as the reduced states of the (−)-2PMDI-1NDI-Δ based active material under the galvanostatic measurement conditions.

Overall, the comparisons of the rate performance and cycling stability of this series of diimide-based batteries containing (−)-3NDI-Δ, (−)-1PMDI-2NDI-Δ and (−)-2PMDI-1NDI-Δ suggest that the electrochemical cell performance of the batteries follows the order (−)-3NDI-Δ>(−)-1PMDI-2NDI-Δ>(−)-2PMDI-1NDI-Δ. From this data, it can be concluded that the replacement of the NDI with PMDI subunits within the molecular triangle can dramatically increase the solubility of the resultant active material in the battery electrolytes. These observations are in good agreement with the literature report which suggests that the PMDI derivatives are noted to deliver lower capacities compared with their NDI counterparts, on account of the larger electron affinity of the NDI units.

In summary, two chiral isosceles triangles (−)-1PMDI-2NDI-Δ and (−)-2PMDI-1NDI-Δ have been synthesized. Comparison of the $^1$H NMR spectra of these two triangles with those of the previously characterized equilateral triangles [(−)-3NDI-Δ and (−)-3PMDI-Δ] is consistent with the lower symmetries (C$_2$ point groups) of these two isosceles triangles. The solid-state (super)structures of the isosceles triangles, grown from both 1,2-dibromoethane/n-hexane and DMF/H$_2$O, reveal the formation of 2D layer-like superstructures, confirming the lack of the ability of the isosceles triangles to form extended 1D tubular superstructures previously observed[30] in the case of (−)-3NDI-Δ. Specifically, (−)-2PMDI-1NDI-Δ, in the presence of DMF, forms two different types of intermolecular NDI-NDI and NDI-PMDI π-π stacking dimers [(P)- and (M)-Dimers] with opposite supramolecular helicities. Cyclic voltammetry suggests that through-space electronic communication between the identical NDI-NDI or PMDI-PMDI units in the isosceles triangles produces up to six accessible redox states. It should be noted that both the EPR and ENDOR experiments, supported by DFT calculations, in the case of monoreduced radical anions of the isosceles triangles indicate that the unpaired electron is shared selectively among the adjacent NDI—but not PMDI—units within the triangular geometries. The isosceles triangles, when employed as active materials in organic rechargeable lithium-ion batteries, were shown to have capacities of 140.1 and 58.1 mAh g$^{-1}$ for (−)-1PMDI-2NDI-Δ and (−)-2PMDI-1NDI-Δ, respectively. A better rate performance and cycling stability were noted for (−)-1PMDI-2NDI-Δ than for (−)-2PMDI-1NDI-Δ, mainly on account of the good solubility of the active material (−)-2PMDI-1NDI-Δ in the battery electrolytes. Probing these relationships is providing us with increased understanding on how the rational design of redox-active organic molecules affects their electron transport properties, thus paving the way for the fabrication of next generation organic electronics and energy storage devices.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All references, including publications, patent application, and patents, cited herein are hereby incorporated by reference to the same extent as if each reference were individually and specifically indicated to be incorporated by reference and were set forth in its entirety.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

Example 1

Materials/General Methods/Instrumentation

All chemicals and reagents were purchased from commercial suppliers (Aldrich or Fisher) and used without further purification. Compounds, symmetric triangular macrocycles ((−)-3NDI-Δ and (−)-3PMDI-Δ), 1,2-cyclohexane-bis(naphthalene monoimide monoanhydride) (−)-2NIA, bis(cyclohexyl)naphthalenetetracarboxylic diimide (Ref-NDI) and bis(cyclohexyl)pyromellitic diimide (Ref-PMDI) were prepared according to previous literature procedures. Cobaltocene ($CoCp_2$) was handled and stored in an argon Glovebox. While small amounts of (RR)-trans-1,2-cyclohexanediamine were purchased from Aldrich Chemical Company, larger quantities of the pure enantiomers were obtained by resolving racemic trans-1,2-cyclohexanediamine with L-(+)-tartaric acid, as described in the literature.[6] Thin layer chromatography (TLC) was performed on silica gel 60 F254 (E. Merck). Column chromatography was carried out on silica gel 60F (Merck 9385, 0.040-0.063 mm). High-resolution mass spectra were measured on an Agilent 6210 Time of Flight (TOF) LC-MS, using an ESI source, coupled with Agilent 1100 HPLC stack, using direct infusion (0.6 mL/min). UV/Vis absorption spectra were recorded using a UV-3600 Shimadzu spectrophotometer. Circular dichroism (CD) measurements were carried out on a Jasco J-815 spectrometer. Nuclear magnetic resonance (NMR) spectra were recorded on a Bruker Avance 600 and Varian P-Inova 500 spectrometers, with working frequencies of 500 and 600 MHz, respectively. Chemical shifts are reported in ppm relative to the signals corresponding to the residual non-deuterated solvents ($CDCl_3$: δ 7.26 ppm). Continuous-wave electron paramagnetic resonance (EPR) and electron-nuclear double resonance (ENDOR) spectra were acquired at X-band (9.5 GHz) with a Bruker Elexsys E580 spectrometer, fitted with the DICE ENDOR accessory, an EN801 resonator, and an ENI A-500 RF power amplifier. Applied RF powers ranged from 200 to 400 W across the 7 MHz scanned range, and the microwave power ranged from 2 to 20 mW. EPR Spectra were recorded with 0.010 mT modulation amplitude. The sample temperatures were controlled by a liquid $N_2$ flow system. Samples were reduced using $CoCp_2$ as the chemical reductant and loaded into 1.4 mm I.D. quartz tubes, which were sealed with epoxy resin in an argon-filled glovebox. A spline fit baseline correction was applied to the ENDOR spectra following integration. The EPR and the ENDOR spectra were fit in MATLAB using EasySpin v4.5.5.

Cyclic Voltammetry (CV).

The experiments were carried out at room temperature in Ar-purged solutions of $CH_2Cl_2$ with a Gamry Multipurpose instrument (Reference 600) interfaced to a PC. All CV experiments were performed using a glassy carbon working electrode (0.071 $cm^2$). The electrode surface was polished routinely with 0.05 μm alumina-water slurry on a felt surface immediately before use. The counter electrode was a Pt coil and the reference electrode was an Ag/AgCl electrode. The concentration of the sample and supporting electrolyte, tetrabutylammonium hexafluorophosphate ($TBAPF_6$), were 1.0 mM and 0.1 M, respectively. The CV cell was dried in an oven immediately before use, and Ar was continually flushed through the cell as it was cooled down to room temperature to avoid condensation of water.

Quantum Mechanical Calculations.

The geometries of the chiral asymmetric triangular macrocycles were initially relaxed using molecular mechanics with the MMFF94 force field, as implemented in the Avogadro 1.1.0 software. Geometries were subsequently relaxed using density functional theory (DFT), implemented in the TeraChem 1.5K software. All DFT calculations made use of the B3LYP exchange-correlation functional with a split-valence double zeta basis set with added diffuse and polarization functions (6-31G*); all calculations on radical species were done using unrestricted DFT. Following geometry minimization in TeraChem 1.5K, geometries were submitted to QChem 4.0 for further geometry optimization.

Battery Fabrication.

Organic electrodes were fabricated using the following procedure. The active material, conductive acetylene black, and polyvinylidene fluoride (PVDF) binder (100 mg in total) were mixed in a ratio of 5:4:1 (50 wt % active material) by weight in 1 mL of N-methyl-2-pyrrolidone (NMP) which was stirred with a mechanical stirrer for 2 hours at room temperature and coated onto an aluminum foil substrate with a doctor blade set to a height of 15 μm. Coatings were dried in a vacuum oven at 80° C. for 24 hours, then were cut into circular electrode discs with diameters of 11 mm. After weighing the electrode discs, they were transferred into a glove box and assembled under an Argon atmosphere into half lithium-ion batteries using CR2032 coin cell hardware, with lithium foil as the counter electrode and a Celgard® 2400 separator and a total of 200 μL of a 1 M lithium hexafluorophosphate ($LiPF_6$) in a (1:1) ethylene carbonate and dimethyl carbonate electrolyte solution.

Electrochemical Characterizations.

Galvanostatic charging/discharging of the batteries was monitored within a voltage window of 1.6-3.2 V (versus Li/Li$^+$) using (i) an MTI BST8-WA Battery Tester for applied currents lower than 1 mA, and (ii) an MTI BST8-MA Battery Tester for applied currents higher than 1 mA. Solid-state cyclic voltammograms (CVs) were recorded within the same voltage window on a Gamry Dual Cell CR2032 Battery Holder, connected to a Gamry Reference 600 potentiostat and interfaced to a PC. The scan rates were 0.05 mV·s$^{-1}$. All electrochemical testing was conducted at room temperature (~30° C.).

Example 2

Synthetic Protocols

A summary of the schemes used for these synthetic protocols are provided in FIG. 1.

(−)-1PMDI-2NH$_2$.

The synthetic protocol was adopted according to the literature procedure, except that a slightly modified procedure was used as follows.[Kaik, M.; Gawroński, *J. Org. Lett.* 2006, 8, 2921; Kaik, M.; Gawroński, J. *Tetrahedron: Asymmetry* 2003, 14, 1559] The compound (RR)-trans-1,2-cyclohexanediamine (1.14 g, 10.0 mmol) was added quickly in one portion to a vigorously stirred suspension of pyromellitic dianhydride (1.09 g, 5.0 mmol) and p-toluenesulfonic acid monohydrate (1.90 g, 10.0 mmol) in glacial AcOH (25 mL) at room temperature. The reaction mixture was stirred under reflux until a homogenous solution was obtained and the stirring was continued for an additional 2 h, after which time the homogenous solution became transformed into a suspension. The reaction mixture was cooled down to room temperature and the solvent was removed under reduced pressure. The crude residue was purified by precipitation followed by filtration from MeOH-Et$_2$O to afford the ditosylate of (−)-1PMDI-2NH$_2$ as a white solid. This ditosylate salt of (−)-1PMDI-2NH$_2$ was taken up in CH$_2$Cl$_2$ (100 mL) and a saturated NaHCO$_3$ solution (50 mL) was added to this CH$_2$Cl$_2$ solution. The resulting solution was stirred overnight at room temperature. The organic layer was separated and the aqueous layer was extracted with CH$_2$Cl$_2$ (3×50 mL). The organic layers were combined, dried (MgSO$_4$) and concentrated under reduced pressure to afford pure (−)-1PMDI-2NH$_2$ (1.33 g, 3.24 mmol) in 65% overall yield as a white solid. $^1$H NMR (500 MHz, CDCl$_3$, 25° C.) δ=8.24 (s, 2H), 3.90-3.80 (m, 2H), 3.39 (td, J=10.9, 4.1 Hz, 2H), 2.28-2.10 (m, 2H), 2.10-2.01 (m, 2H), 1.91-1.72 (m, 8H), 1.51-1.31 (m, 4H), 1.30-1.11 (m, 4H). $^{13}$C NMR (125 MHz, CDCl$_3$, 25° C.) δ=166.9, 137.2, 118.3, 59.1, 51.0, 37.5, 29.5, 25.7, 25.2.

(−)-1PMDI-2NDI-Δ.

A warm suspension of (−)-1PMDI-2NH$_2$ (697 mg, 1.7 mmol) in anhydrous DMF (30 mL) was added quickly to a vigorously stirred homogeneous solution of (−)-2NIA (1.05 g, 1.7 mmol) in anhydrous DMF (70 mL) at 100° C. under N$_2$. The resulting reaction mixture was stirred overnight at 130° C. under N$_2$, after which the DMF was removed under reduced pressure (~3 mbar) at 60° C. The deep red residue was dissolved in CH$_2$Cl$_2$ and subjected to column chromatography (SiO$_2$: CH$_2$Cl$_2$/Me$_2$CO, gradient from 0-10% Me$_2$CO) to afford pure (−)-1PMDI-2NDI-Δ (0.84 g, 0.85 mmol) in 50% yield as an off-white solid. $^1$H NMR (500 MHz, CDCl$_3$, 25° C.) δ=8.60-8.48 (m, 8H), 7.88 (s, 2H), 6.31-6.16 (m, 2H), 5.84 (td, J=11.7, 3.7 Hz, 2H), 5.45 (td, J=11.7, 3.6 Hz, 2H), 2.60-2.46 (m, 2H), 2.46-2.33 (m, 2H), 2.21-2.09 (m, 2H), 2.07-1.83 (m, 12H), 1.77-1.66 (m, 2H), 1.66-1.52 (m, 4H). $^{13}$C NMR (125 MHz, CDCl3, 25° C.) δ=165.9, 165.3, 162.9, 162.7, 162.6, 162.5, 136.4, 136.1, 131.7, 131.6, 131.0, 130.9, 126.6, 126.4, 126.2, 126.1, 125.9, 118.7, 54.1, 51.4, 31.2, 30.1, 29.7, 26.0, 25.6, 25.4. ESI-HRMS (m/z): calcd for [M+H]$^+$=989.2777; found: 989.2779.

(−)-2PMIA.

A warm solution of (RR)-trans-1,2-cyclohexanediamine (1.87 g, 16.4 mmol) in glacial AcOH (200 mL) was added at 70° C. to a vigorously stirred solution of pyromellitic dianhydride (28.6 g, 131.0 mmol) in glacial AcOH (400 mL) under N$_2$. The resulting reaction mixture was then stirred at 120° C. for 12 h under N$_2$, after which time the solvent was removed under reduced pressure. The crude residue was dissolved in CH$_2$Cl$_2$ and subjected to column chromatography (SiO$_2$: CH$_2$Cl$_2$/Me$_2$CO, gradient from 0-10% Me$_2$CO) to afford pure (−)-2PMIA (5.5 g, 10.69 mmol) in 65% yield as a white solid. $^1$H NMR (500 MHz, CDCl$_3$, 25° C.) δ=8.33 (s, 4H), 5.08-4.98 (m, 2H), 2.60-2.42 (m, 2H), 2.04-1.90 (m, 4H), 1.69-1.46 (m, 2H). $^{13}$C NMR (125 MHz, CDCl$_3$, 25° C.) δ=165.1, 160.5, 137.7, 136.4, 121.0, 52.2, 29.0, 24.9. MALDI-TOF-HRMS (m/z): calcd for [M−H]$^-$=513.058; found: 513.429.

(−)-1NDI-2NH$_2$,

The synthetic protocol was adopted according to the literature procedure, except that a slightly modified procedure was used as follows.[Kaik, M.; Gawroński, *J. Org. Lett.* 2006, 8, 2921; Kaik, M.; Gawroński, J. *Tetrahedron: Asymmetry* 2003, 14, 1559] The compound (RR)-trans-1,2-cyclohexanediamine (1.14 g, 10.0 mmol) was added quickly in one portion to a vigorously stirred suspension of naphthalenetetracarboxylic dianhydride (1.34 g, 5.0 mmol) and p-toluenesulfonic acid monohydrate (1.90 g, 10.0 mmol) in anhydrous DMF (20 mL) at room temperature. The reaction mixture was stirred at 125° C. until a homogenous solution was obtained and the stirring was continued for an additional 2 h, after which time the homogenous solution became transformed into a suspension. The reaction mixture was cooled down to room temperature and the solvent was removed under reduced pressure. The crude residue was purified by precipitation, followed by filtration from MeOH-benzene to afford a ditosylate salt of (−)-1NDI-2NH$_2$ as a red solid. This ditosylate of (−)-1NDI-2NH$_2$ was taken up in CH$_2$Cl$_2$ (200 mL) and a saturated NaHCO$_3$ solution (50 mL) was added to this CH$_2$Cl$_2$ solution. The resulting solution was stirred overnight at room temperature. The organic layer was separated and the aqueous layer was extracted with CH$_2$Cl$_2$ (3×100 mL). The organic layers were combined, dried (MgSO$_4$) and concentrated under reduced pressure to afford pure (−)-1NDI-2NH$_2$ (1.38 g, 3.00 mmol) in 60% overall yield as a pale yellow solid. $^1$H NMR (500 MHz, CDCl$_3$, 25° C.) δ=8.72 (s, 4H), 4.90-4.65 (m, 2H), 3.73 (td, J=10.8, 4.1 Hz, 2H), 2.62-2.37 (m, 2H), 2.18-2.00 (m, 2H), 1.97-1.67 (m, 6H), 1.58-1.39 (m, 4H), 1.36-1.21 (m, 6H). $^{13}$C NMR (125 MHz, CDCl$_3$, 25° C.)δ=163.3, 131.4, 130.8, 126.9, 61.4, 50.5, 38.0, 28.9, 26.2, 25.5.

(−)-2PMDI-1NDI-Δ.

A warm suspension of (−)-1NDI-2NH$_2$ (0.92 g, 2.0 mmol) in anhydrous DMF (30 mL) was added quickly to a vigorously stirred homogenous solution of (−)-2PMIA (1.03 g, 2.0 mmol) in anhydrous DMF (80 mL) at 70° C. under N$_2$. The resulting reaction mixture was stirred overnight at 130° C. under N$_2$, after which time the DMF was removed under reduced pressure (~3 mbar) at 60° C. The deep red residue was dissolved in CH$_2$Cl$_2$ and subjected to column chromatography (SiO$_2$: CH$_2$Cl$_2$/Me$_2$CO, gradient from 0-10% Me$_2$CO) to afford pure (−)-2PMDI-1NDI-Δ (0.94 g, 1.0 mmol) in 50% yield as an off-white solid. $^1$H NMR (500 MHz, CDCl$_3$, 25° C.) δ=8.61 (d, J=7.7 Hz, 2H), 8.58 (d, J=7.7 Hz, 2H), 7.95 (d, J=0.9 Hz, 2H), 7.93 (d, J=0.9 Hz, 2H), 5.88 (td, J=11.7, 3.7 Hz, 2H), 5.50 (td, J=11.7, 3.6 Hz, 2H), 5.17-5.07 (m, 2H), 2.51-2.38 (m, 2H), 2.26-2.14 (m, 2H), 2.09-2.01 (m, 2H), 2.00-1.83 (m, 12H), 1.72-1.60 (m, 4H), 1.60-1.46 (m, 2H). $^{13}$C NMR (125 MHz, CDCl$_3$, 25° C.) δ=165.9, 165.7, 165.1, 162.7, 162.5, 136.6, 136.4, 136.2, 136.1, 131.8, 131.0, 126.6, 126.4, 126.0, 118.8, 54.1, 51.4, 51.3, 31.2, 31.1, 29.7, 25.6, 25.5, 25.1. ESI-HRMS (m/z): calcd for [M+H]$^+$=939.2620; found: 939.2607.

Example 3

NMR Spectroscopy

The unambiguous assignment of the various methine (—CH) and methylene (—CH$_2$) protons of the triangular macrocycle (−)-1PMDI-2NDI-Δ was established using 2D Correlation (COSY) and Nuclear Overhauser Effect (NOESY) NMR spectroscopy. The unambiguous assignment of various carbonyl, aromatic and cyclohexano carbons corresponding to the individual PMDI and NDI moieties of the triangular macrocycle (−)-1PMDI-2NDI-Δ was established using 2D $^1$H-$^{13}$C heteronuclear single quantum coherence (HSQC) and heteronuclear multiple bond correlation (HMBC) NMR spectroscopies.

The unambiguous assignment of various methine (—CH) and methylene (—CH$_2$) protons of the triangular macrocycle (−)-2PMDI-1NDI-Δ was established using 2D Correlation (COSY) and Nuclear Overhauser Effect (NOESY) NMR spectroscopy). The unambiguous assignment of various carbonyl, aromatic and cyclohexano carbons corresponding to the individual PMDI and NDI moieties of the triangular macrocycle (−)-2PMDI-1NDI-Δ was established using 2D $^1$H-$^{13}$C heteronuclear single quantum coherence (HSQC) and heteronuclear multiple bond correlation (HMBC) NMR spectroscopies.

Example 4

Crystallographic Characterization (−)-1PMDI-2NDI-Δ a) Method: Single crystals of (−)-1PMDI-2NDI-Δ were grown by slow vapor diffusion of n-hexane into a 3.0 mM solution in 1,2-dibromoethane over the course of 3 days. A suitable crystal was selected and mounted in inert oil and transferred to the cold gas stream of a Kappa Apex 2 diffractometer. The crystal was kept at 99.99 K during data collection. Using Olex2, the structure was solved with the She1XT structure solution program using Direct Methods and refined with the She1XL refinement package using Least Squares minimization.

b) Crystal Data: orthorhombic, space group P2$_1$2$_1$2$_1$ (no. 19), a=9.2311(4), b=18.4418(7), c=37.1578(14) Å, V=6325.7(4) Å3, Z=4, T=99.99 K, μ(CuKα)=6.632 mm−1, Dcalc=1.828 g/mm3, 90253 reflections measured (5.35≤2Θ≤133.336), 11099 unique (Rint=0.0720, Rsigma=0.0398) which were used in all calculations. The final R1 was 0.1034 (I>2σ(I)) and wR2 was 0.2688 (all data).

c) Refinement Details: Rigid bond restraints were imposed on the displacement parameters as well as restraints on similar amplitudes separated by less than 1.7 Å globally. Distance restraints were imposed on the 1,2-dibromoethane solvent molecules.

(−)-2PMDI-1NDI-Δ a) Method: Single crystals of (−)-2PMDI-1NDI-Δ were grown by slow vapor diffusion of water into a 5.0 mM solution in DMF over the course of 3 days. A suitable crystal was selected and mounted in inert oil and transferred to the cold gas stream of a Kappa Apex 2 diffractometer. The crystal was kept at 100.02 K during data collection. Using Olex2, the structure was solved with the She1XT structure solution program using Direct Methods and refined with the She1XL refinement package using Least Squares minimization.

b) Crystal Data: monoclinic, space group P2$_1$ (no. 4), a=18.6699(9), b=18.7951(9), c=33.5586(16) Å, β=94.656(2)°, V=11736.9(10) Å$^3$, Z=2, T=100.02 K, μ(CuKα)=0.755 mm$^{-1}$, D$_{calc}$=1.249 g/mm$^3$, 120580 reflections measured (2.642≤2Θ≤130.506), 39700 unique (R$_{int}$=0.0614, R$_{sigma}$=0.0707) which were used in all calculations. The final R$_1$ was 0.0703 (I>2σ(I)) and wR$_2$ was 0.2023 (all data).

c) Refinement Details: The enhanced rigid-bond restraint (SHELX keyword RIGU) was applied on the disordered oxygen atoms.[17]

d) Solvent Treatment Details: The solvent masking procedure as implemented in Olex2 was used to remove the electronic contribution of solvent molecules from the refinement. As the exact solvent content is not known, only the atoms used in the refinement model are reported in the formula here. Total solvent accessible volume/cell=1700.6 Å$^3$ [14.5%] and Total electron count/cell=596.7.

We claim:

1. A rigid triangular macrocycle comprising an ordered, alternating arrangement of three redox-active subunits and three linking subunits,
    wherein the first redox-active subunit is a naphthalene diimide-based (NDI) subunit, the second redox-active subunit is a pyromellitic diimide-based (PMDI) subunit, and the third redox-active subunit is the pyromellitic diimide-based (PMDI) subunit or the naphthalene diimide-based (NDI) subunit, and
    wherein the chiral linking subunit is a (RR)-trans-1,2-cycloalkyl subunit or a (SS)-trans-1,2-cycloalkyl subunit.

2. The macrocycle of claim 1, wherein the chiral linking subunit is a (RR)-trans-1,2-cyclohexyl subunit or a (SS)-trans-1,2-cyclohexyl subunit.

3. The macrocycle of claim 1, wherein the naphthalene diimide-based (NDI) subunit is prepared from a compound of Formula (XIII):

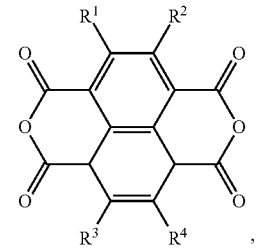

wherein R$^1$, R$^2$, R$^3$, and R$^4$ are, independently, selected from the group consisting of hydrogen, fluorine, chlorine, bromine, iodine, a C$_1$-C$_4$ alkyl moiety, a C$_1$-C$_4$ alkenyl moiety, a C$_1$-C$_4$ alkynyl moiety, a C$_0$-C$_4$ hydroxyl moiety, a C$_1$-C$_4$ alkoxy moiety, a C$_1$-C$_4$ phenoxy moiety, a C$_1$-C$_4$ carbonyl moiety, a C$_1$-C$_4$ cyano moiety, or a C$_1$-C$_4$ sulfate moiety and the pyromellitic diimide-based (PMDI) subunit is prepared from of a compound of Formula (XIV):

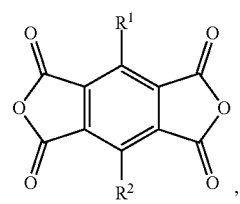

wherein $R^1$ and $R^2$ are, independently, selected from the group consisting of hydrogen, fluorine, chlorine, bromine, iodine, a $C_1$-$C_4$ alkyl moiety, a $C_1$-$C_4$ alkenyl moiety, a $C_1$-$C_4$ alkynyl moiety, a $C_0$-$C_4$ hydroxyl moiety, a $C_1$-$C_4$ alkoxy moiety, a $C_1$-$C_4$ phenoxy moiety, a $C_1$-$C_4$ carbonyl moiety, a $C_1$-$C_4$ cyano moiety, or a $C_1$-$C_4$ sulfate moiety, by reacting the compound of Formula (XII) or Formula (XIV) with a chiral linking subunit, wherein the chiral linking subunit is a (RR)-trans-1,2-cycloalkyldiamine subunit or a (SS)-trans-1,2-cycloalkyldiamine subunit.

4. The macrocycle of claim 1, wherein the redox-active subunits form a triangular macrocycle having $C_2$ symmetry.

5. The macrocycle of claim 1, wherein the macrocycle comprises a compound of (i) Formula (I):

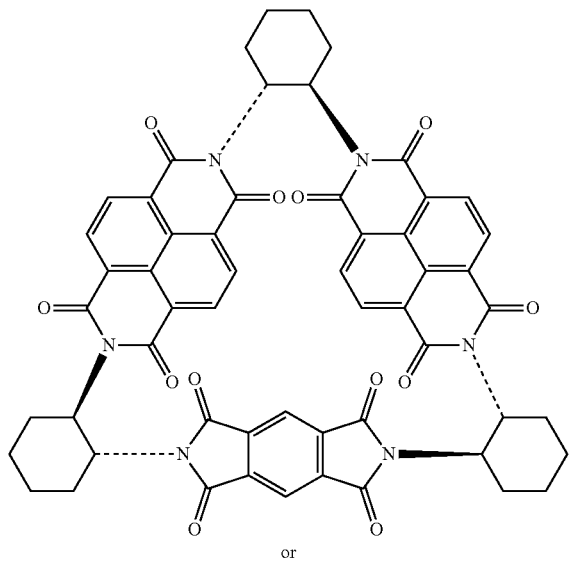

or (ii) Formula (II):

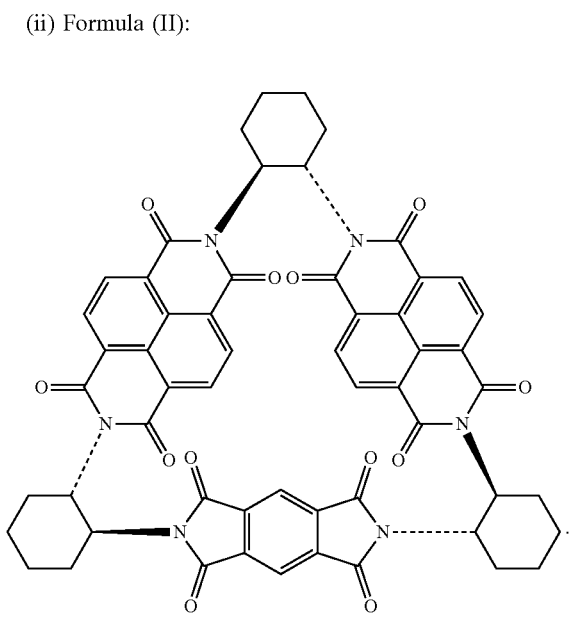

6. The macrocycle of claim 1, wherein the macrocycle comprises a compound of (i) Formula (III):

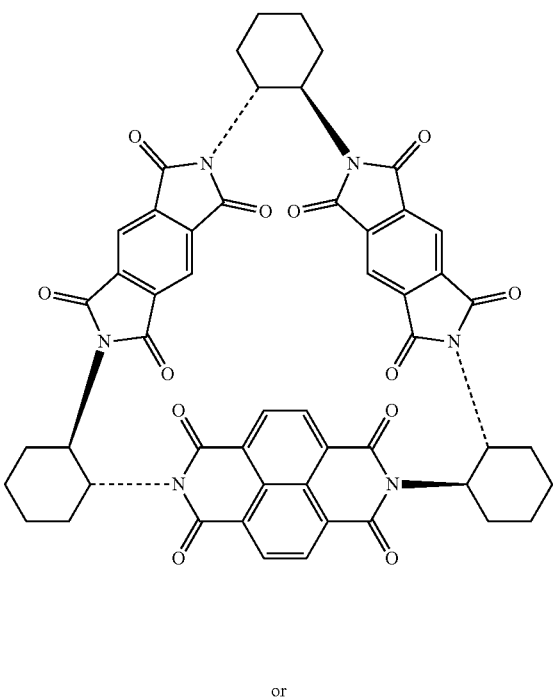

or (ii) Formula (IV):

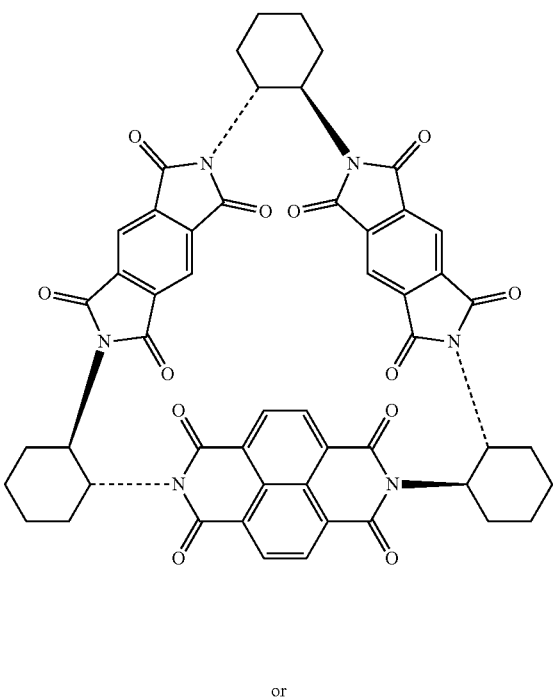

7. A cathodic material comprising a rigid macrocycle, wherein the macrocycle is the macrocycle as in claim 1.

8. The cathodic material of claim 7, wherein the macrocycle is a compound of
(i) Formula (I):

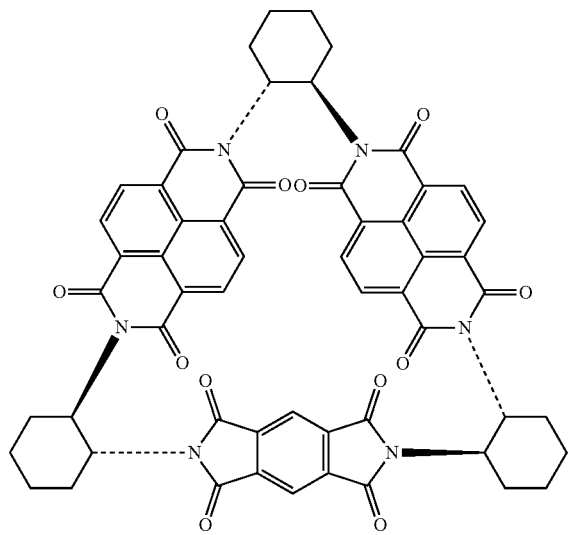

or (ii) Formula (II):

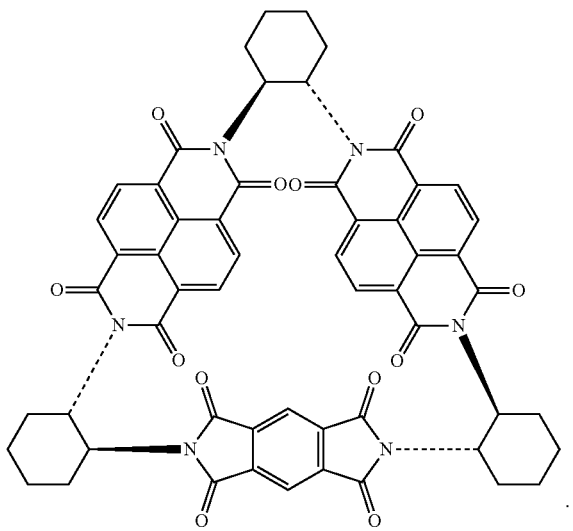

9. The cathodic material of claim 8, wherein the macrocycle of either Formula (I) or Formula (II) is lithiated.

10. The cathodic material of claim 7, wherein the macrocycle comprises a compound of
(i) Formula (III):

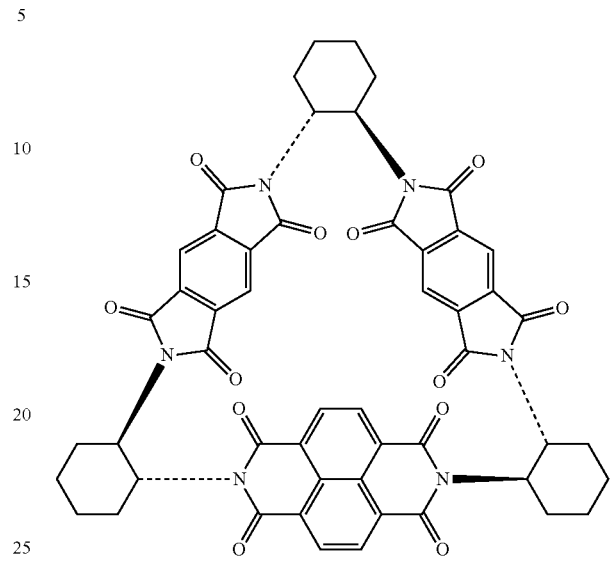

or (ii) Formula (IV):

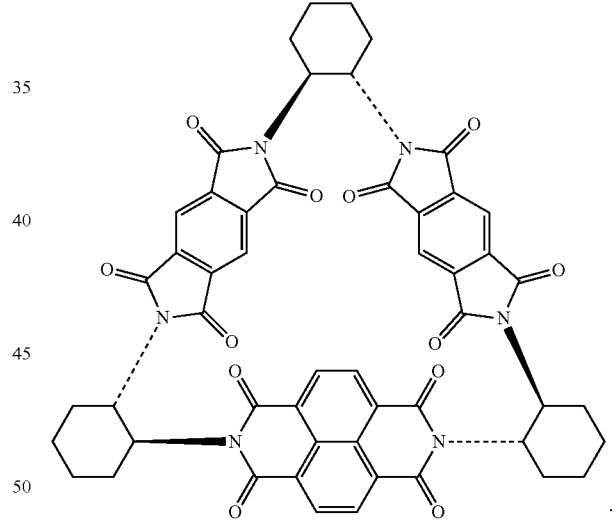

11. The cathodic material of claim 10, wherein the macrocycle of either Formula (III) or Formula (IV) is lithiated.

12. The cathodic material of claim 7 further comprising a binder material, the binder material comprises a polymer selected from the group consisting of:

styrene-butadiene rubber (SBR); polyvinylidene fluoride (PVDF);

polytetrafluoroethylene (PTFE); copolymer of tetrafluoroethylene, hexafluoropropylene, and vinylidene fluoride; copolymer of hexafluoropropylene and vinylidene fluoride; and copolymer of tetrafluoroethylene and perfluorinated vinyl ether.

13. The cathodic material of claim 7 further comprising an electron-conducting additive, the electron-conducting additive comprising a carbon or graphitic material selected from the list consisting of: a graphite, a carbon black, a graphene, a carbon nanotube, a chemically-etched or expanded soft carbon, a chemically-etched or expanded hard carbon, and an exfoliated activated carbon.

14. A battery comprising a cathode and an electrolyte material, wherein the cathode comprises the cathodic material as in claim 7.

15. The battery of claim 14, wherein the electrolyte material comprises NiCd, Li-ion, Li-ion polymer, lead acid, and/or alkaline.

16. The battery of claim 14, wherein the electrolyte material comprises a non-coordinating anion salt comprising a member selected from the group consisting of lithium hexafluorophosphate, lithium hexafluoroarsenate monohydrate, lithium perchlorate, lithium tetrafluoroborate, lithium triflate, and any combination thereof.

17. A method for preparing the rigid triangular macrocycle according to claim 1, the method comprising cyclocondensing the three redox-active subunits and the three linking subunits in an ordered, alternating arrangement, wherein the method comprises reacting a first reagent, wherein the first reagent comprises one redox-active subunit selected from the naphthalene diimide-based (NDI) subunit and the pyromellitic diimide-based (PMDI) subunit, and a second reagent, wherein the second reagent comprises two redox active subunits each selected from the naphthalene diimide-based (NDI) subunit and the pyromellitic diimide-based (PMDI) subunit, wherein the redox-active subunit of the first reagent and the redox-active subunits of the second reagent are different.

18. The method of claim 17, wherein the second reagent comprises a compound of
(i) Formula (V):

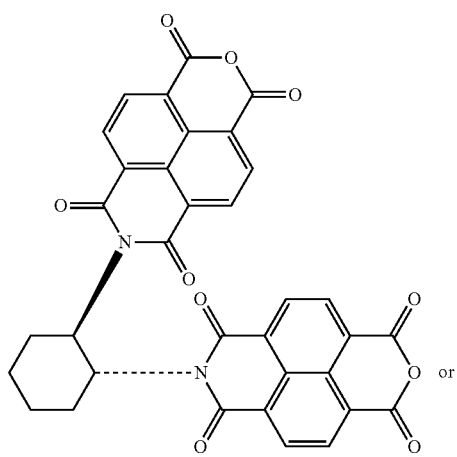

or (ii) Formula (VI):

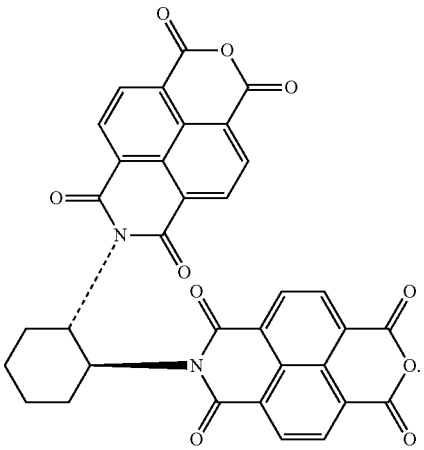 [SMILES: O=C1OC(=O)c2ccc3c4c(ccc1c24)C(=O)N([C@H]1CCCC[C@@H]1N1C(=O)c2ccc4c5c(ccc(c25)C1=O)C(=O)OC4=O)C3=O]

19. The method of claim 18, wherein the first reagent comprises a compound of
(i) Formula (VII):

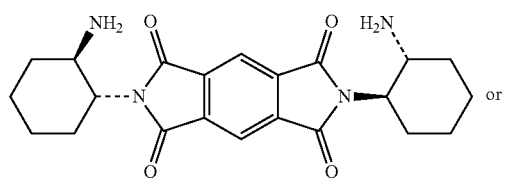

or (ii) Formula (VIII):

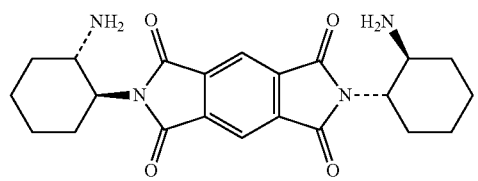

20. The method of claim 17, wherein the second reagent comprises a compound of
(i) Formula (IX):

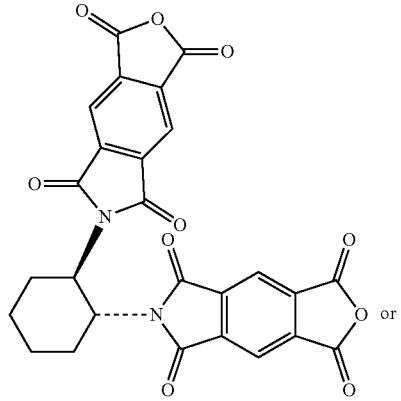

or (ii) Formula (X):

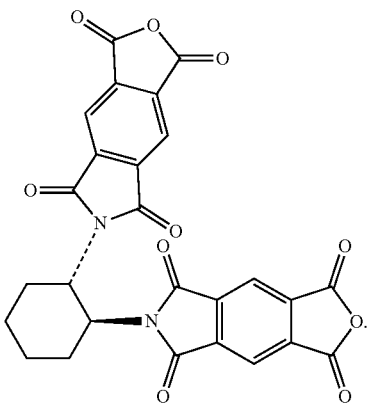 [SMILES: O=c1oc(=O)c2cc3c(=O)n([C@H]4CCCC[C@@H]4n4c(=O)c5cc6c(=O)oc(=O)c6cc5c4=O)c(=O)c3cc12]

21. The method of claim 20, wherein the first reagent comprises a compound of
(i) Formula (XI):

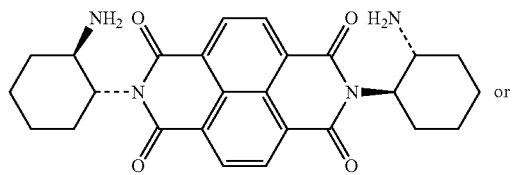

or (ii) Formula (XII):

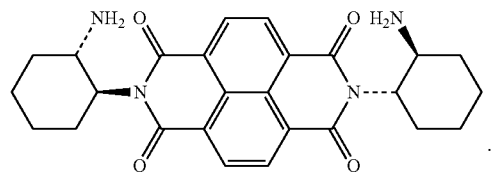

22. The method of claim 17, wherein the first reagent or the second reagent is prepared by reacting either a compound of (i) Formula (XIII):

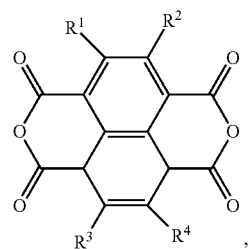

wherein R1, R2, R3, and R4 are, independently, selected from the group consisting of hydrogen, fluorine, chlorine, bromine, iodine, a $C_1$-$C_4$ alkyl moiety, a $C_1$-$C_4$ alkenyl moiety, a $C_1$-$C_4$ alkynyl moiety, a $C_0$-$C_4$ hydroxyl moiety, a $C_1$-$C_4$ alkoxy moiety, a $C_1$-$C_4$ phenoxy moiety, a $C_1$-$C_4$ carbonyl moiety, a $C_1$-$C_4$ cyano moiety, or a $C_1$-$C_4$ sulfate moiety, or (ii) Formula (XIV):

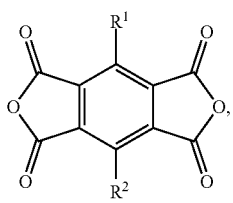

wherein R1 and R2 are, independently, selected from the group consisting of hydrogen, fluorine, chlorine, bromine, iodine, a $C_1$-$C_4$ alkyl moiety, a $C_1$-$C_4$ alkenyl moiety, a $C_1$-$C_4$ alkynyl moiety, a $C_0$-$C_4$ hydroxyl moiety, a $C_1$-$C_4$ alkoxy moiety, a $C_1$-$C_4$ phenoxy moiety, a $C_1$-$C_4$ carbonyl moiety, a $C_1$-$C_4$ cyano moiety, or a $C_1$-$C_4$ sulfate moiety, with a chiral linking subunit, wherein the chiral linking subunit is a (RR)-trans-1,2-cycloalkyldiamine subunit or a (SS)-trans-1,2-cycloalkyldiamine subunit.

\* \* \* \* \*